(12) United States Patent
Fischell et al.

(10) Patent No.: US 11,202,889 B2
(45) Date of Patent: *Dec. 21, 2021

(54) PERI-VASCULAR TISSUE ABLATION CATHETER WITH SUPPORT STRUCTURES

(71) Applicant: Ablative Solutions, Inc., San Jose, CA (US)

(72) Inventors: David R. Fischell, Fair Haven, NJ (US); Tim A. Fischell, Kalamazoo, MI (US); Robert Ryan Ragland, Temecula, CA (US); Darrin James Kent, Murrieta, CA (US); Andy Edward Denison, Temecula, CA (US); Eric Thomas Johnson, Temecula, CA (US); Jeff Alan Burke, Winchester, CA (US); Christopher Scott Hayden, Winchester, CA (US); Robert E. Fischell, Dayton, MD (US)

(73) Assignee: Ablative Solutions, Inc., Wakefield, MA (US)

( * ) Notice: Subject to any disclaimer, the term of this patent is extended or adjusted under 35 U.S.C. 154(b) by 146 days.

This patent is subject to a terminal disclaimer.

(21) Appl. No.: 16/509,995

(22) Filed: Jul. 12, 2019

(65) Prior Publication Data
US 2020/0061348 A1 Feb. 27, 2020

Related U.S. Application Data

(63) Continuation of application No. 15/383,528, filed on Dec. 19, 2016, now Pat. No. 10,350,392, which is a (Continued)

(51) Int. Cl.
*A61M 25/10* (2013.01)
*A61M 5/158* (2006.01)
(Continued)

(52) U.S. Cl.
CPC .............. *A61M 25/10* (2013.01); *A61B 18/00* (2013.01); *A61B 18/04* (2013.01); *A61M 5/158* (2013.01);
(Continued)

(58) Field of Classification Search
CPC .............. A61M 25/0662; A61M 25/10; A61M 25/0084; A61M 2025/0086;
(Continued)

(56) References Cited

U.S. PATENT DOCUMENTS 3,119,391 A 1/1964 Harrison
4,578,061 A 3/1986 Lemelson
(Continued)

FOREIGN PATENT DOCUMENTS

CN 1147964 4/1997
CN 1269708 1/2000
(Continued)

OTHER PUBLICATIONS

U.S. Appl. No. 15/940,178, filed Mar. 29, 2018, Fischell et al.
(Continued)

*Primary Examiner* — Manuel A Mendez
*Assistant Examiner* — Justin L Zamory
(74) *Attorney, Agent, or Firm* — Knobbe, Martens, Olson & Bear, LLP

(57) ABSTRACT

An intravascular catheter for peri-vascular and/or peri-urethral tissue ablation includes multiple needles advanced through supported guide tubes which expand around a central axis to engage the interior surface of the wall of the renal artery or other vessel of a human body allowing the injection an ablative fluid for ablating tissue, and/or nerve fibers in the outer layer or deep to the outer layer of the vessel, or in prostatic tissue. The catheter may also include structures which provide radial and/or lateral support to the (Continued)

guide tubes so that the guide tubes expand uniformly and maintain their position against the interior surface of the vessel wall as the sharpened injection needles are advanced to penetrate into the vessel wall.

22 Claims, 18 Drawing Sheets

Related U.S. Application Data continuation of application No. 14/266,726, filed on Apr. 30, 2014, now Pat. No. 9,526,827, which is a continuation-in-part of application No. 13/752,062, filed on Jan. 28, 2013, now Pat. No. 8,740,849.

(60) Provisional application No. 61/719,906, filed on Oct. 29, 2012.

(51) Int. Cl.
*A61M 25/00* (2006.01)
*A61B 18/00* (2006.01)
*A61B 18/04* (2006.01)
*A61M 25/06* (2006.01)
*A61B 90/00* (2016.01)

(52) U.S. Cl.
CPC .... *A61M 25/0084* (2013.01); *A61M 25/0662* (2013.01); *A61B 2018/00011* (2013.01); *A61B 2018/00279* (2013.01); *A61B 2018/00404* (2013.01); *A61B 2018/00517* (2013.01); *A61B 2018/00577* (2013.01); *A61B 2018/046* (2013.01); *A61B 2090/3966* (2016.02); *A61B 2218/002* (2013.01); *A61M 2005/1585* (2013.01); *A61M 2025/0087* (2013.01)

(58) Field of Classification Search
CPC .. A61M 2025/0087; A61M 2005/1585; A61B 18/04; A61B 2018/00011; A61B 2018/00517

See application file for complete search history.

(56) References Cited

U.S. PATENT DOCUMENTS

| | | |
|---|---|---|
| 4,798,595 A | 1/1989 | Anderson et al. |
| 5,304,141 A | 4/1994 | Johnson et al. |
| 5,354,279 A | 10/1994 | Hofling |
| 5,385,562 A | 1/1995 | Adams et al. |
| 5,405,376 A | 4/1995 | Mulier et al. |
| 5,419,777 A | 5/1995 | Hofling |
| 5,431,649 A | 7/1995 | Mulier et al. |
| 5,464,395 A | 11/1995 | Faxon et al. |
| 5,474,102 A | 12/1995 | Lopez |
| 5,551,426 A | 9/1996 | Hummel et al. |
| 5,588,960 A | 12/1996 | Edwards et al. |
| 5,667,488 A | 9/1997 | Lundquist et al. |
| 5,672,173 A | 9/1997 | Gough |
| 5,683,384 A | 11/1997 | Gough |
| 5,713,863 A | 2/1998 | Vigil et al. |
| 5,792,094 A | 8/1998 | Stevens et al. |
| 5,800,379 A | 9/1998 | Edwards |
| 5,855,576 A | 1/1999 | LeVeen et al. |
| 5,902,289 A | 5/1999 | Swartz et al. |
| 5,971,958 A | 10/1999 | Zhang |
| 5,980,516 A | 11/1999 | Mulier et al. |
| 6,056,744 A | 5/2000 | Edwards |
| 6,106,521 A | 8/2000 | Blewett et al. |
| 6,165,164 A | 12/2000 | Hill et al. |
| 6,190,353 B1 | 2/2001 | Makower et al. |
| 6,190,393 B1 | 2/2001 | Bevier et al. |
| 6,217,554 B1 | 4/2001 | Green |
| 6,221,049 B1 | 4/2001 | Selmon et al. |
| 6,231,597 B1 | 5/2001 | Deem et al. |
| 6,254,599 B1 | 7/2001 | Lesh et al. |
| 6,277,107 B1 | 8/2001 | Lurie et al. |
| 6,283,947 B1 | 9/2001 | Mirzaee |
| 6,283,951 B1 | 9/2001 | Flaherty et al. |
| 6,302,870 B1 | 10/2001 | Jacobsen et al. |
| 6,375,660 B1 | 4/2002 | Fischell et al. |
| 6,416,510 B1 | 7/2002 | Altman et al. |
| 6,432,092 B2 | 8/2002 | Miller |
| 6,478,778 B1 | 11/2002 | Jacobsen et al. |
| 6,514,248 B1 | 2/2003 | Eggers et al. |
| 6,547,803 B2 | 4/2003 | Seward et al. |
| 6,599,267 B1 | 7/2003 | Ray et al. |
| 6,652,517 B1 | 11/2003 | Hall et al. |
| 6,685,648 B2 | 2/2004 | Flaherty et al. |
| 6,692,466 B1 * | 2/2004 | Chow ............... A61M 25/0084 604/164.01 |
| 6,764,461 B2 | 7/2004 | Mickley et al. |
| 6,854,467 B2 | 2/2005 | Boekstegers |
| 6,855,124 B1 | 2/2005 | Gonzalez et al. |
| 6,905,480 B2 | 6/2005 | McGuckin et al. |
| 6,966,897 B2 | 11/2005 | Shimazaki |
| 6,978,174 B2 | 12/2005 | Gelfand et al. |
| 6,997,903 B2 | 2/2006 | Wijay et al. |
| 7,015,253 B2 | 3/2006 | Escandon et al. |
| 7,056,286 B2 | 6/2006 | Ravenscroft et al. |
| 7,087,040 B2 | 8/2006 | McGuckin, Jr. et al. |
| 7,094,202 B2 | 8/2006 | Nobis et al. |
| 7,162,303 B2 | 1/2007 | Levin et al. |
| 7,181,288 B1 | 2/2007 | Rezai et al. |
| 7,273,469 B1 | 9/2007 | Chan et al. |
| 7,326,238 B1 | 2/2008 | Kilpatrick |
| 7,472,705 B2 | 1/2009 | Baran |
| 7,617,005 B2 | 11/2009 | Demarais et al. |
| 7,621,945 B2 | 11/2009 | Lennox et al. |
| 7,647,115 B2 | 1/2010 | Levin et al. |
| 7,653,438 B2 | 1/2010 | Deem et al. |
| 7,666,163 B2 | 2/2010 | Seward et al. |
| 7,691,080 B2 | 4/2010 | Seward et al. |
| 7,691,086 B2 | 4/2010 | Tkebuchava |
| 7,717,899 B2 | 5/2010 | Bowe et al. |
| 7,717,948 B2 | 5/2010 | Demarais et al. |
| 7,744,584 B2 | 6/2010 | Seward et al. |
| 7,756,583 B2 | 7/2010 | Demarais et al. |
| 7,794,444 B2 | 9/2010 | Lesh et al. |
| 7,850,656 B2 | 12/2010 | McKay et al. |
| 7,862,563 B1 | 1/2011 | Cosman et al. |
| 7,873,417 B2 | 1/2011 | Demarais et al. |
| 7,881,807 B2 | 2/2011 | Schaer |
| 7,942,854 B1 | 5/2011 | Von Oepen et al. |
| 8,000,764 B2 | 8/2011 | Rashidi |
| 8,088,127 B2 | 1/2012 | Mayse et al. |
| 8,100,883 B1 | 1/2012 | Johnson |
| 8,131,371 B2 | 3/2012 | Demarals et al. |
| 8,131,372 B2 | 3/2012 | Levin et al. |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,152,758 B2 * | 4/2012 | Chan ............... A61M 25/0084 604/96.01 |
| 8,152,804 B2 | 4/2012 | Elmouelhi et al. |
| 8,175,711 B2 | 5/2012 | Demarais et al. |
| 8,396,548 B2 | 3/2013 | Perry et al. |
| 8,399,443 B2 | 3/2013 | Seward et al. |
| 8,465,451 B2 | 6/2013 | McRae et al. |
| 8,465,752 B2 | 6/2013 | Seward |
| 8,663,190 B2 | 3/2014 | Fischell et al. |
| 8,684,998 B2 | 4/2014 | Demarais et al. |
| 8,708,995 B2 | 4/2014 | Seward et al. |
| 8,740,849 B1 | 6/2014 | Fischell et al. |
| 8,771,252 B2 | 7/2014 | Gelfand et al. |
| 8,852,163 B2 | 10/2014 | Deem et al. |
| 8,880,186 B2 | 11/2014 | Levin et al. |
| 8,934,978 B2 | 1/2015 | Deem et al. |
| 8,948,865 B2 | 2/2015 | Zarins et al. |
| 8,975,233 B2 | 3/2015 | Stein et al. |
| 8,979,801 B2 | 3/2015 | Lamson et al. |

(56) References Cited

U.S. PATENT DOCUMENTS

| | | |
|---|---|---|
| 8,983,595 B2 | 3/2015 | Levin et al. |
| 9,011,879 B2 | 4/2015 | Seward |
| 9,056,185 B2 | 6/2015 | Fischell et al. |
| 9,125,661 B2 | 9/2015 | Deem et al. |
| 9,131,978 B2 | 9/2015 | Zarins et al. |
| 9,131,983 B2 | 9/2015 | Fischell et al. |
| 9,138,281 B2 | 9/2015 | Zarins et al. |
| 9,179,962 B2 | 11/2015 | Fischell et al. |
| 9,192,715 B2 | 11/2015 | Gelfand et al. |
| 9,199,065 B2 | 12/2015 | Seward |
| 9,237,925 B2 | 1/2016 | Fischell et al. |
| 9,254,360 B2 | 2/2016 | Fischell et al. |
| 9,265,558 B2 | 2/2016 | Zarins et al. |
| 9,278,196 B2 | 3/2016 | Fischell et al. |
| 9,289,255 B2 | 3/2016 | Deem et al. |
| 9,301,795 B2 | 4/2016 | Fischell et al. |
| 9,308,044 B2 | 4/2016 | Zarins et al. |
| 9,314,630 B2 | 4/2016 | Levin et al. |
| 9,320,561 B2 | 4/2016 | Zarins et al. |
| 9,320,850 B2 | 4/2016 | Fischell et al. |
| 9,326,817 B2 | 5/2016 | Zarins et al. |
| 9,439,726 B2 | 9/2016 | Zarins et al. |
| 9,456,869 B2 | 10/2016 | Zarins et al. |
| 9,474,563 B2 | 10/2016 | Zarins et al. |
| 9,486,270 B2 | 11/2016 | Zarins et al. |
| 9,526,827 B2 | 12/2016 | Fischell et al. |
| 9,539,047 B2 | 1/2017 | Fischell et al. |
| 9,554,849 B2 | 1/2017 | Fischell et al. |
| 9,629,675 B2 | 4/2017 | Kleshinski et al. |
| 9,636,174 B2 | 5/2017 | Zarins et al. |
| 9,675,413 B2 | 6/2017 | Deem et al. |
| 9,743,983 B2 | 8/2017 | Levin et al. |
| 9,757,192 B2 | 9/2017 | Levin et al. |
| 9,789,276 B2 | 10/2017 | Seward et al. |
| 9,795,441 B2 | 10/2017 | Fischell et al. |
| 9,814,873 B2 | 11/2017 | Zarins et al. |
| 9,895,195 B2 | 2/2018 | Zarins et al. |
| 9,907,611 B2 | 3/2018 | Levin et al. |
| 9,931,046 B2 | 4/2018 | Fischell et al. |
| 9,949,652 B2 | 4/2018 | Fischell et al. |
| 9,993,278 B2 | 6/2018 | Rioux et al. |
| 10,022,059 B2 | 7/2018 | Fischell et al. |
| 10,118,004 B2 | 11/2018 | Fischell et al. |
| 10,172,663 B2 | 1/2019 | Fischell et al. |
| 10,226,278 B2 | 3/2019 | Fischell et al. |
| 10,350,392 B2 | 7/2019 | Fischell et al. |
| 10,405,912 B2 | 9/2019 | Fischell et al. |
| 10,420,481 B2 | 9/2019 | Fischell et al. |
| 10,485,951 B2 | 11/2019 | Fischell et al. |
| 10,517,666 B2 | 12/2019 | Fischell et al. |
| 10,576,246 B2 | 3/2020 | Fischell et al. |
| 10,736,524 B2 | 8/2020 | Fischell et al. |
| 10,736,656 B2 | 8/2020 | Fischell et al. |
| 10,849,685 B2 | 12/2020 | Denison et al. |
| 10,881,312 B2 | 1/2021 | Fischell et al. |
| 10,881,458 B2 | 1/2021 | Fischell et al. |
| 10,945,787 B2 | 3/2021 | Fischell et al. |
| 2001/0037065 A1 | 11/2001 | Graf et al. |
| 2002/0010439 A1 | 1/2002 | Miller |
| 2002/0052577 A1 | 5/2002 | Shimazaki et al. |
| 2002/0082584 A1 | 6/2002 | Rosenman et al. |
| 2002/0120238 A1 | 8/2002 | McGuckin et al. |
| 2002/0151866 A1 | 10/2002 | Lundkvist et al. |
| 2002/0177846 A1 | 11/2002 | Mulier et al. |
| 2002/0183738 A1 | 12/2002 | Chee et al. |
| 2003/0009095 A1 | 1/2003 | Skarda |
| 2003/0032929 A1 | 2/2003 | McGuckin, Jr. |
| 2003/0171723 A1 | 9/2003 | Ponzi |
| 2004/0064098 A1 | 4/2004 | Cuschieri et al. |
| 2004/0133154 A1 | 7/2004 | Flaherty et al. |
| 2004/0147902 A1 | 7/2004 | McGuckin, Jr. et al. |
| 2005/0070885 A1 | 3/2005 | Nobis et al. |
| 2005/0096647 A1 | 5/2005 | Steinke et al. |
| 2005/0187546 A1 | 8/2005 | Bek et al. |
| 2005/0234437 A1 | 10/2005 | Baxter et al. |
| 2005/0245923 A1 | 11/2005 | Christopherson et al. |
| 2005/0288730 A1 | 12/2005 | Deem et al. |
| 2006/0064056 A1 | 3/2006 | Coyle et al. |
| 2006/0064065 A1 | 3/2006 | Russo |
| 2006/0173440 A1 | 8/2006 | Lamson et al. |
| 2006/0189940 A1 | 8/2006 | Kirsch |
| 2006/0224118 A1 | 10/2006 | Morris et al. |
| 2006/0271111 A1 | 11/2006 | Demarais et al. |
| 2006/0271135 A1 | 11/2006 | Minar et al. |
| 2006/0293647 A1 | 12/2006 | Mcrea et al. |
| 2007/0005018 A1 | 1/2007 | Tekbuchava |
| 2007/0060812 A1 | 3/2007 | Harel et al. |
| 2007/0083239 A1 | 4/2007 | Demarias et al. |
| 2007/0129720 A1 | 6/2007 | Demarais et al. |
| 2007/0129760 A1 | 6/2007 | Demarais et al. |
| 2007/0173899 A1 | 7/2007 | Levin et al. |
| 2007/0185483 A1 | 8/2007 | Butty et al. |
| 2007/0203549 A1 | 8/2007 | Demarais et al. |
| 2007/0244479 A1 | 10/2007 | Beatty et al. |
| 2007/0270751 A1 | 11/2007 | Stangenes |
| 2007/0270757 A1 | 11/2007 | Willis et al. |
| 2008/0039786 A1 | 2/2008 | Epstein et al. |
| 2008/0045890 A1 | 2/2008 | Seward et al. |
| 2008/0051756 A1 | 2/2008 | Makower et al. |
| 2008/0125709 A1 | 5/2008 | Chang et al. |
| 2008/0188812 A1 | 8/2008 | Valaie |
| 2008/0213331 A1 | 9/2008 | Gelfand et al. |
| 2008/0300454 A1 | 12/2008 | Goto |
| 2009/0018526 A1 | 1/2009 | Power |
| 2009/0018638 A1 | 1/2009 | Shirley et al. |
| 2009/0036948 A1 | 2/2009 | Levin et al. |
| 2009/0076500 A1 | 3/2009 | Azure |
| 2009/0312617 A1 | 12/2009 | Creed et al. |
| 2010/0076545 A1 | 3/2010 | Kleshinski et al. |
| 2010/0114087 A1 | 5/2010 | Edwards |
| 2010/0137860 A1 | 6/2010 | Demarais et al. |
| 2010/0137952 A1 | 6/2010 | Demarais et al. |
| 2010/0179416 A1 | 7/2010 | Hoey et al. |
| 2010/0191112 A1 | 7/2010 | Demarais et al. |
| 2010/0222851 A1 | 9/2010 | Deem et al. |
| 2010/0268307 A1 | 10/2010 | Demarais et al. |
| 2010/0298948 A1 | 11/2010 | Hoey et al. |
| 2010/0305546 A1 | 12/2010 | Seward et al. |
| 2010/0324446 A1 | 12/2010 | Pendleton |
| 2011/0009848 A1 | 1/2011 | Woodard et al. |
| 2011/0104060 A1 | 5/2011 | Seward |
| 2011/0104061 A1 | 5/2011 | Seward |
| 2011/0112400 A1 | 5/2011 | Emery et al. |
| 2011/0146674 A1 | 6/2011 | Roschak |
| 2011/0172593 A1 | 7/2011 | Lyyikainen et al. |
| 2011/0182912 A1 | 7/2011 | Evans et al. |
| 2011/0184337 A1 | 7/2011 | Evans et al. |
| 2011/0195971 A1 | 8/2011 | Cincotta |
| 2011/0202098 A1 | 8/2011 | Demarais et al. |
| 2011/0207758 A1 | 8/2011 | Sobotka et al. |
| 2011/0208096 A1 | 8/2011 | Demarais et al. |
| 2011/0257564 A1 | 10/2011 | Demarais et al. |
| 2011/0257622 A1 | 10/2011 | Salahieh et al. |
| 2011/0295354 A1 | 12/2011 | Bueche et al. |
| 2012/0010524 A1 | 1/2012 | Fojtik et al. |
| 2012/0041419 A1 | 2/2012 | Blanchard et al. |
| 2012/0053604 A1 | 3/2012 | DiCaprio |
| 2012/0071832 A1 | 3/2012 | Bunch |
| 2012/0083877 A1 | 4/2012 | Nguyen et al. |
| 2012/0101490 A1 | 4/2012 | Smith |
| 2012/0108517 A1 | 5/2012 | Evans et al. |
| 2012/0116438 A1 | 5/2012 | Salahieh et al. |
| 2012/0130269 A1 | 5/2012 | Rea |
| 2012/0130289 A1 | 5/2012 | Demarais et al. |
| 2012/0130345 A1 | 5/2012 | Levin et al. |
| 2012/0143181 A1 | 6/2012 | Demarais et al. |
| 2012/0197198 A1 | 8/2012 | Demarais et al. |
| 2012/0197252 A1 | 8/2012 | Deem et al. |
| 2012/0253186 A1 | 10/2012 | Simpson et al. |
| 2012/0253192 A1 | 10/2012 | Cressman |
| 2012/0271277 A1 | 10/2012 | Fischell et al. |
| 2012/0271301 A1 | 10/2012 | Fischell et al. |
| 2012/0296329 A1 | 11/2012 | Ng |
| 2013/0053792 A1 | 2/2013 | Fischell et al. |

(56) References Cited

U.S. PATENT DOCUMENTS

| | | |
|---|---|---|
| 2013/0053821 A1 | 2/2013 | Fischell et al. |
| 2013/0053822 A1 | 2/2013 | Fischell et al. |
| 2013/0090637 A1 | 4/2013 | Sliwa |
| 2013/0103026 A1 | 4/2013 | Kleshinski et al. |
| 2013/0131743 A1 | 5/2013 | Yamasaki et al. |
| 2013/0138082 A1 | 5/2013 | Salahieh et al. |
| 2013/0144251 A1 | 6/2013 | Sobotka |
| 2013/0178910 A1 | 7/2013 | Azamian et al. |
| 2013/0274614 A1 | 10/2013 | Shimada et al. |
| 2013/0274673 A1 | 10/2013 | Fischell et al. |
| 2013/0274674 A1 | 10/2013 | Fischell et al. |
| 2013/0287698 A1 | 10/2013 | Seward |
| 2014/0024959 A1 | 1/2014 | Sobotka |
| 2014/0025041 A1 | 1/2014 | Fukuoka et al. |
| 2014/0046298 A1 | 2/2014 | Fischell et al. |
| 2014/0121641 A1 | 5/2014 | Fischell et al. |
| 2014/0121644 A1 | 5/2014 | Fischell et al. |
| 2014/0127126 A1 | 5/2014 | Lifton et al. |
| 2014/0236103 A1 | 8/2014 | Fischell et al. |
| 2014/0316351 A1 | 10/2014 | Fischell et al. |
| 2014/0358079 A1 | 12/2014 | Fischell et al. |
| 2014/0378906 A1 | 12/2014 | Fischell et al. |
| 2015/0005719 A1 | 1/2015 | Fischell et al. |
| 2015/0119674 A1 | 4/2015 | Fischell et al. |
| 2015/0119875 A1 | 4/2015 | Fischell et al. |
| 2015/0126965 A1 | 5/2015 | Liungman |
| 2015/0132409 A1 | 5/2015 | Stein et al. |
| 2015/0202220 A1 | 7/2015 | Stein et al. |
| 2015/0224289 A1 | 8/2015 | Seward |
| 2015/0245863 A1 | 9/2015 | Fischell et al. |
| 2015/0335384 A1 | 11/2015 | Fischell et al. |
| 2015/0343156 A1 | 12/2015 | Fischell et al. |
| 2016/0045257 A1 | 2/2016 | Fischell et al. |
| 2016/0058489 A1 | 3/2016 | Fischell et al. |
| 2016/0120587 A1 | 5/2016 | Fischell et al. |
| 2016/0235464 A1 | 8/2016 | Fischell et al. |
| 2016/0242661 A1 | 8/2016 | Fischell et al. |
| 2016/0279384 A1 | 9/2016 | Zarins et al. |
| 2016/0338734 A1 | 11/2016 | Shah et al. |
| 2016/0354137 A1 | 12/2016 | Fischell et al. |
| 2017/0119408 A1 | 5/2017 | Ma |
| 2017/0119974 A1 | 5/2017 | Racz |
| 2017/0304594 A1 | 10/2017 | Fischell et al. |
| 2017/0326363 A1 | 11/2017 | Deem et al. |
| 2017/0332926 A1 | 11/2017 | Fischell et al. |
| 2018/0043107 A1 | 2/2018 | Hooven et al. |
| 2018/0071019 A1 | 3/2018 | Fischell et al. |
| 2018/0085554 A1 | 3/2018 | Kassab et al. |
| 2018/0193596 A1 | 7/2018 | Fischell et al. |
| 2018/0279894 A1 | 10/2018 | Fischell et al. |
| 2019/0008580 A1 | 1/2019 | Fischell et al. |
| 2019/0015002 A1 | 1/2019 | Fischell et al. |
| 2019/0076186 A1 | 3/2019 | Fischell et al. |
| 2019/0076187 A1 | 3/2019 | Fischell et al. |
| 2019/0076188 A1 | 3/2019 | Fischell et al. |
| 2019/0117936 A9 | 4/2019 | Fischell et al. |
| 2019/0167918 A1 | 6/2019 | Fischell et al. |
| 2019/0201070 A1 | 7/2019 | Fischell et al. |
| 2019/0269435 A1 | 9/2019 | Fischell et al. |
| 2020/0022751 A1 | 1/2020 | Fischell et al. |
| 2020/0061348 A1 | 2/2020 | Fischell et al. |
| 2020/0163566 A1 | 5/2020 | Fischell et al. |
| 2020/0188007 A1 | 6/2020 | Fischell et al. |
| 2020/0197079 A1 | 6/2020 | Fischell et al. |
| 2020/0197663 A1 | 6/2020 | Fischell et al. |
| 2020/0269015 A1 | 8/2020 | Fischell et al. |
| 2021/0015381 A1 | 1/2021 | Fischell et al. |
| 2021/0015518 A1 | 1/2021 | Fischell et al. |
| 2021/0161594 A1 | 6/2021 | Denison et al. |

FOREIGN PATENT DOCUMENTS

| | | |
|---|---|---|
| CN | 1290148 | 4/2001 |
| CN | 101518470 | 9/2002 |
| CN | 1494399 | 5/2004 |
| CN | 1927130 | 3/2007 |
| CN | 101888807 | 11/2010 |
| CN | 102274074 | 12/2011 |
| EP | 0 797 409 | 10/1997 |
| EP | 0834288 | 4/1998 |
| EP | 1332724 | 8/2003 |
| EP | 0876805 | 8/2006 |
| EP | 2911735 | 9/2015 |
| JP | H06-277294 | 10/1994 |
| JP | H07509389 | 10/1995 |
| JP | H0889582 | 4/1996 |
| JP | 2001527428 | 12/2001 |
| JP | 2002-507458 | 3/2002 |
| JP | 2002510229 | 4/2002 |
| JP | 2002542901 | 12/2002 |
| JP | 2003-510126 | 3/2003 |
| JP | 2004-505689 | 2/2004 |
| JP | 2004516042 | 6/2004 |
| JP | 2004-528062 | 9/2004 |
| JP | 2005-40599 | 2/2005 |
| JP | 2005-506101 | 3/2005 |
| JP | 2008506500 | 3/2008 |
| JP | 09509865 | 3/2009 |
| JP | 2013-517847 | 5/2013 |
| WO | WO94/04220 | 3/1994 |
| WO | WO 95/13752 | 5/1995 |
| WO | WO 2004/030740 | 4/2004 |
| WO | WO 2006/084256 | 8/2006 |
| WO | WO 2007/121143 | 10/2007 |
| WO | WO 2009/137819 | 11/2009 |
| WO | WO 2009/141727 | 11/2009 |
| WO | WO 2010/014658 | 2/2010 |
| WO | WO 2010/124120 | 10/2010 |
| WO | WO 2011/094367 | 8/2011 |
| WO | WO 2012/145300 | 10/2012 |
| WO | WO 2012/145304 | 10/2012 |
| WO | WO 2013/028781 | 2/2013 |
| WO | WO 2013/112844 | 8/2013 |
| WO | WO 2013/159066 | 10/2013 |
| WO | WO 2014/070558 | 5/2014 |
| WO | WO 2015/061614 | 4/2015 |
| WO | WO 2015/168314 | 11/2015 |
| WO | WO 2019/195625 | 10/2019 |

OTHER PUBLICATIONS

U.S. Appl. No. 15/947,460, filed Apr. 6, 2018, Fischell et al.
U.S. Appl. No. 15/947,618, filed Apr. 6, 2018, Fischell et al.
U.S. Appl. No. 15/947,619, filed Apr. 6, 2018, Fischell et al.
U.S. Appl. No. 15/947,626, filed Apr. 6, 2018, Fischell et al.
U.S. Appl. No. 16/034,854, filed Jul. 13, 2018, Fischell et al.
U.S. Appl. No. 16/039,234, filed Jul. 18, 2018, Fischell et al.
U.S. Appl. No. 16/238,780, filed Jan. 3, 2019, Fischell et al.
U.S. Appl. No. 16/296,688, filed Mar. 8, 2019, Fischell et al.
Angelini et al., Retractable-Needle Catheters: An Updated on Local Drug Delivery in Coronary Interventions, Texas Heart Institute Journal, 2008, p. 419-424.
Bello-Reuss et al., Effects of Acute Unilateral Renal Denervation in the Rat, J. of Clinical Investigation, vol. 56, Jul. 1975, p. 208-217.
Berne, Hemodynamics and Sodium Excretion of Denervated Kidney in Anesthetized and Unanesthetized Dog, Am. J. of Physiology, vol. 171, No. 1, Oct. 1952, p. 148-158.
Chinushi et al., "Blood Pressure and Autonomic Responses to Electrical Stimulation of the Renal Arterial Nerves Before and After Ablation of the Renal Artery", Hypertension, 2013, vol. 61, p. 450-456.
Dave, R.M., "The ClearWay™ RX Local Therapeutic Infusion Catheter", CathLab Digest, May 2010, vol. 18, No. 5, p. 1-6.
Demas et al., Novel method for localized, functional sympathetic nervous system denervation of peripheral tissue using guanethidine (Journal of Neuroscience Methods 112, 2001), p. 21-28.
Dorward et al., "Reflex Responses To Baroreceptor, Chemoreceptor and Nociceptor Inputs in Single Renal Sympathetic Neurons in the Rabbit and the Effects of Anaesthesia on Them", Journal of the Autonomic Nervous System, 1987, vol. 18, p. 39-54.

(56) References Cited

OTHER PUBLICATIONS

F Mahoud, C Ukena, RE Schmieder. Ambulatory Blood Pressure Changes After Renal Sympathetic Denervation in Patients With Resistant Hypertension. Jul. 8, 2013 AHA Circulation 2013;128:132-140.

Gado et al., "Intra-articular guanethidine injection for resistant shoulder pain: a preliminary double blind study of a novel approach" Annals of the Rheumatic Disease, 1996, p. 199-201.

Habara et al., "Novel Use of a Local Drug Delivery Catheter for Coronary Perforation", Journal of Invasive Cardiology, Jan. 2011, vol. 23, No. 1, p. 1-8.

Hamza et al., "Substantial Reduction in Single Sympathetic Nerve Firing After Renal Denervation in Patients With Resistant Hypertension", Nov. 19, 2012, p. 856-864.

Hsu et al., "The Use of Intravenous Guanethidine Block in the Management of Reflex Sympathtic Dystrophy Syndrome of the Hand." Second Congress of the Hong Kong Orthopaedic Association, Nov. 1982, p. 93-105.

Hering et al., "Substantial Reduction in Single Sympathetic Nerve Firing After Renal Denervation in Patients With Resistant Hypertension", Nov. 19, 2012 in 15 pages.

Klein et al. "Functional reinnervation and development of super-sensitivity to NE after renal denervation in rats" American Physiological Society, 1980, p. 353-358.

Klein et al., Effect of Renal Denervation on Arterial Pressure and Renal Norepinephrine Concentration in Wistar-Kyota and Spontaneously Hypersensitive Rats, Can. J. Physiology and Pharmacology, vol. 58, 1980, p. 1384-1388.

Markovic, B., et al., "Embolization With Absolute Ethanol Injection of Insufficiently Ligated Renal Artery After Open Nephrectomy"; Diagnostic and Interventional Radiology, Mar. 2011; vol. 17, Issue 1, p. 88-91.

"Multi-prong Infusion Needle Case Study", from the web site of peridot™ Precision Manufacturing, http://www.peridotcorp.com/casestudy.aspx, Copyright 2012, in 8 pages.

Nanni et al., Control of Hypertension by Ethanol Renal Ablation (Radiology 148:51-54, Jul. 1983), p. 52-54.

National Institute for Health and Care Excellence. Hypertension in adults: diagnosis and management. Aug. 24, 2011, NICE, CG127.

Owens et al., Percutaneous Peri-Adventitial Guanethidine Delivery Induces Renal Artery Sympathectomy: Preclinical Experience and Implication for Refractory Hypertension (Journal of Vascular Surgery 53:17S), p. 87S, Jun. 2011.

Roytta et al., Taxol-induced neuropathy: short-term effects of local injection (Journal of Neurocytology 13, 1984), p. 685-701.

S.J .Doletskiy et al. "Vysokochastotnaj Elektrotekhnika", M., 7-10 "MEDITSINA", 1980, p. 48-50, fig. 18-19.

Trostel et al., Do renal nerves chronically influence renal function and arterial pressure in spinal rats? (The American Physiological Society 1992), p. 1265-1270.

Verloop et al., Eligibility for percutaneous renal denervation: the importance of a systematic screening, Journal of Hypertension, 2013, p. 1-7.

Vink et al. Limited destruction of renal nerves after catheter-based renal denervation: results of a human case study, Nephrol Dial Transplant, 2014, p. 1-3.

YA Ashram, NH Abdel Wahab, IH Diab, Non-dipping pattern of nocturnal blood pressure in obstructive sleep apnea syndrom: Possible role of oxidative stress and endothelin-1 precursor. Feb. 14, 2013, Alexandria Journal of Medicine, 49, 153-161.

Zafonte et al., "Phenol and Alcohol Blocks for the Treatment of Spasticity", Physical medicine and rehabilitation clinics of North America, Nov. 2001, p. 817-832.

International Search Report and Written Opinion in PCT/US13/66445 dated Feb. 10, 2014 in 21 pages.

International Search Report and Written Opinion in PCT/US15/02833 dated Sep. 8, 2015 in 9 pages.

Extended Search Report in EP 13850310.7 dated Jun. 27, 2016 in 11 pages.

Office Action for Chinese Patent Application 201380061965.5 dated Nov. 28, 2016 in 7 pages.

Office Action for Singapore Patent Application 11201503312S dated Jul. 18, 2017 in 5 pages.

Office Action for Japanese Patent Application 2015-539764 dated Aug. 28, 2017 in 4 pages.

Office Action for Chinese Patent Application 201380061965.5 dated Sep. 5, 2017 in 3 pages.

Office Action for Japanese Patent Application 2015-539764 dated Apr. 25, 2018 in 7 pages.

Notice of Allowance for Japanese Patent Application 2015-539764 dated Mar. 15, 2019 in 3 pages.

International Search Report and Written Opinion in PCT/US19/25907 dated Jul. 25, 2019 in 14 pages.

U.S. Appl. No. 16/945,077, filed Jul. 31, 2020, Fischell et al.
U.S. Appl. No. 17/127,151, filed Dec. 18, 2020, Fischell et al.
U.S. Appl. No. 17/127,443, filed Dec. 18, 2020, Fischell et al.
U.S. Appl. No. 17/173,536, filed Feb. 11, 2021, Fischell et al.

Office Action for Japanese Patent Application 2019-076766 dated Mar. 17, 2020 in 5 pages.

Extended Search Report in EP 20180202.2 dated Sep. 2, 2020 in 11 pages.

Office Action for Japanese Patent Application 2019-076766 dated Oct. 9, 2020 in 6 pages.

* cited by examiner

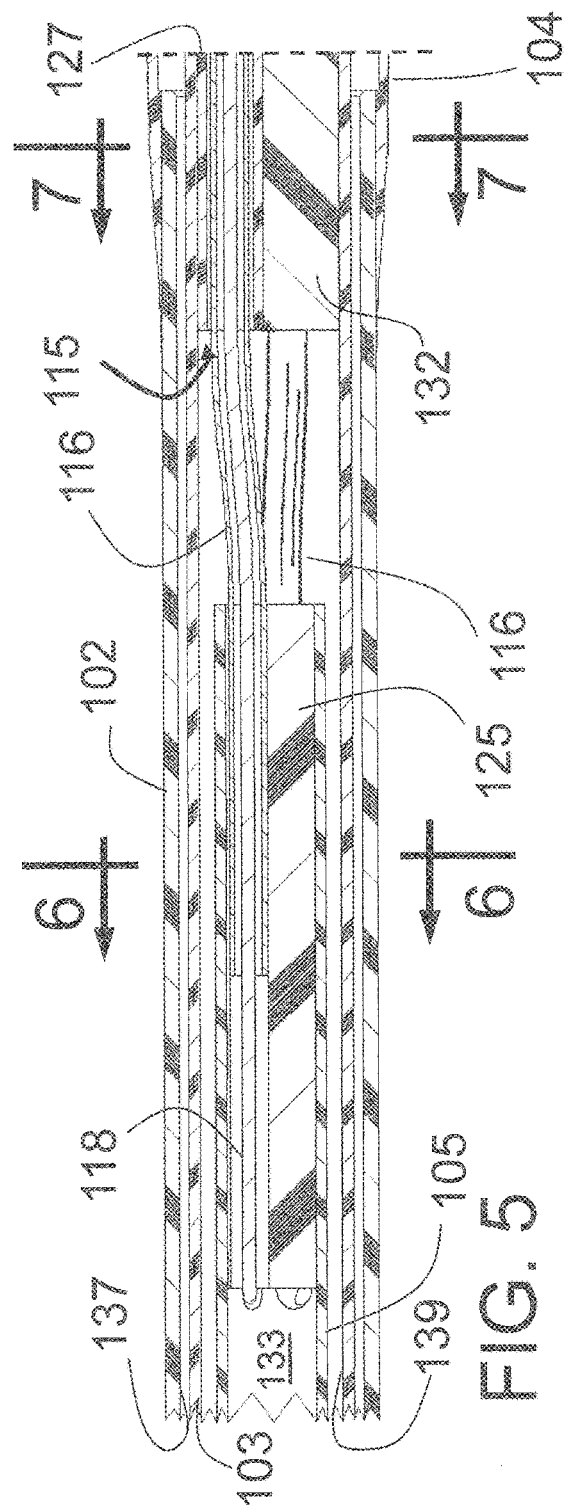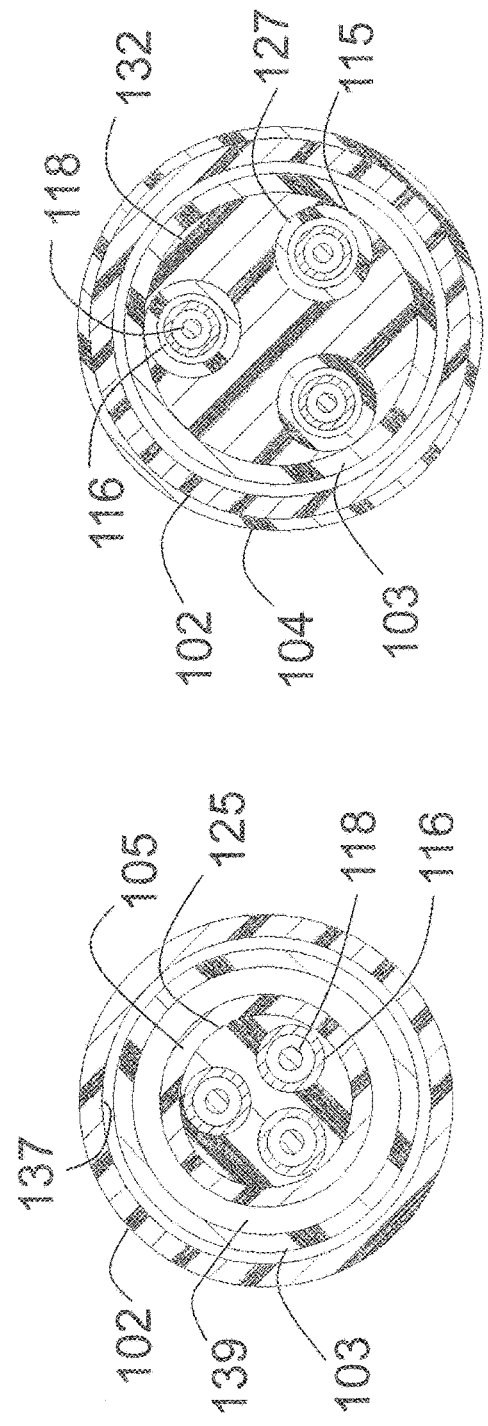

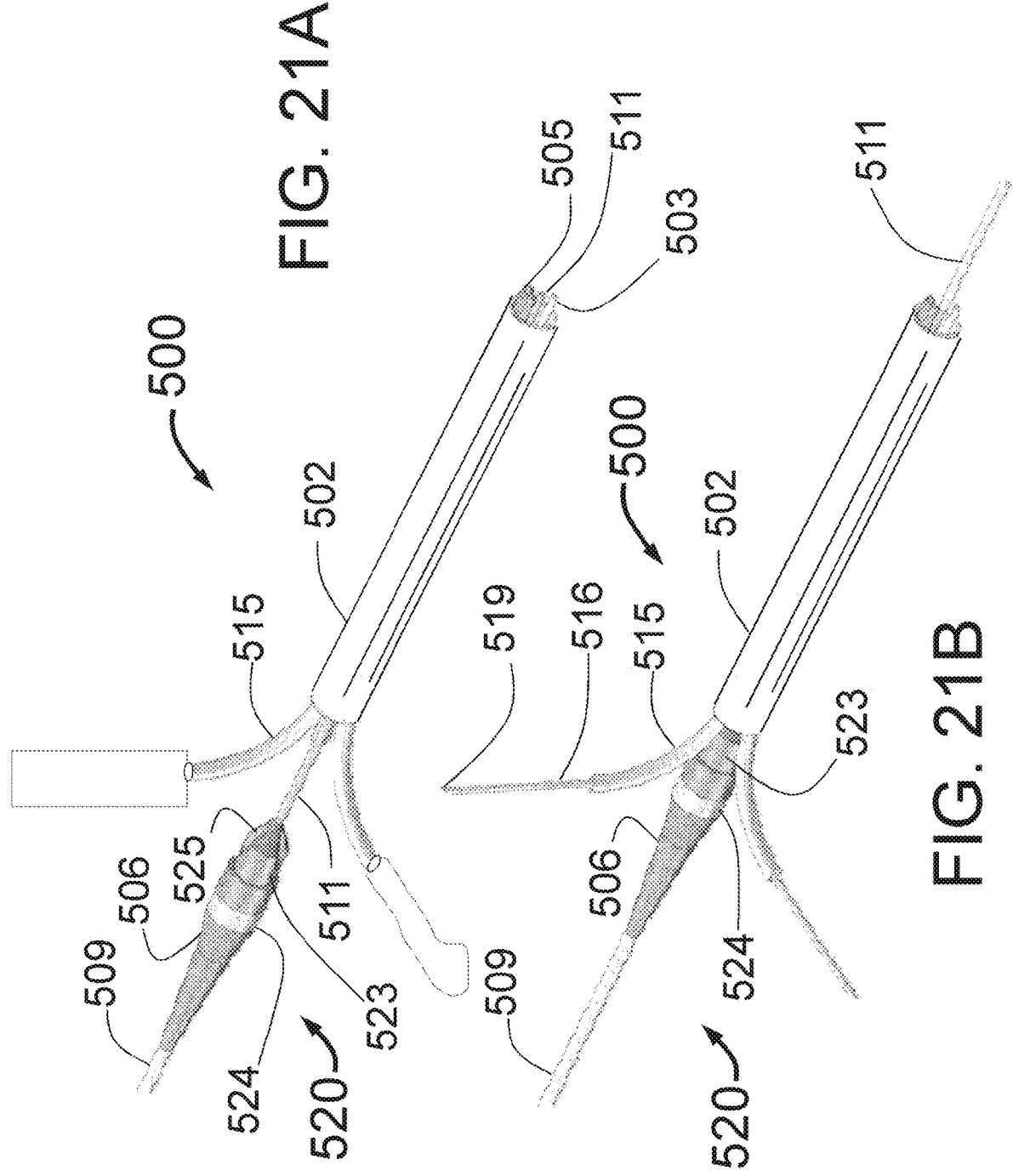

PERI-VASCULAR TISSUE ABLATION CATHETER WITH SUPPORT STRUCTURES

CROSS-REFERENCE TO RELATED APPLICATIONS

This application is a continuation of U.S. patent application Ser. No. 15/383,528, filed Dec. 19, 2016, which is a continuation of U.S. patent application Ser. No. 14/266,726, filed Apr. 30, 2014, now U.S. Pat. No. 9,526,827, which is a continuation-in-part application of U.S. patent application Ser. No. 13/752,062 filed on Jan. 28, 2013, now U.S. Pat. No. 8,740,849, which in turn is a nonprovisional application of U.S. Prov. App. No. 61/719,906 filed on Oct. 29, 2012, both U.S. patent application Ser. No. 13/752,062 and U.S. Prov. App. No. 61/719,906 hereby incorporated by reference in their entireties. Any and all applications for which a foreign or domestic priority claim is identified in the Application Data Sheet as filed with the present application, are hereby incorporated by reference in their entirety under 37 CFR 1.57.

FIELD OF THE INVENTION

This invention is in the field of devices to ablate tissue and nerve fibers for the treatment of hypertension, congestive heart failure, BPH and prostate cancer and other disorders.

BACKGROUND OF THE INVENTION

Since the 1930s it has been known that injury or ablation of the sympathetic nerves in or near the outer layers of the renal arteries can dramatically reduce high blood pressure. As far back as 1952, alcohol has been used for tissue ablation in animal experiments. Specifically Robert M. Berne in "Hemodynamics and Sodium Excretion of Denervated Kidney in Anesthetized and Unanesthetized Dog" Am J Physiol, October 1952 171:(1) 148-158, describes painting alcohol on the outside of a dog's renal artery to produce denervation.

Because of the similarities of anatomy, for the purposes of this disclosure, the term target vessel will refer here to the renal artery, for hypertension or congestive heart failure (CHF) applications and the urethra for BPH and prostate applications.

Recent technology for renal denervation include energy delivery devices using radiofrequency or ultrasound energy, such as Simplicity™ Medtronic, EnligHTN™ from St. Jude Medical which are RF ablation catheters and One Shot system from Covidien. There are potential risks using the current technologies for RF ablation to create sympathetic nerve denervation from interior the renal artery for the treatment of hypertension or congestive heart failure. The short-term complications and the long-term sequelae of applying RF energy from interior the renal artery to the wall of the artery are not well defined. This type of energy applied within the renal artery, and with transmural renal artery injury, may lead to late restenosis, thrombosis, renal artery spasm, embolization of debris into the renal parenchyma, or other problems interior the renal artery. There may also be uneven or incomplete sympathetic nerve ablation, particularly if there are anatomic anomalies, or atherosclerotic or fibrotic disease interior the renal artery, such that there is non-homogeneous delivery of RF energy This could lead to treatment failures, or the need for additional and dangerous levels of RF energy to ablate the nerves that run along the adventitial plane of the renal artery. Similar issues may also be present with the use of ultrasound.

The Simplicity™ system for RF energy delivery also does not allow for efficient circumferential ablation of the renal sympathetic nerve fibers. If circumferential RF energy were applied in a ring segment from within the renal artery (energy applied at intimal surface to kill nerves in the outer adventitial layer) this could lead to even higher risks of renal artery stenosis from the circumferential and transmural thermal injury to the intima, media and adventitia. Finally, the "burning" of the interior wall of the renal artery using RF ablation can be extremely painful. The long duration of the RF ablation renal denervation procedure requires sedation and, at times, extremely high doses of morphine or other opiates, and anesthesia close to general anesthesia, to control the severe pain associated with repeated burning of the vessel wall. Thus, there are numerous and substantial limitations of the current approach using RF-based renal sympathetic denervation. Similar limitations apply to ultrasound or other energy delivery techniques.

The Bullfrog® micro infusion catheter described by Seward et al in U.S. Pat. Nos. 6,547,803 and 7,666,163, which uses an inflatable elastic balloon to expand a single needle against the wall of a blood vessel, could be used for the injection of a chemical ablative solution such as alcohol but it would require multiple applications as those patents do not describe or anticipate the circumferential delivery of an ablative substance around the entire circumference of the vessel. The greatest number of needles shown by Seward is two and the two needle version of the Bullfrog® would be hard to miniaturize to fit through a small guiding catheter to be used in a renal artery. If only one needle is used, controlled and accurate rotation of any device at the end of a catheter is difficult at best and could be risky if the subsequent injections are not evenly spaced. This device also does not allow for a precise, controlled and adjustable depth of delivery of a neuroablative agent. This device also may have physical constraints regarding the length of the needle that can be used, thus limiting the ability to inject agents to an adequate depth, particularly in diseased renal arteries with thickened intima. Another limitation of the Bullfrog® is that inflation of a balloon within the renal artery can induce transient renal ischemia and possibly late vessel stenosis due to balloon injury of the intima and media of the artery, as well as causing endothelial cell denudation.

Jacobson and Davis in U.S. Pat. No. 6,302,870 describe a catheter for medication injection into the interior wall of a blood vessel. While Jacobson includes the concept of multiple needles expanding outward, each with a hilt to limit penetration of the needle into the wall of the vessel, his design depends on rotation of the tube having the needle at its distal end to allow it to get into an outward curving shape. The hilt design shown of a small disk attached a short distance proximal to the needle distal end has a fixed diameter which will increase the total diameter of the device by at least twice the diameter of the hilt so that if the hilt is large enough in diameter to stop penetration of the needle, it will significantly add to the diameter of the device. Using a hilt that has a greater diameter than the tube, increases the device profile, and also prevents the needle from being completely retracted back inside the tubular shaft from which it emerges, keeping the needles exposed and potentially allowing accidental needlestick injuries to occur. For either the renal denervation or atrial fibrillation application, the length of the needed catheter would make control of such rotation difficult. In addition, the hilts, which limit penetration, are a fixed distance from the distal end of the needles.

There is no built in adjustment on penetration depth, which may be important if one wishes to selectively target a specific layer in a vessel or if one needs to penetrate all the way through to the volume past the adventitia in vessels with different wall thicknesses. Jacobson also does not envision use of the injection catheter for denervation. Finally, FIG. 3 of the Jacobson patent shows a sheath over expandable needles without a guide wire and the sheath has an open distal end which makes advancement through the vascular system more difficult. Also, because of the hilts, if the needles were withdrawn completely inside of the sheath they could get stuck inside the sheath and be difficult to push out.

As early as 1980, alcohol has been shown to be effective in providing renal denervation in animal models as published by Kline et al in "Functional re-innervation and development of supersensitivity to NE after renal denervation in rats", *American Physiological Society* 1980:0363-6110/80/0000-0000801.25, pp. R353-R358. Kline states that "95% alcohol was applied to the vessels to destroy any remaining nerve fibers. Using this technique for renal denervation, we have found renal norepinephrine concentration to be over 50% depleted (i.e. <10 mg/g tissue) two weeks after the operation." Again in 1983 in the article "Effect of renal denervation on arterial pressure in rats with aortic nerve transaction" *Hypertension,* 1983, 5:468-475, Kline again publishes that a 95% alcohol solution applied during surgery is effective in ablating the nerves surrounding the renal artery in rats. Drug delivery catheters such as that by described by Jacobson which are designed to inject fluids at multiple points into the wall of an artery have existed since the 1990s.

McGuckin in U.S. Pat. No. 7,087,040 describes a tumor tissue ablation catheter having three expandable tines for injection of fluid that exit a single needle. The tines expand outward to penetrate the tissue. The McGuckin device has an open distal end that does not provide protection from inadvertent needle sticks from the sharpened tines. In addition, the McGuckin device depends on the shaped tines to be of sufficient strength so that they can expand outward and penetrate the tissue. To achieve such strength, the tines would have to be so large in diameter that severe extravascular bleeding would often occur when the tines would be retracted back following fluid injection for a renal denervation application. There also is no workable penetration limiting mechanism that will reliably set the depth of penetration of the distal opening from the tines with respect to the interior wall of the vessel, nor is there a preset adjustment for such depth. For the application of treating liver tumors, the continually adjustable depth of tine penetration may make sense since multiple injections at several depths might be needed. However, for renal denervation, the ability to accurately adjust the depth or have choice of penetration depth when choosing the device to be used is important in some embodiments so as to not infuse the ablative fluid too shallow and injure the media of the renal artery or too deep and thus miss the nerves that are in the adventitial and peri-adventitial layers of the renal artery.

Chan et al. in U.S. Pat. Nos. 7,273,469 and 8,152,758 describe a catheter assembly with a plurality of delivery cannulas, each connected to a proximal taper wall of an expandable balloon. Furthermore, there is no workable penetration limiting mechanism in Chan that will reliably set the depth of penetration of the needles with respect to the interior wall of the vessel. The Chan device includes independent injection fittings, with one for each needle, which allows each needle to be accidentally set to different depths. For catheters having a plurality of needles, with each needle having an injection fitting, the independent injection fittings will add complexity to the design and make the catheter body have a larger diameter. Further, in other embodiments, the Chan device does not place the delivery cannula flush against the inside wall of the target vessel.

Chan's delivery cannulas are fixedly attached to the outside of a balloon which only moves them outwardly. In some embodiments, the balloon of Chan has a cloverleaf design which would be difficult to manufacture. The balloon may be required to be made from a non-compliant material, which would limit the diameters usable for a single design. In some embodiments, the Chan device has a cylindrical balloon that would obstruct the blood flow in an artery if used for applications like renal denervation. In addition, many embodiments of the Chan device appear to obstruct a significant portion of the cross sectional area of the vessel lumen, which would obstruct much of, if not all of the blood flow and potentially lead to undesirable ischemia of distal tissue. Obstructing blood flow to the kidneys may be counterproductive for, e.g., renal denervation therapies for the treatment of hypertension, since maintaining adequate blood flow to the kidneys during a procedure, which in many cases are already somewhat compromised, can be important. Maintaining adequate blood flow is often important, as renal denervation may be useful for treating hypertension in chronic renal disease or dialysis patients with one or more damaged kidneys.

Although alcohol has historically been shown to be effective as a therapeutic agent for renal denervation and is indicated by the FDA for use in the ablation of nerves, there is need for an intravascular injection system specifically designed for the peri-vascular circumferential ablation of sympathetic nerve fibers in the outer layers around the renal arteries with adjustable penetration depth to accommodate variability in vessel wall thicknesses and to account for the fact that many renal artery nerves are situated at some distance outside of the artery's adventitia.

Throughout this specification any of the terms ablative fluid, ablative solution and/or ablative substance will be used interchangeably to include a liquid or a gaseous substance delivered into a volume of tissue in a human body with the intention of damaging, killing or ablating nerves or tissue within that volume of tissue. Also throughout this specification, the term inside wall or interior surface applied to a blood vessel, vessel wall, artery or arterial wall mean the same thing which is the inside surface of the vessel wall inside of which is the vessel lumen. Also the term injection egress is defined as the distal opening in a needle from which a fluid being injected will emerge. With respect to the injection needle, either injection egress or distal opening may be used here interchangeably.

The terminology "deep to" a structure is defined as beyond or outside of the structure so that "deep to the adventitia" refers to a volume of tissue outside of the adventitia of an artery.

SUMMARY OF THE INVENTION

Fischell et al. in U.S. patent application Ser. Nos. 13/216,495, 13/294,439 and 13/342,521 describe several methods of using expandable needles to deliver ablative fluid into or deep to the wall of a target vessel. Each of these applications is hereby incorporated by reference in its entirety. There are two types of embodiments of Ser. Nos. 13/216,495, 13/294,439 and 13/342,521 applications, those where the needles alone expand outward without support from any other structure and those with guide tubes that act as guiding elements to support the needles as they are advanced into the wall of a target vessel. The limitation of the needle alone designs are that if small enough needles are used to avoid blood loss following penetration through the vessel wall, then the needles may be too flimsy to reliably and uniformly expand to their desired position. The use of a cord or wire to connect the needles together in one embodiment helps some in the area. The use of guide tubes as described in the Fischell application Ser. Nos. 13/294,439 and 13/342,521 greatly improves this support, but the unsupported guide tubes themselves depend on their own shape to ensure that they expand uniformly and properly center the distal portion of the catheter. Without predictable catheter centering and guide tube expansion it may be challenging to achieve accurate and reproducible needle penetration to a targeted depth.

Another limitation of the non-supported guide tubes is the lack of radial support or "backup" as the injection needles are advanced through the guide tubes. This can result in the guide tubes being pushed away from the interior surface of the vessel wall as the needles are advanced. If the guide tubes are stiff enough to provide backup then the distal section of the catheter becomes more rigid and this may limit catheter deliverability, and may cause trauma to the wall of the vessel. If the guide tubes are fairly flexible then they can be pushed away from the wall during needle advancement, and/or be displaced radially such that the injection sites are not distributed symmetrically around the central axis of the target vessel.

The present application discloses a Peri-vascular Tissue Ablation Catheter (PTAC), that is capable of delivering an ablative fluid to produce circumferential damage in the tissue that is in the outer layer or beyond the outer layer of a vessel of a human body. The tissue and nerve ablation using this technique can be accomplished in a relatively short time as compared with RF ablation catheters, and also has the advantage of using only a disposable catheter, with no additional, externally located, capital equipment. It will also allow the use of short acting anesthetic agents like Versed, and lower doses of narcotics to reduce or eliminate patient discomfort and pain during the procedure.

The primary focus of use of PTAC is in the treatment of hypertension and congestive heart failure by renal denervation and the treatment of BPH and prostate cancer by tissue ablation of the prostate from a catheter in the urethra.

Unlike the Bullfrog or current RF ablation devices that work with one or, at most two points of ablation, the presently disclosed device is designed to provide peri-vascular fluid injection allowing a more uniform circumferential injury to the nerves or other "target" tissue, while minimizing injury to the interior layers of the vessel wall. The term "circumferential delivery" is defined here as at least three points of simultaneous injection of a suitable ablative solution within a vessel wall, or circumferential filling of the space outside of the adventitial layer (outer wall) of a blood vessel. Unlike the Jacobson device of U.S. Pat. No. 6,302,870, which does describe circumferential delivery, the disclosed device does not depend upon rotation of a tube to create outward movement nor does it have a fixed diameter hilt to limit penetration. In addition, while the Jacobson patent shows a version of his device that pulls back within a sheath like tube, the tube has an open end and the claims of the Jacobson patent require an increase in diameter to accommodate the manifold that allows the fluid flowing in one lumen from the proximal end of the catheter to egress through multiple needles. The preferred embodiment of the present application uses a manifold that fits within the lumen of the tube thus greatly decreasing the diameter of the catheter which enhances delivery of the catheter to the desired site within the human body.

Specifically, there is a definite need for such a catheter system that is capable of highly efficient, and reproducible peri-vascular ablation of the sympathetic nerves surrounding the renal artery, or tissue around a target vessel, and thus improve the control and treatment of hypertension, etc. The primary improvement of the present disclosure is the addition of support structures that improve the uniformity and symmetry of expansion of the guide tubes of the Fischell Ser. Nos. 13/294,439 and 13/342,521 applications. The support structures of the present application also support the expanded guide tubes in the radial (outward) direction to provide better backup as the needles are advanced through the guide tubes and into the wall of the target vessel.

This type of system may also have major advantages over other current technologies by allowing highly efficient, and reproducible peri-vascular circumferential ablation of the muscle fibers and conductive tissue in the wall of the pulmonary veins near or at their ostium into the left atrium of the heart. Such ablation could interrupt atrial fibrillation (AF) and other cardiac arrhythmias. The concepts of the present application could also be used to ablate prostatic tissue external to the prostatic urethra to treat benign prostatic hypertrophy (BPH) or prostate cancer. Other potential applications of this approach may also become evident from the various teachings of this patent.

Like the earlier Fischell inventions for the treatment of hypertension, the present application discloses a small diameter catheter, which includes multiple expandable injector tubes having sharpened injection needles at or near their distal ends that are advanced through guide tubes designed to support and guide the needles into and through the inner layers of the target vessel.

Some embodiments are described herein that improve upon the Fischell designs of U.S. patent application Ser. No. 13/294,439. One embodiment uses three or more manually expanded guide tubes that are advanced through tubular shafts in the distal portion of the PTAC. Each tubular shaft having a central buttress with a shape that curves outward from the longitudinal axis of the PTAC distal portion. The pre-shaped, curved guide tubes will follow the shaft and advance outward against the interior surface of the target vessel.

An advantageous feature to this design is the support (backup) provided by the central buttress and by the mass of the central catheter body that prevents the guide tubes from pushing away from the interior wall of the target vessel as the injector tubes with distal needles are advanced through the vessel wall. Specifically an outward curving central buttress support that is part of the distal section of the tubular shaft provides the above mentioned backup or support. In addition to radial support for the guide tubes, the buttress in conjunction with the openings in the distal end of the tubular shaft also support the uniform spacing and lateral stability of the guide tubes.

There is also a significant advantage of this embodiment over the Fischell Ser. No. 13/294,439 application as far as the uniformity and predictability of device centering and the enhanced control of the rate of advancement of the guide tubes to their position engaging the interior wall of the target vessel.

The embodiments shown here have significant differences and advantages over the Chan designs of U.S. Pat. Nos.

7,273,469 and 8,152,758 and other catheters known in the art. Specifically the differences and advantages may include, for example:

The guide tubes of the present application are, in some embodiments, self-expanding and move outward against the inside wall of the target vessel. The guide tubes are movable distally and proximally with respect to the distal portion of the catheter. The guide tubes are manually movable and expandable.

In some embodiments, the mechanical support for the guide tubes include central buttresses, obturators and intraluminal centering mechanisms which provide mechanical support. Unlike balloons, these mechanical supports allow much better blood flow, in some embodiments. As such, in some embodiments, the catheters, and/or mechanical support structures do not have balloons.

For blood vessel injection application of some embodiments, obstructing blood flow to the downstream tissue should be avoided. For Renal Denervation, obstructing blood flow to the kidneys is particularly contra-indicated. Many hypertensive patients have poorly functioning kidneys which are sensitive to cut off of blood flow. An important group of patients for renal denervation are end stage dialysis patients who are at much higher risk for worsening should blood flow to a kidney be reduced even for a relatively short period of time. This can also be applicable to patients with Stage 2, 3, 4, and/or 5 chronic kidney disease, or patients having a glomerular filtration rate (GFR) that is about, or less than about 60, 55, 50, 45, 40, 35, 30, 25, 20, 15, 10, or less (measured in mL/min/1.73 m$^2$). The catheter can be moved through the vessel without obstructing or substantially obstructing the blood flow through the vessel Some embodiments are designed to obscure only a portion of cross sectional area interior lumen of the target vessel (e.g., while the catheter is in a configuration delivering fluid to a lumen of the target vessel wall (e.g., obscuring less than about 70%, 65%, 60%, 55%, 50%, 45%, 40%, 35%, 30%, 25%, or less of the cross-sectional lumen of the target vessel). The target vessel can have any diameter, but in some embodiments has a diameter of between about 3 mm and about 10 mm, between about 3 mm and about 7 mm, between about 4 mm and about 6 mm, or about 3 mm, 4 mm, 5 mm, 6 mm, 7 mm, 8 mm, 9 mm, or 10 mm. In some embodiments, the target vessel has a location in which the catheter is deployed, and the cross-sectional area of the lumen of the target vessel is between about 30 mm$^2$ and about 300 mm$^2$, between about 30 mm$^2$ and about 150 mm$^2$, between about 50 mm$^2$ and about 120 mm$^2$, or about 30 mm$^2$, about 50 mm$^2$, about 80 mm$^2$, about 120 mm$^2$, about 150 mm$^2$, about 200 mm$^2$, about 250 mm$^2$, or about 300 mm$^2$. In some embodiments, a location within a target vessel having a luminal cross-section can be defined as a circle having the largest possible circumference that still is able to fit entirely within a cross-section of the lumen of the target vessel. A catheter can have one, two, three, four, or more radially outwardly extending structures, including mechanical supports, guide tubes, needles, and the like akin to sectors of the circle defining a pie chart. The structures can physically occupy, for example, sectors making up less than about 300°, 285°, 270°, 255°, 240°, 225°, 210°, 195°, 180°, 165°, 150°, 135°, 120°, 105°, 90°, 75°, 60°, 45° or less of the pie chart, leaving the remaining sectors of the pie chart advantageously unobstructed for blood to flow therethrough even when the catheter is deployed in an expanded state. This is in contrast to a balloon expanded radially in all directions, which could potentially occupy a sector made up of the entire 360° of the pie chart.

In some embodiments, a balloon supports the guide tubes. The balloon can be a cylindrical balloon, which is simple to construct as compared to more complex designs of the prior art. The cylindrical balloon does not, in some embodiments, obstruct blood flow sufficient to cause ischemia to distal organs and tissues. It can be a non-compliant balloon to ensure, even in an expanded state that there is room between the outside of the balloon and the inside wall of the target vessel for blood to flow. In some embodiments, the balloon has a maximum expanded diameter that is no more than about 90%, 85%, 80%, 75%, 70%, 65%, 60%, 55%, 50%, 45%, 40%, 35%, 30%, 25%, or less of the inside diameter of the luminal wall of the target vessel. The target vessel can have any diameter, but in some embodiments has a diameter of between about 3 mm and about 10 mm, between about 3 mm and about 7 mm, between about 4 mm and about 6 mm, or about 3 mm, 4 mm, 5 mm, 6 mm, 7 mm, 8 mm, 9 mm, or 10 mm.

In some embodiments, there is only a single injection lumen and only a single control mechanism to advance the injection needles, which makes it simpler to construct, reduces the diameter of the catheter, and can be more reliable than the prior art. The control mechanism ensures uniform depth for the needles. This is advantageous for configurations having three or more needles, for example. Other embodiments can include a plurality of injection lumens and/or control mechanisms.

The distal portion of the guiding catheter used to access the target vessel (such as the renal artery) is typically not aligned with the longitudinal axis of that vessel. Since that is the case, the presently disclosed device with a manually expanded embodiment using three guide tubes will be advantageous in several different ways. When the three guide tubes are advanced outward, one will touch the interior wall of the target vessel first and as the guide tubes are further advanced outward, this first touching guide tube will push the body of the PTAC away from the wall toward the center of the vessel until the second guide tube touches the interior wall of the target vessel. Then both touching guide tubes will push the PTAC further toward the center of the vessel until the third guide tube touches the interior wall of the vessel. Because the guide tubes here are not flimsy structures, and have each the same diameter of expansion from the longitudinal axis of the PTAC, this will reproducibly place the distal portion of the PTAC close to the true center of the vessel. Fluoroscopic imaging of the radiopaque markers on the distal portion of the guide tubes provides visual confirmation of the correct centering of the guide tubes. This centering can also be confirmed by using contrast injected from the guiding catheter, after guide tube deployment.

Another key advantage of this system is the stabilization and "backup" support of the guide tubes as the injector tubes with distal injection needles are deployed/advanced through the target vessel wall. The guide tubes, which are now engaged against the interior wall of the target vessel, are supported by the tubular shafts in the body of the PTAC. Because of this central catheter "backup," the guide tubes should remain in place as the injection needles penetrate the interior wall of the target vessel and advance distally to their preset depth of penetration. The ablative fluid can then be delivered, the needles retracted back into the guide tubes and the guide tubes and needles retracted back into the tubular shafts within the distal portion of the PTAC.

A second embodiment that improves upon the teachings of the Fischell application Ser. No. 13/294,439 utilizing a self-expanding design, utilizes guide tubes attached to an intraluminal centering mechanism (ICM). One embodiment of the ICM is an expandable wire basket like structure that opens up against the interior wall of the target vessel and improves the centering, uniform and symmetric expansion, and radial support (backup) for the guide tubes to prevent the guide tubes from pulling away from the interior wall of the target vessel as the injection needles are advanced though that wall. The ICM is particularly of value if the guide tubes with ICM are self-expanding. The ICM can also provide additional stability and backup for manually expandable guide tubes such as described in the first embodiment above. The ICM may include specific radiopaque markers to provide visualization during fluoroscopy of the state of expansion of the ICM. The ICM may also create a minimal degree of offset from the tip of the guide tubes to the vessel interior wall, in order to decrease trauma to the interior layer of the vessel wall by the guide tube tips.

In either embodiment of the presently disclosed PTAC, ablative fluid can be injected through the distal ends of the injection needles that have a distal opening (injection egress) at or near their distal ends. There is a penetration limiting mechanism as part of the PTAC so that the needles will only penetrate into or beyond the interior wall of the target vessel to a preset distance. The preferred embodiment of the penetration limiting mechanism is integrated into the proximal portion of the PTAC and may include penetration depth adjustment means. The adjustment could include markings that allow for precise depth adjustments.

Adjustment of the penetration depth by mechanisms in the proximal end of the PTAC may be either physician controlled or they could be preset during device production. In the first case, use of intravascular ultrasound or other imaging techniques could be used to identify the thickness of the renal artery at the desired site for PVRD. The clinician would then adjust the depth accordingly. It is also envisioned that the PTAC could be preset in the factory using the depth adjustment which would not be accessible to the clinician and if multiple depths are needed, different product codes would be provided that allow for different depths of penetration. For example, three depths might be available such as at least 2 mm, at least 3 mm and at least 4 mm. Another advantage of factory adjustable depth is to simplify calibration and quality production as the variation for each produced PTAC may require a final in factory adjustment of needle depth so that precise depth of penetration is provided. It is also an advantage for regulatory filings that a preset depth or depths be used during trials and for approval to limit potential error in setting the wrong depth. Finally, it is envisioned that both an internal adjustment for factory production and calibration and an externally available adjustment with depth markings could be integrated into the PTAC.

The adjustment means can be used with the presently disclosed PTAC in one of the following ways:
1. For adjustment and calibration of a preset penetration depth during device manufacturing. In this case, the device might be manufactured with several labeled calibrated preset depths.
2. For adjustment of the depth of penetration by the device operator before or during use of the PTAC. This design would include markings on the PTAC that show where the depth where the ablative fluid would be injected. This design is of particular use for BPH and prostate cancer applications where injections at a series of different depths would be desirable to allow delivery into the appropriate volume of prostate tissue.

Ideally, the injection needles should be sufficiently small so that there will be virtually no blood loss following the withdrawal of the injector tubes from the vessel wall. A major advantage of the embodiments disclosed in the present application over the embodiments taught in the Fischell Ser. No. 13/216,495 application and the Jacobson U.S. Pat. No. 6,302,870 patent is that with such small (<25 gauge) needles, self-expanding structures can be quite flimsy and not reliable to ensure accurate penetration of the vessel wall if not supported by structures like the presently disclosed guide tubes. The presently disclosed guide tubes with attached ICM offer additional advantages over the unsupported guide tubes of prior Fischell designs as described in the Ser. Nos. 13/294,439 and 13/342,521 applications. Another advantage being the reliable centering of the guide tubes in the vessel and reduced trauma where the expanded mechanism touches the interior of the vessel wall.

There are several different embodiments of the presently disclosed ICM supported guide tubes. These include:
1. An expandable structure with proximal, central and distal portions, constructed from a single tube of a memory metal such as nitinol or a spring metal. The proximal portion of the structure would be a guide tube similar to that of Fischell Ser. Nos. 13/294,439 and 13/342,521 applications which would provide a guide for the injector tubes with distal injection needles. The central and distal portions being the ICM. The central portion of the structure would have a radiopaque marker and be designed to open up to touch the interior wall of the vessel with minimal trauma. The expandable distal portion of the structure would support the guide tubes and central portion of the expandable structure facilitating reproducible expansion. A preferred embodiment of this structure provides a distal structure with enhanced flexibility. The structure here can be self-expanding or provide expansion through manipulation of an Expansion Control Mechanism (ECM) at the proximal end of the PTAC, or both where the PTAC has a self-expanding ICM and an ECM that can be used to adjust or enhance the expansion.
2. An expandable structure with proximal, central and distal portions, with a plastic guide tube having an integrated spring member, the spring member extending distally from the distal end of the guide tube to form the ICM. The guide tube like those of the Fischell Ser. Nos. 13/294,439 and 13/342,521 applications providing a guide for the injector tubes with distal injection needles. The central portion of the structure would have a radiopaque marker and be designed to open up to touch the interior wall of the vessel with minimal trauma. The expandable distal portion of the structure would support the guide tubes and central portion of the expandable structure facilitating reproducible expansion. The structure here can be self-expanding or provide expansion through manipulation of an Expansion Control Mechanism (ECM) at the proximal end of the PTAC, or both where the PTAC has a self-expanding ICM and an ECM that can be used to adjust or enhance the expansion.

3. Expandable guide tubes like those of the Fischell Ser. Nos. 13/294,439 and 13/342,521 applications providing a guide for the injector tubes with distal injection needles. The guide tubes attached to an ICM formed by an expandable balloon, inflated through a lumen in the shaft of the PTAC.

The injector tubes with distal injection needles of the presently disclosed embodiments would typically have a preset curved shape with a radius of curvature similar to that of the guide tubes. Thus as the injector tubes are advanced through the guide tubes they will follow the guide tube curve and not cause the guide tubes to change position with respect to the interior wall of the target vessel. The radius of curvature of the distal portion of the guide tubes and the distal portion of the injector tubes should be within plus or minus 25% of each other and ideally within plus or minus 10%.

The embodiments of the present application will function in vessels of different diameters as the expanded shape of the guide tubes will be set so that, without the constraint of the interior wall of the vessel, they would achieve an expanded diameter slightly larger than the biggest vessel diameter envisioned for device use. It is also a feature of the embodiments of the present application that the injector tubes curve backward in the proximal direction as they extend from the distal end of the guide tubes and penetrate through the vessel wall.

Because precise depth penetration is preferred, the tubing used for any of the PTAC proximal or distal sections should have limited stretchability so they do not elongate during deployment through a guiding catheter into the renal artery. For example, stainless steel, L605 or nitinol hypotubes could be the best material for the proximal tubular sections of the PTAC. Alternately, metal reinforced tubing or high durometer plastic with reduced elongation tendencies could be used. Such tubing would also be suitable for the distal section of the PTAC where more flexibility is needed to go around the nearly right angle bend in the guiding catheter as it enters the renal artery from the aorta.

The injector tubes with distal needles are in fluid communication with an injection lumen in the catheter body, which is in fluid communication with an injection port at the proximal end of the PTAC. Such an injection port would typically include a standard connector such as a Luer connector used to connect to a source of ablative fluid. Also envisioned and described herein is the use of a customized (proximal) fitting (different from a Luer fitting) for the injection port that can improve safety by disallowing the accidental injection of fluid from a standard syringe, and also to minimize dead space within the catheter when injecting ablative agents.

This injection system also anticipates the use of very small gauge needles (smaller than 25 gauge) to penetrate the arterial wall, such that the needle penetration could be safe, even if targeted to a volume of tissue that is or beyond the adventitial layer of the aorta, a pulmonary vein or renal artery, or prostatic urethra. It is also anticipated that the distal needle could be a cutting needle or a coring needle and with a cutting needle the injection egress/distal opening ports could be small injection holes (pores) cut into the sides of the injector tubes or distal needle, proximal to the cutting needle tip. There should be at least 2 injector tubes but 3 to 8 tubes may be more appropriate, depending on the diameter of the vessel to be treated and the ability of the injected ablative fluid to spread within the peri-vascular space. For example, in a 5 mm diameter renal artery, only 3 or 4 needles may be needed while in an 8 mm diameter renal, one might need 5 to 6 needles.

Some embodiments of the present disclosure would use ethanol as the ablative fluid because this fluid is agrophobic, lipophilic, and spreads quickly in the peri-vascular space. Therefore, only 3 needles are needed to create circumferential delivery of this ablative agent, which allows one to use a smaller diameter device. It is also envisioned that use of ethanol or another alcohol plus another neurotoxic agent could also enhance the spread of the ablative agent in the peri-vascular space.

A self-expanding embodiment of the presently disclosed PTAC would typically include a tubular, thin-walled sheath that constrains the guide tubes and ICM prior to deployment, during transition from treating one renal artery to the other, and during removal from the body. The sheath also allows the distal end of the PTAC to be easily inserted into the proximal end of a guiding catheter or introducer sheath. The sheath also serves to protect the operator(s) from possible needle sticks and exposure to blood borne pathogens at the end of the procedure when the PTAC is removed from the patient's body. The sheath would typically include a radiopaque marker near its distal end to allow the operator to know its position under fluoroscopy.

The entire PTAC is designed to include a fixed distal guide wire or be advanced over a guide wire in either an over-the-wire configuration where the guide wire lumen runs the entire length of the PTAC or a rapid exchange configuration where the guide wire exits the catheter body at least 10 cm proximal to the distal end of the PTAC and runs outside of the catheter shaft for its proximal section. It is also envisioned that one could use a soft and tapered distal tip, even without a distal guidewire, for some applications.

The fixed wire version, or the version with the soft tapered distal tip without a guidewire are the preferred embodiments, as they would have the smallest distal diameter. Just proximal to the fixed wire is a tapered distal portion of the PTAC which can be called an obturator. The obturator serves several purposes in the design of the PTAC.

1. It provides a tapered flexible member that expands in diameter from the thin fixed distal guide wire to allow the PTAC to better track around bends such as the bend in the guiding catheter from the aorta into and through the ostium of the renal artery.
2. The proximal portion of the obturator mates with the sheath described above to completely surround and constrain the expandable portions of the PTAC system including guide tubes and ICM with injection needles.
3. The obturator would typically include a radiopaque marker that would allow the operator to visualize the position of the obturator as well as its position with respect to the sheath.
4. It is envisioned that the obturator could be tapered and soft such that even without a fixed distal guidewire the advancement of the device could be safely performed for certain applications, including in renal denervation.

Fluoroscopic visualization of the correct deployment of the guide tubes and injection needles are highly desirable. There are several ways that this goal could be accomplished. It is envisioned that the injection needles, guiding tubes and injection tubes could be formed from a radiopaque material such as tantalum or tungsten or coated, or marked with a radiopaque material such as gold or platinum so as to make them clearly visible using fluoroscopy. The preferred method however is to place radiopaque marker bands near the distal ends of each guide tube and include a radiopaque wire within the lumen of each injector tube. In addition to providing better visibility, the radiopaque wire in the lumen of each injector tube reduces the internal volume or dead space within the injector tube thereby reducing the amount of fluid needed to flush the internal volume of the PTAC.

It is also envisioned that one or more of the injector needles could be electrically connected to the proximal end of the PTAC so as to also act as a diagnostic electrode(s) for evaluation of the electrical activity in the area of the vessel wall.

It is also envisioned that one could attach two or more of the expandable legs to an electrical or RF source to deliver electric current or RF energy to perform tissue and/or nerve ablation.

It is also envisioned that this device could utilize one, or more than one neuroablative substances to be injected simultaneously, or in a sequence of injections, in order to optimize permanent sympathetic nerve disruption in a segment of the renal artery (neurotmesis). The anticipated neurotoxic agents that could be utilized includes but is not limited to ethanol, phenol, glycerol, local anesthetics in relatively high concentration (e.g., lidocaine, or other agents such as bupivacaine, tetracaine, benzocaine, etc.), anti-arrhythmic drugs that have neurotoxicity, botulinum toxin, digoxin or other cardiac glycosides, guanethidine, heated fluids including heated saline, hypertonic saline, hypotonic fluids, KCl or heated neuroablative substances such as those listed above.

It is also envisioned that the ablative substance can be hypertonic fluids such as hypertonic saline (extra salt) or hypotonic fluids such as distilled water. These will cause permanent damage to the nerves and could be equally as good as alcohol or specific neurotoxins. These can also be injected hot or cold or at room temperature. The use of distilled water, hypotonic saline or hypertonic saline with an injection volume of less than 1 ml eliminates one step in the use of the PTAC because small volumes of these fluids should not be harmful to the kidney and so the need to completely flush the ablative fluid from the PTAC with normal saline to prevent any of the ablative fluid getting into the renal artery during catheter withdrawal is no longer needed. This means there would be only one fluid injection step per artery instead of two if a more toxic ablative fluid is used.

It is also envisioned that the PTAC catheter could be connected to a heated fluid or steam source to deliver high temperature fluids to ablate or injure the target tissue or nerves. The heated fluid could be normal saline, hypertonic fluid, hypotonic fluid alcohol, phenol, lidocaine, or some other combination of fluids. Injection of hot or vaporized normal saline, hypertonic saline, hypotonic saline, ethanol, distilled water or other fluids via the needles could also be performed in order to achieve thermal ablation of target tissue or nerves at and around the needle injection sites.

The present disclosure also envisions use of anesthetic agents such as lidocaine which if injected first or in or together with an ablative solution can reduce or eliminate any pain associated with the denervation procedure.

It is also envisioned that one could utilize imaging techniques such as multislice CT scan, MRI, intravascular ultrasound (IVUS) or optical coherence tomography (OCT) imaging to get an exact measurement of the thickness and anatomy of the target vessel wall (e.g., the renal artery) such that one could know and set the exact and correct penetration depth for the injection of the ablative agent prior to the advancement of the injector needles or injector tubes. The use of IVUS prior to use of the PTAC may be particularly useful in order to target the exact depth intended for injection. This exact depth can then be targeted using the adjustable depth of penetration feature or by selection of an appropriate PTAC having a preset depth for the delivery of the ablative fluid. In production, different product codes would be made available with package labeling according to the penetration depth.

For use in renal sympathetic nerve ablation, the present preferred manually expandable ("push") guide tube embodiment of the PTAC would be used with the following steps (although not every step is essential and steps may be simplified or modified as will be appreciated by those of skill in the art):

1. Sedate the patient using standard techniques for cardiac catheterization or septal ablation, for example—in a manner similar to an alcohol septal ablation, (Versed and narcotic analgesic).
2. Engage a first renal artery with a guiding catheter placed through the femoral or radial artery using standard arterial access methods.
3. After flushing all lumens of the PTAC, including the injection lumen, with saline, advance the distal end of the PTAC with a fixed distal guidewire position into the guiding catheter. Advance the distal portion of the PTAC through and beyond the distal end of the guiding catheter, until the radiopaque marker on the obturator or guide tubes are at the desired location in the renal artery.
4. Manually advance the guide tubes out of their tubular shafts using the mechanism in the proximal section of the PTAC until they are fully expanded against the interior wall of the target vessel. Expansion can be confirmed by visualization of the radiopaque tips of the guide tubes.
5. Next, the injection tubes/needles are advanced coaxially through the guide tubes to penetrate through the internal elastic lamina (IEL) and media of the artery, then through the external elastic lamina (EEL) to a preset distance (typically between 0.5 to 4 mm but preferably about 2-4 mm) beyond the IEL into the outer (adventitial and/or peri-adventitial) layer(s) of the vessel wall of the renal artery. The injection tubes/needles are thereby positioned to deliver the neuroablative agent(s) at or "deep to" (outside of) the adventitial plane. The depth of 2-4 mm deep relative to the IEL will minimize intimal and medial renal artery injury. The normal thickness of the media in a renal artery is between 0.5 and 0.8 mm. The depth limitation feature of the embodiments disclosed in the present disclosure has the distal opening of the needles set to be a fixed distance beyond the distal end of the guide tubes. In a normal renal artery the guide tubes would be positioned against the IEL which is normally situated at or near the interior wall of the target vessel. If there is intimal thickening from plaque or neointimal hyperplasia within the artery as seen by angiography, IVUS or OCT, then as much as 3-6 mm of penetration depth beyond the end of the end of the guide tube may be needed. Specific product codes (e.g., preset designs) with preset greater penetration depths or user available adjustments in the handle of the PTAC are envisioned to facilitate this. If the vessel has a stenosis, it would be preferable to pick the site for needle penetration away from the stenosis and to treat the stenosis as needed with Percutaneous Coronary Intervention (PCI).
6. Inject an appropriate volume of the ablative agent which can be an ablative fluid, such as ethanol (ethyl alcohol), distilled water, hypertonic saline, hypotonic saline, phenol, glycerol, lidocaine, bupivacaine, tetracaine, benzocaine, guanethidine, botulinum toxin, glycosides or any other appropriate neurotoxic fluid. This could include a combination of 2 or more neuroablative fluids or local anesthetic agents together or in sequence (local anesthetic first to diminish discomfort, followed by delivery of the ablative agent) and/or high temperature fluids (or steam), or extremely cold (cryoablative) fluid into the vessel wall and/or the volume just outside of the vessel. A typical injection would be 0.1-3.0 ml. This should produce a multiplicity of ablation zones (one for each injector tube/needle) that will intersect to form an ablative ring around the circumference of the target vessel. Contrast could be added to the injection either during a test injection before the neuroablative agent or during the therapeutic injection to allow x-ray visualization of the ablation zone. With ethanol, as an ablative agent, a volume of less than 0.5 ml is sufficient for this infusion as it will not only completely fill the needed volume including the sympathetic nerves, but is small enough that if accidentally discharged into the renal artery, would not harm the patient's kidneys. Ideally, a volume of 0.1 ml to 0.3 ml of ethanol should be used.

7. Inject normal saline solution into the PTAC sufficient to completely flush the ablative agent out of the injection lumen(s) (dead space) of the PTAC including the injector tubes with distal injection needles. This prevents any of the ablative agent from accidentally getting into the renal artery during the withdrawal of the needles into the PTAC. Such accidental discharge into the renal artery could cause damage to the kidneys. This step may be avoided if distilled water, hypotonic or hypertonic saline is used as the ablative agent or if the volume of ablative agent is small enough such that the potential for kidney damage by accidental discharge into the renal artery is reduced. It is also envisioned that with ethanol, where less than 0.5 ml is needed for ablation, that flushing may be unnecessary as 0.5 ml in the presence of normal blood flow will not harm the kidneys.
8. Retract the PTAC injector tubes/needles back inside the guide tubes.
9. Retract the guide tubes back into the tubular shafts of the PTAC.
10. In some cases, one could rotate the PTAC 30-90 degrees, or relocate the PTAC 0.2 to 4 cm distal or proximal to the first injection site and then repeat the injection if needed to make a second ring of tissue damage to create even greater denervation/nerve ablation.
11. The same methods as per prior steps can be repeated to ablate tissue in the opposite (contra-lateral) renal artery.
12. Remove the PTAC from the guiding catheter completely.
13. Remove all remaining apparatus from the body.

A simplified version of the prior procedure avoids the use of saline flushes for the catheter injection lumen/dead space as follows:

1. Sedate the patient using standard techniques for cardiac catheterization or septal ablation, for example—in a manner similar to an alcohol septal ablation, (Versed and narcotic analgesic).
2. Engage a first renal artery with a guiding catheter placed through the femoral or radial artery using standard arterial access methods with the distal end of the guiding catheter being situated beyond the ostium of the renal artery.
3. Outside of the body, with the needle guiding elements/guide tubes and needles fully expanded, flush the injection lumen with the ablative fluid.
4. Outside of the body, flush all lumens of the PTAC except the injection lumen with saline. With enough saline flowing through the guide tubes and catheter distal openings, this should wash any residual ablative fluid off of the outer surfaces of the PTAC.
5. Retract the needles and needle guiding elements/guide tubes.
6. Advance the PTAC through the guiding catheter to the desired spot in the renal artery.
7. Manually advance the needle guiding elements/guide tubes
8. Next, advance the injection tubes/needles to penetrate through the internal elastic lamina (IEL) to the desired depth.
9. Inject an appropriate volume of the ablative agent/fluid.
10. Retract the PTAC injector tubes/needles back inside the guide tubes.
11. Retract the guide tubes back into the tubular shafts of the PTAC.
12. Retract the PTAC back into the guiding catheter.
13. If desired, move the guiding catheter to the opposite (contra-lateral) renal artery.
14. Repeat steps 6 through 11.
15. Remove the PTAC from the guiding catheter completely.
16. Remove all remaining apparatus from the body.

This simplified procedure should be safe because the amount of ablative fluid that can leak out of the retracted injection needles is significantly less than the dead space in the PTAC. Specifically, while as much as 0.5 ml of many ablative fluids such as ethanol can be safely injected into the renal artery without causing kidney damage, even if the entire internal volume were to leak out into the renal artery, because the dead space is less than 0.3 ml, it would not harm the kidney. In the real world, less than 10% of the internal volume (e.g., less than 0.03 ml) can ever leak out of the closed PTAC so the simplified procedure above should be safe.

For use in renal sympathetic nerve ablation, the embodiment of the presently disclosed PTAC with ICM would be used with the following steps (although not every step is essential and steps may be simplified or modified as will be appreciated by those of skill in the art):

1. Sedate the patient using standard techniques for cardiac catheterization or septal ablation, for example—in a manner similar to an alcohol septal ablation, (Versed and narcotic analgesic).
2. Engage a first renal artery with a guiding catheter placed through the femoral or radial artery using standard arterial access methods.
3. After flushing all lumens of the PTAC, including the injection lumen, with saline, advance the distal end of the PTAC in its closed position into the guiding catheter. Advance the distal portion of the PTAC through and beyond the distal end of the guiding catheter, until the radiopaque marker on the ICM or guide tubes are at the desired location in the renal artery.
4. Pull back the sheath allowing the expandable guide tubes with ICM to open up against the interior wall of the renal artery. If the ICM is self-expanding this will happen automatically, if the expansion is controlled by a proximal expansion control mechanism (ECM), then the ECM can be manipulated by the operator to cause expansion of the ICM and guide tubes. Expansions can be confirmed by visualization of the radiopaque tips of the guide tubes and/or the radiopaque markers on the ICM.

5. Next, the injection tubes/needles are advanced coaxially through the guide tubes to penetrate through the internal elastic lamina (IEL) at a preset distance (typically between 0.5 to 4 mm but preferably about 2-4 mm) beyond the IEL into the outer (adventitial and/or peri-adventitial) layer(s) of the vessel wall of the renal artery to deliver the neuroablative agent(s) at or deep to the adventitial plane. The depth of 2-4 mm deep relative to the IEL will minimize intimal and medial renal artery injury.

6. Inject an appropriate volume of the ablative agent which can be an ablative fluid, such as ethanol (ethyl alcohol), distilled water, hypertonic saline, hypotonic saline, phenol, glycerol, lidocaine, bupivacaine, tetracaine, benzocaine, guanethidine, botulinum toxin, glycosides or other appropriate neurotoxic fluid. This could include a combination of 2 or more neuroablative fluids or local anesthetic agents together or in sequence (local anesthetic first to diminish discomfort, followed by delivery of the ablative agent) and/or high temperature fluids (or steam), or extremely cold (cryoablative) fluid into the vessel wall and/or the volume just outside of the vessel. A typical injection would be 0.1-5 ml. This should produce a multiplicity of ablation zones (one for each injector tube/needles) that will intersect to form an ablative ring around the circumference of the target vessel. Contrast could be added to the injection either during a test injection before the neuroablative agent or during the therapeutic injection to allow x-ray visualization of the ablation zone. With ethanol, as an ablative agent, a volume of less than 0.5 ml is sufficient for this infusion as it will not only completely fill the needed volume including the sympathetic nerves, but is small enough that if accidentally discharged into the renal artery, would not harm the patient's kidneys. Ideally, a volume of 0.1 ml to 0.3 ml of ethanol should be used.

7. Inject normal saline solution into the PTAC sufficient to completely flush the ablative agent out of the injection lumen(s) (dead space) of the PTAC including the injector tubes with distal injection needles. This prevents any of the ablative agent from accidentally getting into the renal artery during pull back of the needles into the PTAC. Such accidental discharge into the renal artery could cause damage to the kidneys. This step may be avoided if distilled water, hypotonic or hypertonic saline is used as the ablative agent or the volume of ablative agent is small enough that the potential for kidney damage by accidental discharge into the renal artery is reduced.

8. Retract the PTAC injector tubes/needles back inside the guide tubes. Then, retract and re-sheath the guide tubes with ICM back under the sheath completely surrounding the sharpened needles. The entire PTAC can then be pulled back into the guiding catheter.

9. In some cases, one could rotate the PTAC 30-90 degrees, or relocate the PTAC 0.2 to 4 cm distal or proximal to the first injection site and then repeat the injection if needed to make a second ring of tissue damage to create even greater denervation/nerve ablation.

10. The same methods as per prior steps can be repeated to ablate tissue in the contra-lateral renal artery.

11. Remove the PTAC from the guiding catheter completely.

12. Remove all remaining apparatus from the body.

In both embodiments of the present application, as described in the methods above, the means to limit needle penetration of the vessel wall is included in the proximal portion of the PTAC. A handle or handles are envisioned that would be used by the operator to cause first the expansion of the guide tubes and second the advancement of the injection needles. The reverse motion of these mechanisms would then retract the needles back into the guide tubes and then retract the guide tubes back into the catheter body or under a sheath. Fischell et al in U.S. patent application Ser. Nos. 13/643,070, 13/643,066 and 13/643,065 describes such control mechanisms for advancing and retracting distal structures such as sheaths, guide tubes and injector tubes with distal injection needles. Interlocks and locking mechanisms to prevent accidental movement out of sequence of these mechanisms are also described.

Similarly, Fischell et al describes the proximal section with ports for flushing and ablative fluid injection. The embodiments disclosed in the present application would have similar structures and controls in the proximal section. The mid-section of the catheter would typically be three concentric tubes. In the manually expandable embodiment with tubular shafts, there is an outer tube that forms the main body of the catheter. A middle tube controls the advancement and retraction of the guide tubes and an inner tube controls the advancement and retraction of the injector tubes with distal injection needles. The lumen of the inner tube is also the lumen that carries the ablative fluid injected in the injection port in the proximal section of the PTAC to the lumens of the injector tubes and injection needles and finally out though the distal opening at or near the distal ends of the injection needles.

Another advantageous feature of the presently disclosed PTAC is a design that reduces the internal volume of the PTAC (the "dead space") to minimize the amount of saline needed to flush the ablative fluid out of the catheter into the desired volume of tissue. It is anticipated that less than 0.5 ml of an ablative fluid such as ethanol will be needed to perform PVRD. The dead space should be less than 0.5 ml and ideally less than 0.2 ml. With certain design features it is conceived that the dead space can be reduced to less than 0.1 ml. Such features include using a small diameter <0.5 mm ID hypotube for the inner tube used for fluid injection for the PTAC, including a wire placed into the full length of the hypotube/inner tube to reduce the volume of the hypotube and thus reduce the PTAC dead space and/or designing the proximal injection port and or injection manifold at the proximal end of the PTAC to have low volume by having small <0.5 mm inner diameter and a short, <2 cm length.

It is a feature of some embodiments of this invention that the guide tubes are needle guiding elements for the advanceable, ultra-thin injection needles. Specifically, prior art such as Jacobson that describes curved needles that are advanced outward from a central catheter to penetrate the interior wall of a target vessel, have bare needles that are advanced on their own from the distal end or the side of a catheter. Without additional guiding (support) during advancement, needles that are thin enough to not cause blood loss following withdrawal from the wall of the artery are generally too flimsy to reliably penetrate as desired into the vessel wall. Thus it is envisioned that a key aspect of the embodiments disclosed in the present application is the inclusion of needle guiding elements such as guide tubes that allow the ultra-thin injection needles to be reliably advanced into the wall of a target vessel to the desired depth. Such guiding elements need not be a tube or have a round cross-section, they could be a half or partial tube, they can be a structure with a slot that provides a guide for the advance-able needles, and a guiding structure could be any expandable structure such as a spring that expands outward and provides radial support and a guide for the needles. The terms "expand" and "expands" are intended to refer to motion of a structure from a first position relatively closer to a longitudinal axis of the catheter to at least a second position that is relatively farther away from the longitudinal axis, whether the motion is by expansion, deflection, pivoting, or other mechanism. It is desirable that the needle guiding elements expand outward from the central catheter.

What is also unique about some of the embodiments disclosed in the present application is the use of additional structures to provide radial and lateral support for the needle guiding elements. This is important, in some cases, because one needs a uniform penetration and angular spread of the multiple needles. In addition, as the needles are advanced, and guided by a "guiding element," (e.g., the guide tube) the guiding element can, if unsupported, back away from the desired position against the interior wall of the vessel. For this reason, the present disclosure teaches the design of structures that provide radial ("backup") support for the needle guiding elements that provide resistance to the guiding elements backing away from the interior surface as the needles are advanced into the wall of the vessel.

Another embodiment of the present disclosure simplifies the construction by combining the guide tube and injector tube into a single injector tube. This also reduces the steps of operation. Specifically, the injector needle is permanently attached inside the injector tube which is advanced and retracted through the tubular shaft. The distal end of the injector tube is of larger diameter than the injector needle and provides the "stop" that limits the penetration of the injector needle into the wall of the target vessel.

Yet another embodiment of the present disclosure uses an inflatable balloon to expand the guide tubes through which the injector tubes with distal needles are advanced into the wall of the target vessel. The balloon may be compliant, semi-compliant or non-compliant. However, an elastic compliant balloon is preferred as it would allow the diameter of the outer edges of the expanded guide tubes to be easily set by using different inflation pressures for the balloon. Attaching the guide tubes to the outside of the balloon simplifies construction as compared with attempting to place guide tubes within the balloon and also allows the distal end of the guide tubes to be the points of engagement with the interior wall of the target vessel so that the external surface of the balloon does not touch the wall. Having the balloon touch the wall can remove the endothelial cells and produce neointimal hyperplasia which is undesirable. The balloon expandable embodiment may have the guide tubes and injector tubes combined where the balloon expansion causes the needles to expand outward to penetrate the wall. The balloon expandable embodiments may also use an optional sheath to enclose the expandable distal portion to facilitate delivery and reduce the chance of needlestick injuries during handling, insertion and removal of the catheter. Having the guide tubes or injector tubes attached to the outside of an expandable elastic balloon will also provide radial and lateral stability for the thin needles to ensure both uniform expansion and backup as the needles are advanced through the wall of the target vessel.

Another feature of the embodiments of the present application is to have the injection port for injecting the ablative fluid would be a non-standard fitting with a small diameter lumen. In addition, the present application envisions matching syringes that would have the mate for the non-standard fitting of the injection port. Such a syringe could contain the appropriate volume for injection of fluids into the wall of the target vessel including ablative fluids or a saline solution used to flush the injector tubes prior to insertion of the PTAC into the vessel to be treated.

Another feature of the PTAC disclosed in the present application is that the flow though the multiple needles should be matched to provide a uniform circumferential delivery of the ablative fluid from each of the needle tips.

Another feature of the PTAC disclosed in the present application gives the user the ability to lock down the longitudinal motion of the catheter once the distal portion is at the desired site in the renal artery. There are several ways of doing this that can be accomplished using a number of specific features of the PTAC as described herein. These design features include:

1. Tightening the Tuohy-Borst valve at the proximal end of the renal guiding catheter to disallow longitudinal motion of the PTAC.
2. Adding an adhesive pad or Velcro to firmly attach a proximal portion of the PTAC to the skin of the patient or to the proximal end of the guiding catheter.
3. Mechanisms in the proximal section or handle of the PTAC that lock the PTAC longitudinal motion with respect to the guiding catheter. These can include:
   a. A clip that slides coaxially over the outer surface of the PTAC which can be advanced distally until it clips onto the outside of proximal end of the guiding catheter. When clipped onto the guiding catheter, the clip would create a frictional lock with the shaft of the PTAC.
   b. A locking tube that runs distally into the proximal portion of the guiding catheter where the proximal end of the locking tube attaches to the mechanisms in the proximal portion/handle of the PTAC that actuate the guide tubes and/or the injector tubes. Longitudinal or rotational motion of the locking tube will cause the locking tubes distal section to engage the proximal portion of the guiding catheter to prevent longitudinal motion of the PTAC. For example, the tube diameter could get bigger to cause it to have a frictional lock with either the Tuohy-Borst at the proximal end of the guiding catheter or the interior surface of the guiding catheter itself.

Thus a feature of the presently disclosed PTAC is to have a percutaneously delivered catheter with expandable supported needle guiding elements through which injection needles are advanced for injection of an ablative fluid into or beyond the outer layers of the renal artery whose design will reduce or prevent the risk of injury to the intimal and media layers of the renal artery.

Another aspect of the present application is to have a PTAC design with manually expandable guide tubes/needle guiding elements which are advanced outward from the body of the PTAC, the PTAC having support structures that support the guide tubes/needle guiding elements radially against the interior wall of the target vessel.

Another aspect of the present disclosure is to have a PTAC design with manually expandable guide tubes/needle guiding elements which are advanced outwardly from tubular shafts with distal openings in the distal portion of the body of the PTAC, the tubular shafts and openings providing lateral support for the guide tubes/needle guiding elements to ensure they expand uniformly and symmetrically in a circumferential/lateral distribution. For example, if three guide tubes/needle guiding elements are used, the lateral support will help to ensure that a ~120 degree angle is maintained between adjacent guide tubes/needle guiding elements, as the guide tubes/needle guiding elements expand outward.

Another aspect of an embodiment of the PTAC disclosed in the present application is to have an intraluminal centering mechanism (ICM) attached to the guide tubes/needle guiding elements that provides additional radial support or backup to prevent the guide tubes/needle guiding elements from being pushed away from the interior wall of the target vessel as the injector tubes with distal injection needles are advanced through the guide tubes/needle guiding elements into the peri-vascular space.

Another aspect of the PTAC of the present disclosure is to have an intraluminal centering mechanism (ICM) attached to the guide tubes/needle guiding elements that provides additional lateral support to enhance the uniformity of guide tube expansion.

Still another aspect of the PTAC of the present application is to have an intraluminal centering mechanism that reduces the potential trauma to the interior wall of the target vessel from the guide tubes that guide the penetration of the injector needles for tissue ablation.

Still another aspect of the present disclosure is to have a two step injection method for renal denervation where the catheter is filled with normal saline before insertion into the body; then after needle deployment a first injection of ablative fluid (for example ethanol) is done, followed by a second step to flush all the ablative fluid out of the catheter dead space using normal saline or a similar fluid that is non-toxic to the kidneys. The PTAC is then closed and the same two injection steps are used for the other renal artery.

Still another aspect of the present application is to have a one step injection method for renal denervation of each artery, where the catheter is filled with the ablative fluid before insertion into the body; then after needle deployment a single injection of ablative fluid (for example ethanol) is done. The PTAC is then closed and the same single injection step is used for the other renal artery.

Still another aspect of the present disclosure is to have at least three guide tubes/needle guiding elements in the PTAC each having a radiopaque marker. The guide tubes/needle guiding elements being manually expandable outward from within a set of tubular shafts which provide additional support and backup to stabilize each guide tube/needle guiding element against the interior wall of the target vessel. Expansion of the guide tubes/needle guiding elements is accomplished by manipulation of a mechanism in the proximal portion of the PTAC.

Still another aspect of the invention is to have curved expandable injector tubes with injection needles that are able to be coaxially advanced through guide tubes. A distal portion of the injector tubes having a radius of curvature that is similar to that of the guide tubes.

Yet another aspect of an embodiment of the present application is to combine the guide tube and injector tube into an injector tube with thickened proximal portion that acts as the penetration limiter and can be manufactured to set a specific depth of injection.

Yet another aspect of the PTAC of the present disclosure is to use an expandable balloon to provide radial expansion and support for the guide tubes/needle guiding elements and/or injector tubes with distal injection needles.

Yet another aspect of the PTAC of the present application is to have the flow resistance of each of the multiplicity of needles be approximately the same.

Yet another aspect of the PTAC of the present disclosure is to include one or more of the following radiopaque markers to assist in positioning, opening, closing and using the PTAC. These include the following:

A radiopaque ring marking the distal end of the sheath;
Radiopaque markers at, or very close to the ends of the guide tubes using either metal bands or plastic with a radiopaque filler such as barium or tungsten;
Radiopaque markers on the distal portion of the injection needles;
Radiopaque wires inside the lumen of the injector tubes and/or injection needles;
The distal fixed guide wire of the PTAC being radiopaque (e.g., using platinum wire);
Radiopaque markers on the intraluminal centering mechanism (ICM).

Throughout this specification the terms injector tube with distal injection needle is used to specify a tube with a sharpened distal end that penetrates into tissue and is used to inject a fluid into that tissue. Such a structure could also be called a hypodermic needle, an injection needle or simply a needle. In addition, the terms element and structure may be used interchangeably within the scope of this application. The term Luer fitting may be used throughout this application to mean a tapered Luer fitting without a screw cap or a Luer Lock fitting that has a screw cap.

The present disclosure, in some aspects, provides a catheter for fluid delivery through at least two injection needles into tissue outside of the interior wall of a target vessel of a human body. In some embodiments, the catheter is provided having a central axis extending in a longitudinal direction and a fluid injection lumen. The catheter can include at least two guide tubes configured to advance distally and expand outwardly toward the interior wall of the target vessel. The catheter can include a mechanical support structure having a deflection surface. The deflection surface deflects the at least two guide tubes toward the interior wall of the target vessel. The catheter can include at least two injector tubes having distal injection needles. Each distal injection needle can have an injection lumen in fluid communication with the fluid injection lumen of the catheter body. The at least two injector tubes are configured to advance distally and expand outwardly, guided by the at least two guide tubes to penetrate the interior wall of the target vessel. The distal injection needles can have an opening for fluid delivery.

The present disclosure, in some aspects, provides a catheter for fluid delivery through at least two injection needles into tissue outside of the interior wall of a target vessel of a human body. In some embodiment, the catheter is provided having a central axis extending in a longitudinal direction and also comprising a fluid injection lumen. The catheter can include a sheath having a distal closed position and a proximal open position. The catheter can include at least two self-expanding guide tubes adapted to expand outwardly toward the interior wall of the target vessel when the sheath is moved from its distal closed position to its proximal open position. The catheter can have a handle located near the proximal end of the catheter. The handle can be configured to move the sheath in the longitudinal direction with respect to the self-expanding guide tubes. The catheter can include at least two injector tubes with distal injection needles each having an injection lumen in fluid communication with the fluid injection lumen of the catheter body. The at least two injector tubes with distal injection needles are configured to be advanced outwardly, guided by the at least two guide tubes to penetrate the interior wall of the target vessel. The at least two injection needles can have a distal opening for fluid delivery into the tissue outside of the interior wall of the target vessel. The catheter can include a mechanical support structure. The mechanical support structure can provide support for the at least two self-expanding guide tubes in a direction selected from the group consisting of a) radial, in which the mechanical support structure supports each guide tube in a radial direction, and b) lateral, in which the mechanical support structure supports each guide tube in a lateral direction. The distal end of the injection needles can be withdrawn into the at least two self-expanding guide tubes and the at least two self-expanding guide tubes can be withdrawn into the catheter body in the distal closed position. The distal closed position can prevent needlestick injuries form the sharpened distal end of the injection needles.

The present disclosure, in some aspects, provides a catheter for fluid delivery through at least three injection needles into tissue outside of the interior wall of a target vessel of a human body. In some embodiments, the catheter is provided having a catheter body having a central axis extending in a longitudinal direction and a fluid injection lumen. The catheter can include at least three guide tubes adapted to advance distally and expand outwardly toward the interior wall of the target vessel. The catheter can include a handle located near a proximal end of the catheter. The handle can include a plurality of fittings. The catheter can include a fluid injection port located near a proximal end of the catheter. The fluid injection port can have a non-standard connector that is different from any other fitting on the handle of the catheter and configured to reduce the chance of accidentally injecting the ablative fluid into any other fitting. The injection port can be in fluid communication with the fluid injection lumen of the catheter. The catheter can include at least three injector tubes each comprising distal injection needles. Each of the at least three injector tubes can include an injection lumen in fluid communication with the fluid injection lumen of the catheter body. The at least three injector tubes are configured to be advanced outwardly, guided by the at least three guide tubes to penetrate the interior wall of the target vessel. The injection needles can have a distal opening for fluid delivery into the tissue outside of the interior wall of the target vessel.

The present disclosure, in some aspects, provides a catheter for fluid delivery through at least two injection needles into tissue outside of the interior wall of a target vessel of a human body. The catheter provided can include a catheter body comprising a central axis extending in a longitudinal direction and also having a fluid injection lumen. The catheter can include at least two guide tubes configured to advance distally and expand outwardly toward the interior wall of the target vessel. The catheter can include a mechanical support structure configured to support each expanded needle guiding element in a direction selected from the group consisting of a) radial, in which the mechanical support structure supports each needle guiding element in a radial direction, and b) lateral, in which the mechanical support structure supports each needle guiding element in a lateral direction. The catheter can include at least two injector tubes with distal injection needles. Each of at least two injector tubes can have an injection lumen in fluid communication with the fluid injection lumen of the catheter body. The at least two injector tubes with distal injection needles are configured to be advanced outwardly, guided by the at least two guide tubes to penetrate the interior wall of the target vessel. The injection needles can have a distal opening for fluid delivery into the tissue outside of the interior wall of the target vessel. The catheter can be sized and configured to obscure less than about 50%, 40%, 30%, or less of the cross sectional area of the lumen of the target vessel when the catheter is in a configuration penetrating the interior wall of the target vessel, for example, when the target vessel has a cross sectional area of between about 30 mm$^2$ and about 300 mm$^2$, between about 30 mm$^2$ and about 150 mm$^2$, between about 50 mm$^2$ and about 120 mm$^2$, or about 30 mm$^2$, about 50 mm$^2$, about 80 mm$^2$, about 120 mm$^2$, about 150 mm$^2$, about 200 mm$^2$, about 250 mm$^2$, or about 300 mm$^2$. As such the catheter of the present disclosure is improved over the Chan catheter for applications where obstructed blood flow is contraindicated including use in renal denervation where it is disadvantageous to cut off or reduce blood flow to a kidney. This includes renal denervation in dialysis patients, patients with only one functioning kidney and patients with already reduced blood flow to a kidney e.g. from renal artery stenoses.

The present disclosure, in some aspects, provides a method for fluid delivery to an interior wall of a target vessel. The method can include the step of providing a catheter body. The method can include the step of providing a mechanical support structure configured to support at least two guide tubes in a direction selected from the group consisting of a) radial, in which the mechanical support structure supports each guide tube in a radial direction, and b) lateral, in which the mechanical support structure supports each guide tube in a lateral direction. The method can include the step of advancing distally and expanding outwardly at least two guide tubes toward the interior wall of the target vessel. The method can include the step of deflecting the distally moving guide tubes outward toward the interior wall of the target vessel. The method can include the step of advancing distally and expanding outwardly at least two injector tubes with distal injection needles. The method can include the step of delivering fluid to the interior wall of the target vessel via the injection needles, wherein while delivering fluid the catheter body obstructs less than about 50%, 40%, 30%, or less of the cross sectional area of the lumen of the target vessel. The method can include the step of supporting each guide tube radially, by the mechanical support structure. The method can include the step of supporting each guide tube laterally, by the mechanical support structure. The method can include the step of penetrating the interior wall of the target vessel with the distal injection needles. The method can include the step of delivering fluid through the distal opening of the injection needles. The method can include the step of centering the catheter by touching the at least two guide tubes to the interior wall of the target vessel. The method can include the step of simultaneously advancing outward the at least two guide tubes. The method can include the step of simultaneously advancing outward the at least two injector tubes. The method can include the step of penetrating the tissue outside of the interior wall of the target vessel to an equal depth.

In some embodiments, the catheter can include a mechanical support structure having a deflection surface. The deflection surface deflects the guide tubes outward toward the interior wall of the target vessel. In some embodiments, the mechanical support structure is a central buttress support located internal to a distal portion of the catheter body. The central buttress support is adapted to support the two guide tubes. In some embodiments, the catheter can has a lateral support structure adapted to support the guide tubes as they expand outward. The lateral support structure can be, for example, a) a tubular shaft located near the distal portion of the catheter body, the tubular shaft having an opening through which at least one of the two guide tubes is advanced, b) an intraluminal centering mechanism attached to the two guide tubes, or c) a central buttress that also provides the radial support for the two guide tubes. In some embodiments, two or more of a) a tubular shaft located near the distal portion of the catheter body, the tubular shaft having an opening through which at least one of the two guide tubes is advanced, b) an intraluminal centering mechanism attached to the two guide tubes, or c) a central buttress that also provides the radial support for the two guide tubes may be combined.

In some embodiments, the catheter includes at least two tubular shafts located within a distal portion of the catheter body. Each of the tubular shafts can have a distal opening through which one of the at least two guide tubes is advanced. The catheter can have a closed position, wherein the distal ends of the distal injection needles are withdrawn into the at least two guide tubes and the at least two guide tubes are withdrawn into the at least two tubular shafts, wherein the closed position is configured to prevent needle-stick injuries from the distal injection needles. In some embodiments, the mechanical support structure is coupled to a longitudinally movable mechanism. In some embodiments, the catheter can include a fully closed position, the fully closed position having the distal end of the injection needles being withdrawn into the guide tubes and the guide tubes withdrawn into the tubular shafts, the fully closed position preventing needlestick injuries from the sharpened distal end of the injection needles. The longitudinally movable mechanism can be an obturator.

In some embodiments, the catheter includes three needle guide tubes, three injection needles, and three injector tubes, wherein the distal end of each injector tube coupled to one of the injection needles. The catheter can have at least three guide tubes and three injector tubes with distal injection needles with each injection needle having a sharpened distal end. In some embodiments, the mechanical support structure can include an obturator movable in the longitudinal direction. In some embodiments, the mechanical support structure can include an intraluminal centering mechanism.

In some embodiments, two guide tubes have a curved distal portion with a first radius of curvature and the at least two injector tubes with distal injection needles have a curved distal portion with a second radius of curvature, wherein the first radius of curvature and second radius of curvature being preset to within about 40 percent, 35 percent, 30 percent, 25 percent, 20 percent, 15 percent, 10 percent, or less of each other. In some embodiments, the catheter includes a fixed distal guidewire. In some embodiments, the total internal volume or dead space from a proximal part to a distal end of an infusion flow path of the catheter is less than about 0.5 ml, 0.4 ml, 0.3 ml, or less. In some embodiments, the catheter includes a radiopaque marker attached to or within a portion of one or more of the structures selected from the group consisting of: a) the injection needle, b) the guide tubes, c) the catheter body, and d) the mechanical support structure. The radiopaque markers can be operably connected to a portion of one or more of the structures selected from the group of: a) the injector tubes with distal injection needles, b) the guide tubes, the mechanical support structure and c) the catheter body.

In some embodiments, the catheter includes a single injection port located near a proximal end of the catheter. The single fluid injection port can be in fluid communication with the fluid injection lumen of the catheter body. In some embodiments, the catheter includes an injection port located near a proximal end of the catheter. The fluid injection port can have a non-standard connector that is a different from any other fitting on the handle of the catheter. In some embodiments, a custom syringe having a distal end configured to mate with the non-standard connector is provided. In some embodiments, the catheter can have a control mechanism adapted to control the movement and outward expansion of the two guide tubes. In some embodiments, the catheter can have an injection needle control mechanism configured to control the movement and outward expansion of the injection needles. The guide tubes are cannulas that may also be called needle support elements and as such are typically tubular elements through which the sharpened injection needles are advanced toward the inside wall of the target vessel.

These and other features and advantages of this invention will become obvious to a person of ordinary skill in this art upon reading of the detailed description of this invention including the associated drawings and the claims.

BRIEF DESCRIPTION OF THE DRAWINGS

FIG. 5 is an enlargement of region S5 of the PTAC of FIG. 3.

FIG. 6 is a transverse cross-section at section 6-6 of the PTAC longitudinal cross-section enlargement shown in FIG. 5.

FIG. 7 is a transverse cross-section at section 7-7 of the PTAC longitudinal cross-section enlargement shown in FIG. 5.

FIG. 21A is a schematic view of an alternative embodiment of the PTAC which uses the proximal portion of the obturator as the support structure for the guide tubes and shows the configuration of the PTAC after the guide tubes are advanced but before the needles are advanced.

FIG. 21B is a schematic view of an alternative embodiment of the PTAC in which the proximal portion of the obturator provides additional support for the guide tubes.

DETAILED DESCRIPTION

Figure 1:
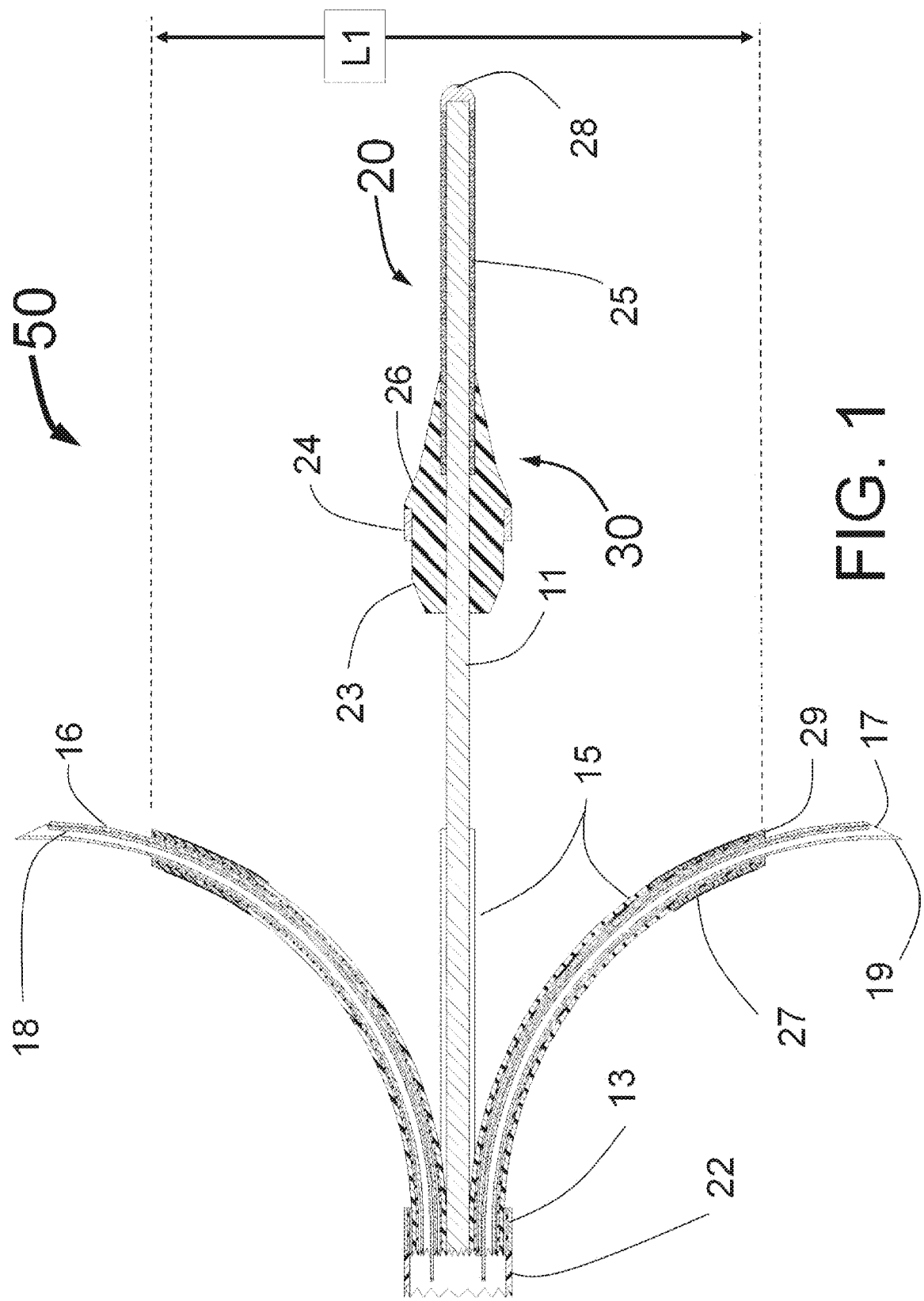
FIG. 1 is a longitudinal cross-section of a distal portion of an Intraluminal Nerve Ablation System (INAS) having a fixed guide wire at its distal end.

FIG. 1 is a longitudinal cross-section of the expanded distal portion of the invention by Fischell as described in U.S. patent application Ser. No. 13/643,070 filed on Oct. 23, 2012. This Intra-vascular Nerve Ablation System (INAS) 50 has a fixed guide wire 20 with tip 28 at its distal end. FIG. 1 shows the INAS 10 in its fully open position with the self-expanding guide tubes 15 with coaxial injector tubes 16 with sharpened distal injection needles 19 and needle distal opening 17 which is the injection egress deployed outward beyond the distal end 29 of the guide tubes 15. It should be understood that this embodiment of the INAS 50 has four injector tubes 16 protruding through four guide tubes 15. The guide tubes 15 are the needle guiding elements that help support the thin and flexible injector tubes 16 with distal injection needles 19 as they are advanced into the wall of a target vessel.

In this configuration, the sheath 22 has been pulled back to allow the guide tubes 15 with radiopaque marker bands 27 to expand outwardly. If the elements 15 and 16 are not fabricated from a radiopaque metal, it is envisioned that the distal portion of the injector tube(s) 16 and guide tube(s) 15 would be marked with a radiopaque material such as gold or tantalum, or a piece of radiopaque material may be used to form or be located within the injector tubes 16 or the sharpened needles 19 to provide better visualization of the deployment of the INAS 50 using standard fluoroscopy. FIG. 1 shows a radiopaque wire 18 placed within the injector tube 16 to allow fluoroscopy to be used by the operator to clearly identify the position of the injector tubes 16 with distal injection needles 19. It is particularly important, in some cases, for the operator to know the location of the injection needles 19 after they have been advanced through the wall of the vessel. The material for the radiopaque wire 18 can be selected from well-known radiopaque metals such as platinum, tantalum or gold or an alloy of that type of metal.

The diameter L1 denotes the memory configuration for the fully opened guide tubes 15. For use in the renal arteries, L1 would typically be between 3 and 10 mm with 8 mm being a best configuration if only one size is made as very few renal arteries have a diameter that is larger than 7 mm. Also shown in FIG. 1 are the distal ends 29 of the guide tubes 15 that in the fully open configuration have their planes situated parallel to the longitudinal axis of the INAS 50. The distal portion of the INAS 50 has the tapered section 26, radiopaque marker band 24 and proximal portion 23. This tapered unit including elements 23, 24 and 26 is called an obturator 30. The obturator 30 is fixedly attached to the core wire 11 and the outer layer 25 of the guide wire 20. Other important features of some embodiments of this design are the radiopaque marker 13 located at the distal end of the sheath 22 that in combination with the radiopaque marker band 24 on the obturator 30, provide indication of the relative position of the distal end of the sheath 22 and the obturator 30. When the radiopaque marker 13 located at the distal end of the sheath 22 is in close proximity to the radiopaque marker band 24 of the obturator 30, the operator knows that the guide tubes 15 containing the injector tubes 16 are fully enclosed. When the radiopaque marker 13 of the sheath 22 are fully separated, the operator knows that at least the guide tubes 15 are each deployed outward to have their distal ends 29 placed in contact the interior surface of the vessel. Also disclosed in the Fischell design is that the natural preformed radius of curvature of the injector tubes 16 should correspond to that of the guide tubes 15 so that the guide tubes 15 will maintain their position against the interior wall of the target vessel as the injector tubes 16 with distal injection needles 19 are advanced coaxially there through to penetrate the wall of the target vessel. As previously discussed, the limitation of this design is that the reliability and stability of unsupported self-expanding needle guiding element structures such as the guide tubes 15 that might not automatically be centered in the target vessel. In addition the guide tubes 15 without any additional radial support can back away from the interior wall of the target vessel during advancement of injector tubes 16.

Figure 2:
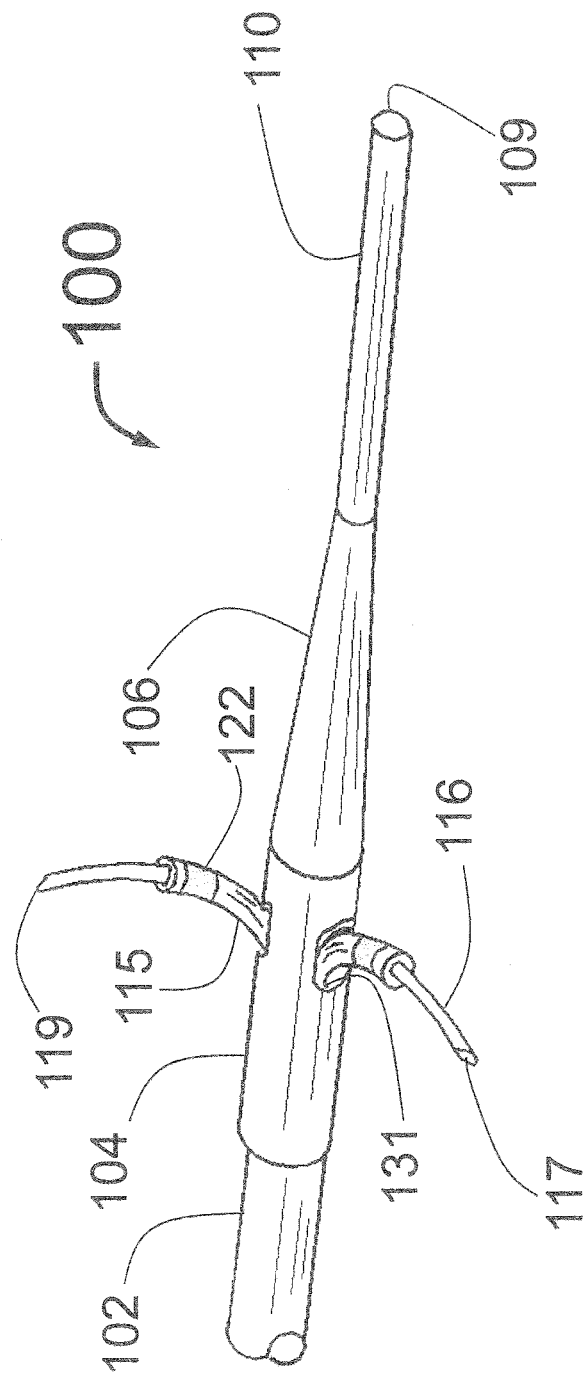
FIG. 2 is a schematic view of the distal portion of the PTAC in its open position as it would be manually expanded for delivery of an ablative agent into the peri-vascular space.

FIG. 2 is a schematic view of the distal portion of a PTAC 100 in its open position, showing an outer tube 102, outer tube extension 104 having distal openings 131 through which the guide tubes 115 with radiopaque markers 122 are advanced outward from the body of the PTAC 100. Also shown is the tapered section 106 and fixed guide wire 110 with distal tip 109. The injector tubes 116 with distal injection needles 119 and needle distal openings 117 are shown in their fully deployed positions. The openings 131 support the sides of the guide tubes 115 as the guide tubes 115 are advanced outward before the advancement of the injector tubes 16 with distal injector needles 119. The PTAC 100 of FIG. 2 has three guide tubes with the third tube hidden behind the catheter and not visible in this schematic view. Although the PTAC 100 of FIG. 2 has three guide tubes 115, it is envisioned that other embodiments could have as few as one or as many as eight guide tubes with an optimum number being three or four. A larger diameter target vessel might suggest the use of as many as 4 to 8 guide tubes 115 and injector tubes 116.

Different shapes are envisioned for the distal openings (or windows) 131 in the outer tube extension 104 where the guide tubes 115 exit. These possible shapes include a racetrack design with curved (e.g., round) proximal and distal ends and straight sides in the axial direction, and oval or round shapes. It is also envisioned that there could be a movable flap covering the opening 131 or a slit that could be opened to make the outer surface of the PTAC smooth for better delivery into the renal artery.

It is an important feature, in some embodiments of this invention that the guide tubes 115 are needle guiding elements for the ultra-thin injection needles 119. Specifically, prior art such as Jacobson that describe curved needles that are advanced outward from a central catheter to penetrate the wall of a target vessel, have needles that are advanced (naked) on their own from the distal end or side of a catheter. Without additional guiding and backup support during advancement, needles that are thin enough to essentially eliminate the risk of bleeding following penetration and withdrawal from the wall of the artery are generally too flimsy to reliably penetrate as desired into the vessel wall. Thus it is envisioned that a key aspect of the PTAC 100 of the present application is the inclusion of needle guiding elements such as the guide tubes 115 that allow the ultra-thin injection needles 119 to be reliably advanced into the wall of a target vessel to the desired depth.

Figure 3:
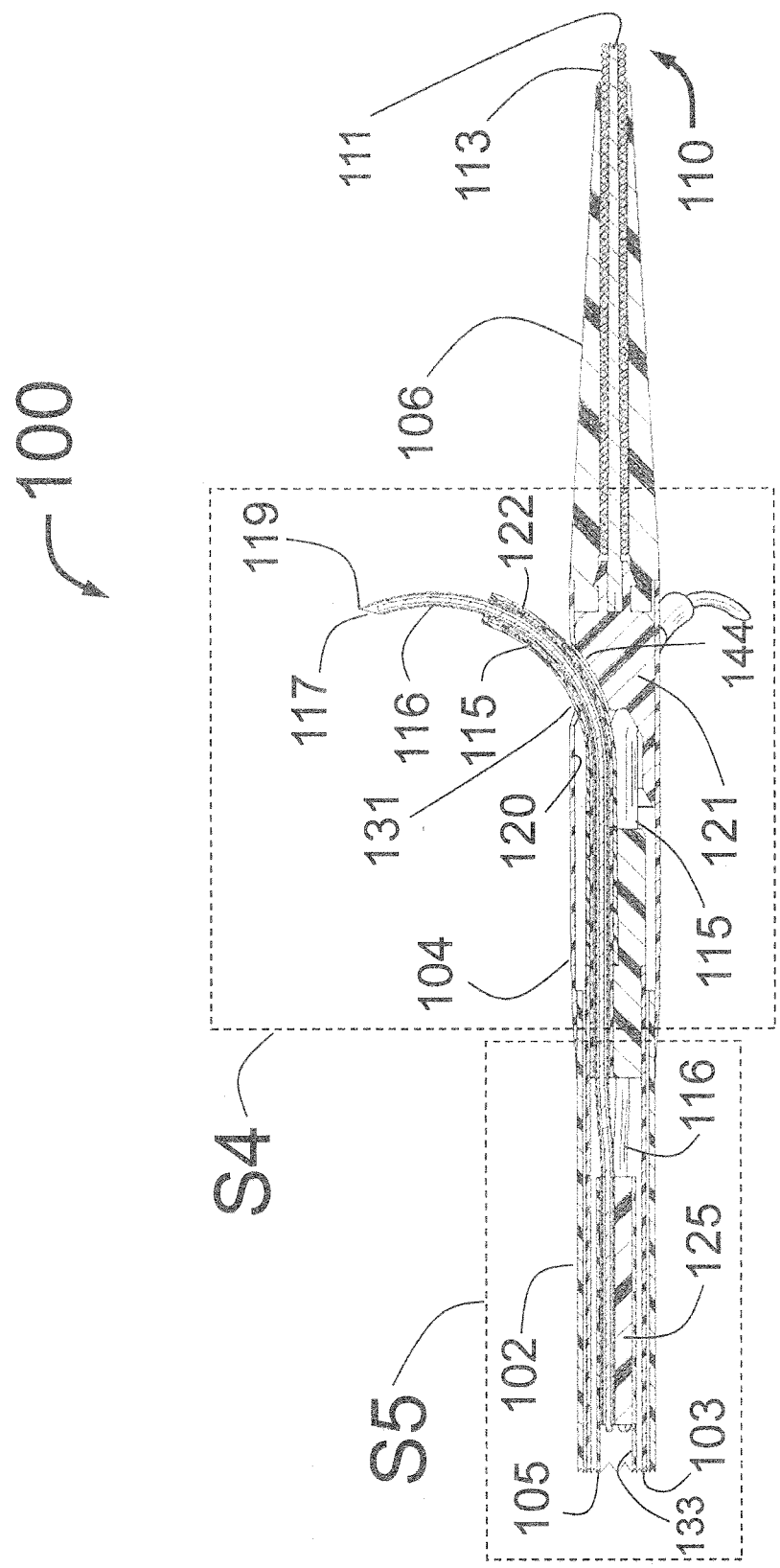
FIG. 3 is a longitudinal cross-section of a distal portion of the PTAC of FIG. 2 in its open position as it would be configured for delivery of an ablative solution into the target vessel wall.
Figure 4:
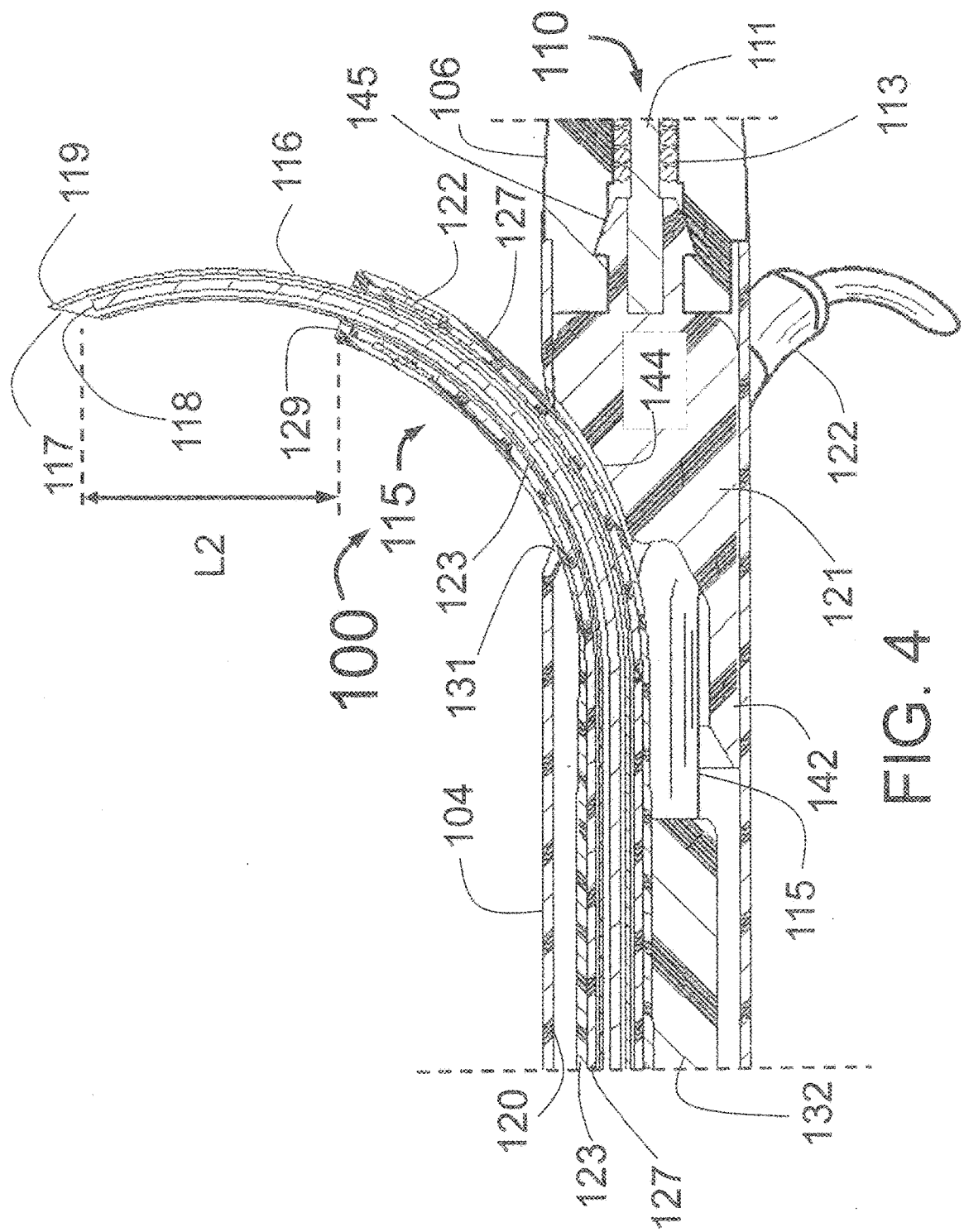
FIG. 4 is an enlargement of region S4 of the PTAC of FIG. 3.

FIG. 3 is a longitudinal cross-section of a distal portion of the PTAC 100 as shown in FIG. 2. The proximal end of FIG. 3 shows the three concentric tubes, the outer tube 102, middle tube 103 and inner tube 105 which form the central portion and most of the length of the PTAC 100. The outer tube 102 is attached to the outer tube extension 104 which is in turn attached to the tapered section 106. The fixed guide wire 110 with core wire 111 and outer layer 113 extends distally from the distal end of the tapered section 106. It should be noted that only part of the length of the guide wire 110 is shown in FIG. 3, its full length is shown in FIG. 2. Enlargements of the sections S4 and S5 of FIG. 3 are shown in FIGS. 4 and 5 respectively.

FIG. 3 shows the guide tube 115 with radiopaque marker 122 in its fully advanced position placed through the opening 131 in the outer tube extension 104. The interior surface of the outer tube extension 104 forms part of the tubular shaft 120 should be made from a stiff material such as a metal or high durometer plastic so that it will be relative rigid as the guide tubes 115 are advanced and retracted.

A preferred embodiment of the PTAC 100 of the present application uses four different tubular structures instead of just an outer tube 102 and outer tube extension 104. Specifically, the proximal section would be a metal hypotube 82 shown in FIG. 11. The metal hypotube 82 would connect at its distal end to a relatively stiff plastic tube 92 (see FIG. 18) about 20 cm long that would in turn connect to a softer more flexible plastic tube about 10 cm long which would be the tube 102 shown in FIGS. 2-7. The plastic tubes 92 and 102 would typically have the same interior and outside diameters. The outer tube extension 104 which is the distal end section of the catheter body typically has a slightly larger inside diameter than the soft outer tube 102. The manifold 125 that connects the inner tube 105 to the injector tubes 116 is coaxially within the plastic tubes 92 and 102 and at least several centimeters proximal to the outer tube extension 104 which is the distal end section of the catheter body of the PTAC 100.

Figure 18:
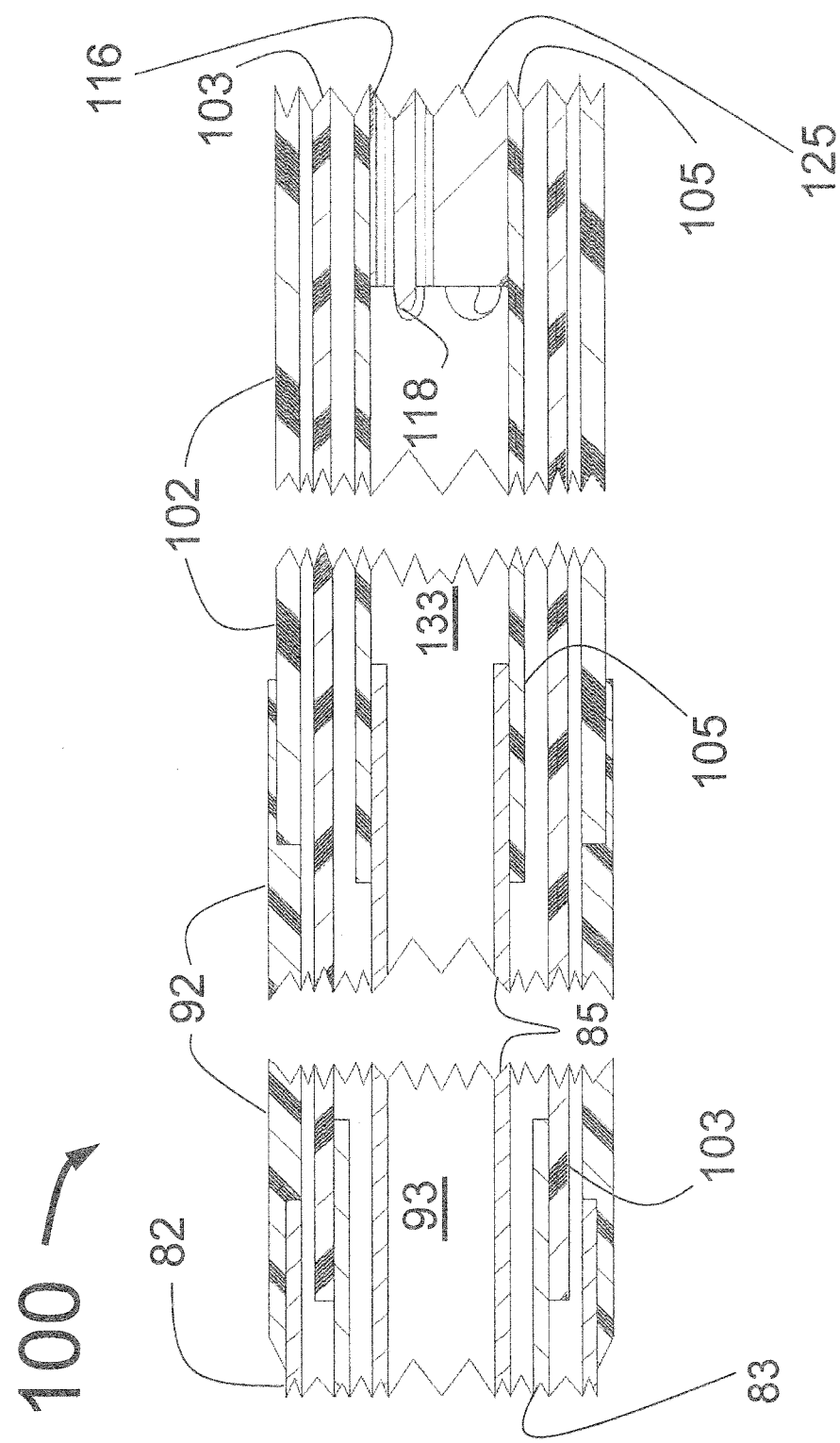
FIG. 18 is a longitudinal cross-section of the central portion of the PTAC showing the multiple sections of the inner, middle and outer tubes.

In a preferred embodiment, the middle tube 103 attaches to, a proximal metal hypotube and the inner tube 105 would also attach to proximal portion formed from a metal hypotube. The structure of these tubes is shown in FIG. 18.

An important aspect, in some embodiments of the presently disclosed PTAC 100 is to minimize the internal volume or "dead space" for the injection path. This reduces the needed amount of fluid that would be injected into the peri-vascular space before the ablative fluid is injected. In one version of the directions for use, the internal volume would first be flushed and filled with normal saline outside of the body before the PTAC 100 is inserted into the body. Ideally the dead space should be less than 0.3 ml and if possible, close to 0.1 ml. Any volume less than 0.5 ml would be helpful to minimize the amount of flushing fluid injected into the peri-vascular space prior to the injection of the ablative fluid.

The central buttress 121 shown in FIG. 3, supports the guide tube 115 both as it is pushed distally and after it is fully deployed. The guide tubes 115 can slide along a deflection surface such as the curved ramp 144 of the central buttress 121 (shown in the FIG. 4) as they are pushed by the guide tube control mechanism 330. The guide tube control mechanism 330 can advance a plurality of guide tubes 115 simultaneously. The guide tubes 115 advance toward the distal end of the PTAC 100 toward the openings 131. The guide tubes 115 can interact with a deflection surface such as the curved ramp 144 of the central buttress 121 as they are guided toward the openings 131. The deflection surface 144 guides the distally moving guide tubes 115 outward toward the interior wall of the target vessel.

This central buttress 121 is a mechanical support structure that provides radial support for the advanced guide tubes 115 that prevents the guide tubes 115 from backing away from the interior wall of the target vessel as the injector tubes 116 are advanced through the guide tubes 115 forward to their desired position 2-4 mm beyond the interior wall of the target vessel. In exceptional cases, the injection needles 119 at the distal ends of the injector tubes 116 might be advanced as deep as 8 mm beyond the interior wall of the target vessel. Lateral support for the guide tubes 115 is provided by the sides of the openings 131 that in combination with the central buttress 121 are key to the radial and circumferential/lateral support both during guide tube 115 advancement and outward expansions, and as backup during delivery of the injection needles 119 through the interior wall of the target vessel.

The central buttress 121 is disposed within the PTAC 100, and in some embodiments, within the outer tube extension 104. The central buttress 121 has a smaller diameter than the PTAC 100 and the outer tube extension 104. The central buttress 121 may be fixed, immobile, and/or non-expandable relative to the PTAC 100. The distal tip 145 of the central buttress 121 can be coupled (e.g., snap fit) with the tapered section 106. The central buttress 121 may be integrally formed within the PTAC 100 (e.g., the central buttress 121, the distal openings 131, and/or the tapered section 106 could be a single component molded or machined).

The buttress 121 may comprise a deflection surface, such as a curved or linear ramp. In some embodiments, the deflection surface is substantially parallel, parallel, substantially coaxial or coaxial to the longitudinal axis of the PTAC 100. In other embodiments, the deflection surface can be substantially perpendicular, perpendicular, substantially offset, offset, substantially angled, or angled to the longitudinal axis of the PTAC 100. The deflection surface and the longitudinal axis of the PTAC 100 may form an angle of, for example, approximately 20 degrees, 25 degrees, 30 degrees, 35 degrees, 40 degrees, 45 degrees, 50 degrees, 55 degrees, 60 degrees, 65 degrees, 70 degrees, between 30-50 degrees, and in some embodiments 45 degrees. The deflection surface can be substantially curved. In some embodiments, the deflection surface includes a concave surface. The deflection surface may include a convex surface near the proximal end of the PTAC 100 and a complementary concave surface near the distal end of the PTAC 100. The curved or concave surface may correspond to the radius of curvature of the unconstrained distal surface of the guide tube 115. The deflection surface may form a lumen. The lumen may be curved, bowed, linear, or non-linear. The lumen may correspond to the radius of curvature of the distal surface of the guide tube 115.

The deflection surface may be configured to direct the guide tubes 115 toward the distal openings 131. The distal openings 131 are located on tubular shaft 120. The number of distal openings 131 may correspond to the number of guide tubes 115 (e.g., 1:1 ratio), or the number of distal openings 131 may be more or less than the number of guide tubes 115. The distal openings 131 may abut the deflection surface. In some embodiments, the distal openings 131 are the same size and/or shape as the lumen, and in other embodiments, the distal opening is larger or smaller than the lumen. The distal portion of the central buttress 121 is shown in greater detail in FIG. 17.

The deflection surface such as curved ramp 144 of the central buttress 121 and the distal openings 131 the tubular shaft 120 also provide lateral support that facilitates outward expansion purely in the radial direction for the guide tubes. Although the buttress 121 provides both radial and lateral support for the guide tubes 115, other embodiments as described herein may provide only radial support or only lateral support. Radial support for the guide tubes 115 is defined herein as being support for the guide tubes 115 in a direction that is perpendicular to the longitudinal axis of the PTAC 100. Lateral support for the guide tubes 115 is defined herein as being support for the guide tubes 115 in a circumferential direction that is perpendicular to the radial direction.

It is also an important feature, in some cases, that the radius of curvature of the distal portion of the injector tubes 116 have a central axis with the same, or nearly the same, radius of curvature as the central axis of the guide tubes 115 and of the central axis of the distal portion of the tubular shaft 120 that is formed within the central buttress 121 when measured in an unconstrained state. In addition, the length of the guide tubes 115 should be at least as long as the distal curved portion of the injector tubes 116 with distal needles 119. This design constrains the curved portion of each injector tube 116 within the lumen of the guide tube 115 so that the injector tube 116 cannot twist or change position.

Figure 13:
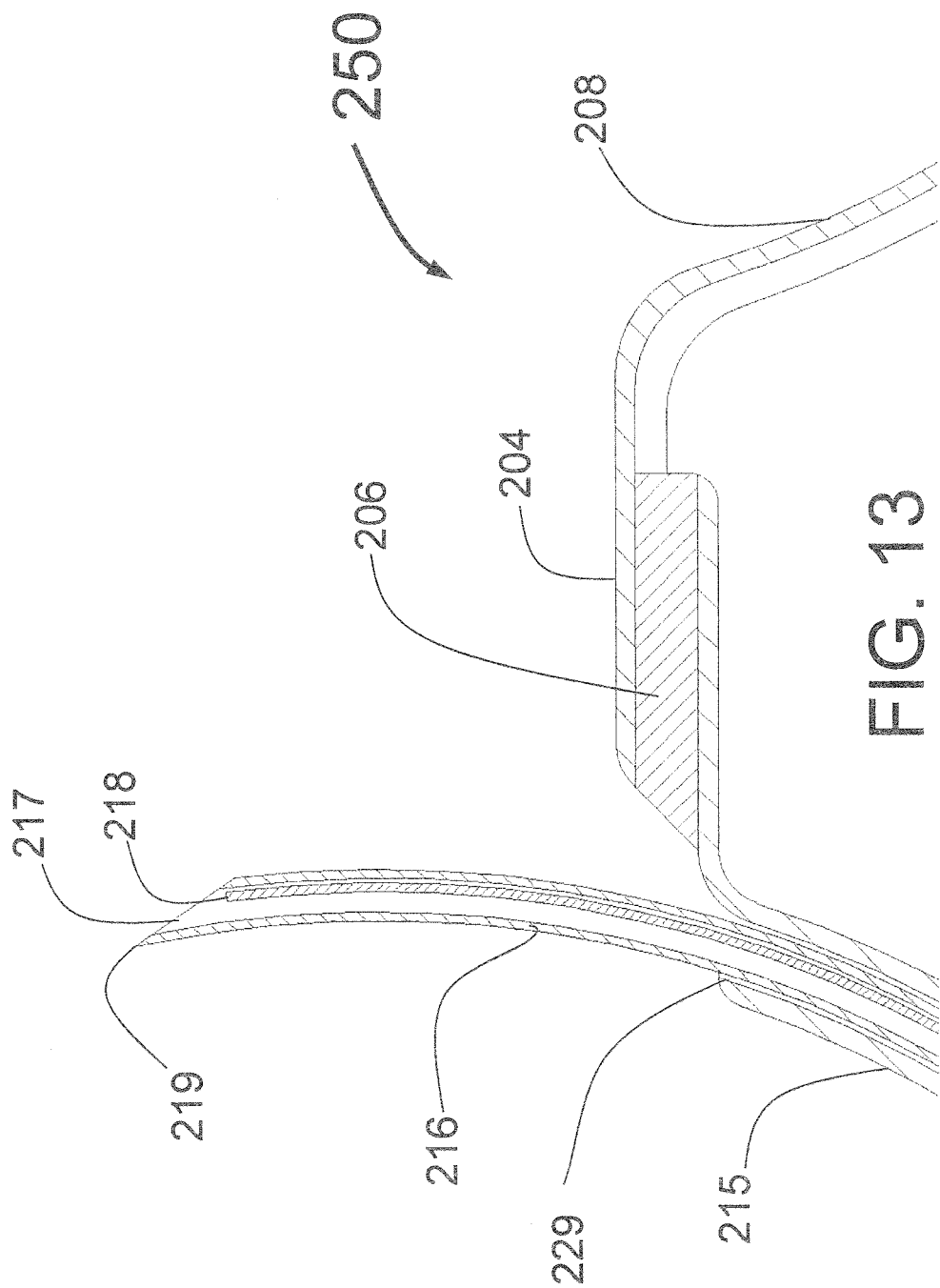
FIG. 13 is an enlargement of the region S13 of the intraluminal centering mechanism (ICM) of FIG. 12.

The preformed radius of curvature of the injector tubes 116 can be similar to that of the guide tubes 115 so that the guide tubes 115 will maintain their position against the interior wall of the target vessel as the injector tubes 116 with distal injection needles 119 are advanced to penetrate the interior wall of the target vessel. Specifically, the radius of curvature of the central axis of the distal portion of the injector tube 116 can be approximately the same as the radius of curvature of the central axis of the guide tube 115. The radii of curvature of the central axes of the guide tubes 115 and the injector tubes 116 can be within 1 mm of each other, or within 0.2 mm of each other in some cases. Although a curved shape with a single radius of curvature is shown in FIG. 13, curved shapes of the guide tubes 115 and injector tubes 116 could have two or more portions each with a different radius of curvature. Even if two or more different radii of curvature are used for these components, it can be advantageous that when fully deployed, the curved shape of the injector tube 116 is such that its longitudinal axis is coaxial to the longitudinal axis of the lumen of the curved portion or portions of the guide tube 115. In other words, the advanced injector tube 116 can in some embodiments fit perfectly within the advanced guide tube 115. It is also envisioned that if the radii of curvature are significantly different then the radius of curvature of the injector tube 116 can be less than the radius of curvature of the guide tube 115 so that when the injector tube 116 is advanced it will not push the guide tubes 115 away from the interior wall of the vessel. Another way to characterize the two radii of curvature is that they can be, in some cases, within about 20% of each other and ideally, in some embodiments within about 5%.

As seen in FIG. 3 the inner tube 105 with fluid injection lumen 133 connects through the manifold 125 to the three injector tubes 116, thus the lumens of the injector tubes 116 are in fluid communication with the lumen 133. The inner tube 105 and manifold 125 can slide along the longitudinal axis of the PTAC 100 inside of the middle tube 103 which is shown with uniform diameter over its length including the portion coaxially outside of the manifold 125.

It is clear from the drawing of FIG. 3 that the manifold 125 is located within the lumen of the inner tube 105 in a portion of the tube 105 that is proximal to the distal end of the tube 105. The inner tube 105 and manifold 125 are both located coaxially within the outer tube 102 of the PTAC 100 at a position proximal to the outer tube extension 104 which is the distal end section of the outer body of the PTAC 100. This differs significantly from the embodiment shown in FIG. 3 of the Jacobson U.S. Pat. No. 6,302,870 where the manifold that connects the tube to the needles is attached to the distal end of the tube (instead of being inside it and proximal to the distal end). In addition the Jacobson manifold lies coaxially within the distal end section of the outer body of the catheter (instead of being in the tube that is proximal to the distal end section of the catheter). The distal end section being defined as that distal portion of the catheter from which the needles emerge to curve outward into the wall of a vessel.

An important feature, in some embodiments of the PTAC 100 can be that the flow rate through the needle distal opening 117 for each needle 119 of the PTAC 100 of FIGS. 2 through 4 is approximately the same. This can most easily be accomplished by pre-testing each injector tube 116 with injection needle 119 and measuring the flow rate, and thus the flow resistance under a given pressure. Injector tubes 116 would be sorted according to results of the testing and the injector tubes selected for each PTAC 100 would be so matched in order to have approximately the same flow resistance.

FIG. 4 is the enlargement of section S4 of the longitudinal cross-section of the PTAC 100 as shown in FIG. 3. FIG. 4 shows the details of the guide tubes 115 with interior layer 123, outer layer 127, distal end 129 and radiopaque marker 122. Coaxially within the lumen of the guide tube 115 is the injector tube 116 with distal injection needle 119, distal opening 117 and radiopaque marker wire 118. The radiopaque marker wire 118 serves two purposes, first it provides fluoroscopic visibility of the injector tubes as they are advanced to their position for delivery of the ablative fluid into the peri-vascular space into and deep to the adventitia of the target vessel. Second—the marker wire 118 reduces the internal volume of the injector tube 116, and thus reduces the amount of saline required to flush all of the ablative fluid out of the PTAC 100 into the peri-vascular space leaving only harmless saline in the PTAC 100 as it is retracted back into the renal artery. Radiopacity of the injector tubes 116 with distal needles 119 is important, in some embodiments, so that the operator can confirm under fluoroscopy that the needles 119 have properly deployed into the wall of the target vessel. Other embodiments of the present disclosure may use coatings, plating or markers on the outside and/or inside of the injector tube 116 and needle 119 or the injector tube 116 with distal needle 119 could be made from a two layer clad material. For example, nitinol tubing clad over a platinum inner tube and then shape set would be ideal as it would be quite visible and eliminate the need for the added marker wire 118 shown in FIGS. 3 and 4.

The guide tubes 115 are advanced and retracted through the tubular shaft 120 with distal opening 131. The three guide tubes 115 are attached to each other near their proximal ends by the guide tube connector 132. FIG. 4 also clearly shows how the guide tube 115, when advanced against the central buttress 121 is forced outward and is supported by the curved ramp 144 of the central buttress 121 as well as the sides of the opening 131 of the tubular shaft 120. The central buttress 121 also has proximal fingers 142 that provide additional lateral support for the guide tubes 115. The curved ramp 144 acts as a deflection surface to deflect the guide tubes 115 outwardly as they are advanced.

The outer tube extension 104 connects at its distal end to the tapered section 106 which in turn lies coaxially around the guide wire 110 with core wire 111 and outer layer 113.

Figure 11:
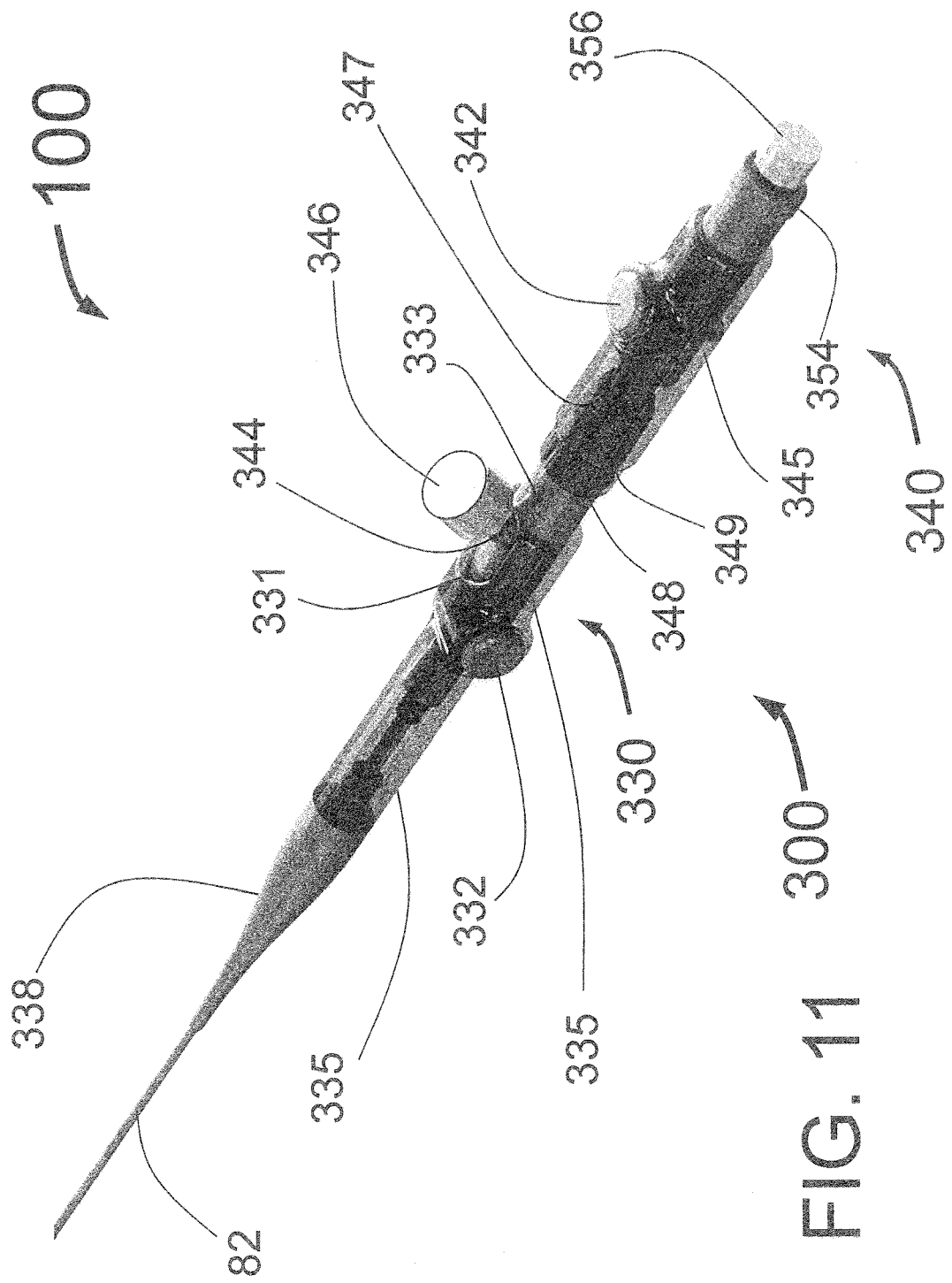
FIG. 11 is a schematic view of the handle that is situated at the proximal region of the PTAC.

Also shown in FIG. 4 is the penetration depth L2 which is the distance from the distal end 129 of the guide tube 115 to the center of the distal opening 117 located at the distal end of the injection needle 119. Mechanisms at the proximal end of the PTAC 100 (as shown in FIG. 11) control both the motion of the distal components such as the injector tubes 116 and guide tubes 115 as well as to limit and/or adjust the penetration depth L2 of the needles 119.

Figure 17:
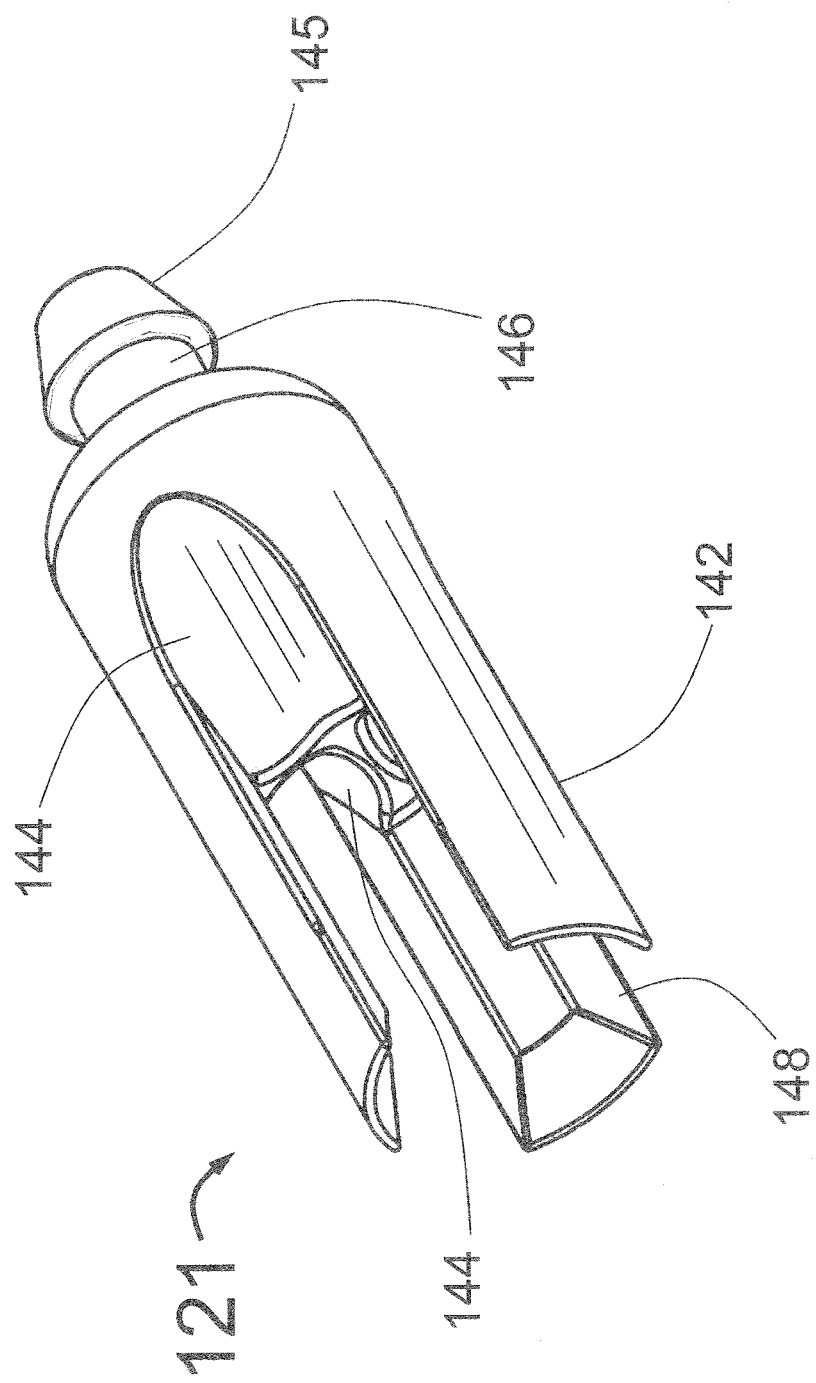
FIG. 17 is a schematic view of the central buttress component of the PTAC of FIGS. 2 through 11.

It is envisioned that the central buttress 121 and distal openings 131 can, as shown in FIG. 4, be separate components of the PTAC 100 or they can be formed as a single molded or machined part as is shown in FIG. 17. The distal tip 145 of the central buttress 121 provides the attachment to secure the buttress 121 to the tapered section 106. Additionally, 121,131, and 106 could be a single component molded or machined.

While the preferred embodiment of the PTAC 100 has the guide tubes 115 with a pre-formed curved shape, flexible naturally straight guide tubes are also envisioned where the buttress 121 forces the straight guide tubes to curve outward against the interior wall of the target vessel.

While the term "central buttress" will be used herein, the key component of the buttress 121 is the ramp 144 that provides radial and some lateral support for the deployed guide tubes 115. Specifically, the curved ramp 144 of the buttress 121 supports and guides the outward motion of the guide tubes 115 as they exit though the distal openings 131 and also provide radial support for the guide tubes 115 and injection tubes, as they engage the interior wall of the target vessel. Additional lateral support is provided by the fingers 142 of the central buttress 121.

The shape of the ramp 144 or the buttress 121 may include proximal extensions or fingers that create a smooth curved or inclined surface to steer the guide tubes 115 outward as the guide tubes 115 are advanced distally through the opening 131.

While the central buttress shown in FIG. 4 is a plastic part, a radiopaque metal part, such as stainless steel, or a plastic material that includes a radiopaque filler such as tungsten could be advantageously employed for showing the exact location where the guide tubes 115 will exit the PTAC 100. It is also envisioned that a radiopaque marker could be placed or attached to a portion of the openings 131 or buttress 121 or outer tube extension 104 to show the likely spot where the guide tubes 115 and thus the injection needles 119 would engage the interior wall of the target vessel.

Many of the components of the PTAC 100 are typically made from plastic materials such as polyamide, polyurethane, nylon or tecothane. These include the outer tube 102, middle tube 103 and inner tube 105, the outer tube extension 104, inner layer 127 and outer layer 123 of the guide tubes 115, the tapered section 106, the buttress 121, the guide tube connector 132 and the manifold 125. The manifold 125 can be a molded part or be epoxy or another resin that is injected to glue the injector tubes together within the lumen of the inner tube 105.

It is also envisioned that any or all of the inner tube 105, middle tube 103 or outer tube 102 could also be a metal hypotube or a metal reinforced plastic tube.

The injector tubes 116 would typically be made of a springy or shape memory metal such as nitinol. The radiopaque wire 118 and guide tube radiopaque marker 122 would be made of a radiopaque material such as gold, platinum or tantalum or an alloy of these or similar metals. The core wire 111 would typically be stainless steel and the outer layer 113 would be wrapped platinum or platinum iridium wire. The outer layer could also be a polymeric material. Any or certain portions of the outside of the PTAC 100 could be lubricity coated to provide improved performance. The injector tubes 116 and injection needles 119 should be smaller than 0.5 mm in diameter and preferably less than 0.3 mm in diameter to avoid any blood loss or leakage as the needles penetrate into the wall of the target vessel and are then removed.

FIG. 5 is the enlargement of section S5 of FIG. 3 showing the transition from the central portion to the distal portion of the PTAC 100 including the outer tube 102, middle tube 103 and inner tube 105 with injection lumen 133. Also shown is the connection between the outer tube 102 and the outer tube extension 104. While the manifold 125 in FIG. 5 shows the proximal end of the injector tubes 116 at a position distal to the proximal end of the manifold 125, it may be preferable for manufacturing the PTAC 100 with the proximal end of the injector tubes 116 located at or proximal to the proximal end of the manifold 125.

The guide tube connector 132 connects the three guide tubes 115 to the middle tube 103 that provides the impetus for advancement and retraction of the three guide tubes 115. The motion of the middle tube 103 is produced by the motion of control mechanisms at the proximal end of the PTAC 100. The manifold 125 lies inside of the distal portion of the inner tube 105 and connects together the three injector tubes 116 so that advancement and retraction of the inner tube 105 provides simultaneous advancement and retraction of the injector tubes 116. Also shown in FIG. 5 are the flushing spaces between the several tubes. Specifically shown is the outer annular space 137 between the middle tube 103 and the outer tube 102 and the inner annular space 139 between the inner tube 105 and the middle tube 103. Each of these spaces 137 and 139 are to be flushed through with normal saline solution prior to insertion of the PTAC 100 into the patient's body.

It is also visible in FIG. 5 how the proximal end of the injector tube 116 is in fluid communication with the injection lumen 133 of the inner tube 105. The radiopaque wire 118 which lies within the lumen of the injector tube 116 extends proximally from the proximal end of the injector tube 116 and is connected into the body of the manifold 125. It is also envisioned that instead of connecting into the body of the manifold 125, the three radiopaque wires could be welded together and/or attached to the proximal end of the manifold 125. Longitudinal motion of the inner tube 105 within the uniform diameter middle tube 103 causes the manifold 125 and attached injector tubes 116 to also move longitudinally. This longitudinal motion caused by control mechanisms near the proximal end of the PTAC 100 will advance and retract the injector tubes 116 through the lumens of the guide tubes 115 to expand outwardly to penetrate the wall of the target vessel to facilitate delivery of the ablative fluid.

FIG. 5 also shows how the three injector tubes 116 extend from the distal end of the inner tube 105 and manifold 125 and then enter the lumen of the inner layer 127 of the guide tube 115 at the proximal end of the guide tube 115. The guide tubes 115 and guide tube connector 132 are attached coaxially within the distal section of the middle tube 103. Thus longitudinal motion of the middle tube 103 will cause longitudinal motion of the guide tube connector 132 and guide tubes 115 thus allowing the mechanism at the proximal section of the PTAC 100 to advance and retract the guide tubes 115 with respect to the outer tube 102 and outer tube extension 104.

It is also envisioned that the penetration depth limitation could be a mechanism that limits the forward motion of the distal end of the inner tube 105 with respect to the guide tube connector 132. A ring or other structure situated between the distal end of the inner tube 105 or manifold 125 and the proximal end of the guide tube connector 132 would limit the forward (distal) motion of the distal end of the inner tube 105 and thus limit penetration of the needles 119 beyond the distal ends 129 of the guide tubes 115. Such a structure could be unattached, or attached to an internal structure of the PTAC 100 shown in FIG. 5 such as the inner tube 105, manifold 125, injector tubes 116, guide tube connector 132, proximal ends of the guide tubes or the middle tube 103. Such a structure could also have a length adjustment such as screw threads that would allow it to be used to adjust the penetration depth of the needles 119 beyond the distal ends 129 of the guide tubes 115.

FIG. 6 is a transverse cross-section at section 6-6 of the PTAC 100 as shown in FIG. 5. FIG. 6 shows the coaxial components of the main body of the PTAC 100 including the outer tube 102, the middle tube 103, the inner tube 105, the annular space 137 between the outer tube 102 and the middle tube 103 and the annular space 139 between the middle tube 103 and the inner tube 105. It also shows how the manifold 125 connects together the three injector tubes 116 with radiopaque wires 118 inside of the inner tube 105.

FIG. 7 is a transverse cross-section at section 7-7 of the PTAC 100 as shown in FIG. 5. FIG. 7 shows the coaxial orientation of outer tube 102 which connects distally to the outer tube extension 104 which lies outside of the middle tube 103. The guide tube connector 132 connects the three guide tubes 115 with inner plastic layer 127 that is situated inside of the guide tube connector 132 that is itself situated inside the middle tube 103. This construction allows the longitudinal motion of the middle tube 103 to cause similar motion in the connected guide tube connector 132 and guide tubes 115.

Figure 8:
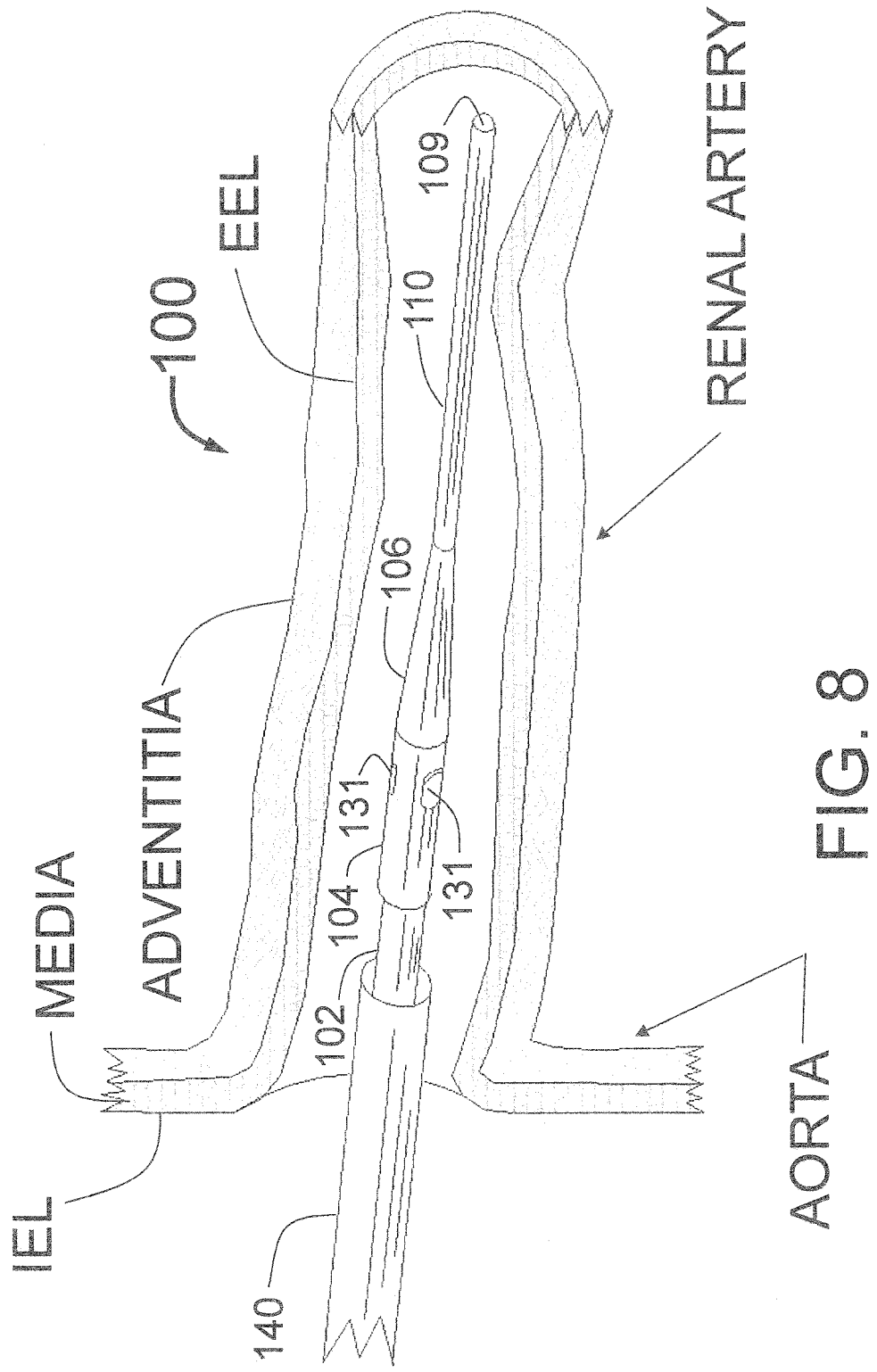
FIG. 8 is a schematic view of the distal portion of the manually expandable embodiment of the presently disclosed PTAC as it is advanced in its pre-deployment condition out of a guiding catheter into a renal artery.

FIGS. 8-11 are a set of schematic views that illustrate how the PTAC 100 is used for peri-vascular renal denervation. FIG. 8 shows a schematic view of a distal portion of the PTAC 100 in its pre-deployment configuration with outer tube 102, outer tube extension 104, tapered section 106 and distal fixed guide wire 110 with distal end 109. Two of the three distal openings 131 are also shown on the surface of the outer tube extension 104. In FIG. 8, the distal portion of the PTAC 100 has been pushed out of the distal end of the renal guiding catheter 140 to a position within the renal artery. Also shown are the Internal Elastic Lamina (IEL), media, External Elastic Lamina (EEL) and the adventitia of the renal artery and aorta. The PTAC 100 includes the central buttress 121 (not shown) that lies within the outer tube extension 104 located within a distal portion of the catheter body. The outer tube extension 104 has a distal opening 131 through which one of the three guide tubes 115 is advanced outwardly against the interior wall of the target vessel. The PTAC 100 further includes a closed position. The closed position has the distal end of the injection needles 119 being withdrawn into the guide tubes 115 and the guide tubes withdrawn 115 into the distal openings 131. The closed position can be an advantageous safety feature, and prevents needlestick injuries form the sharpened distal end of the injection needles 119.

Figure 9:
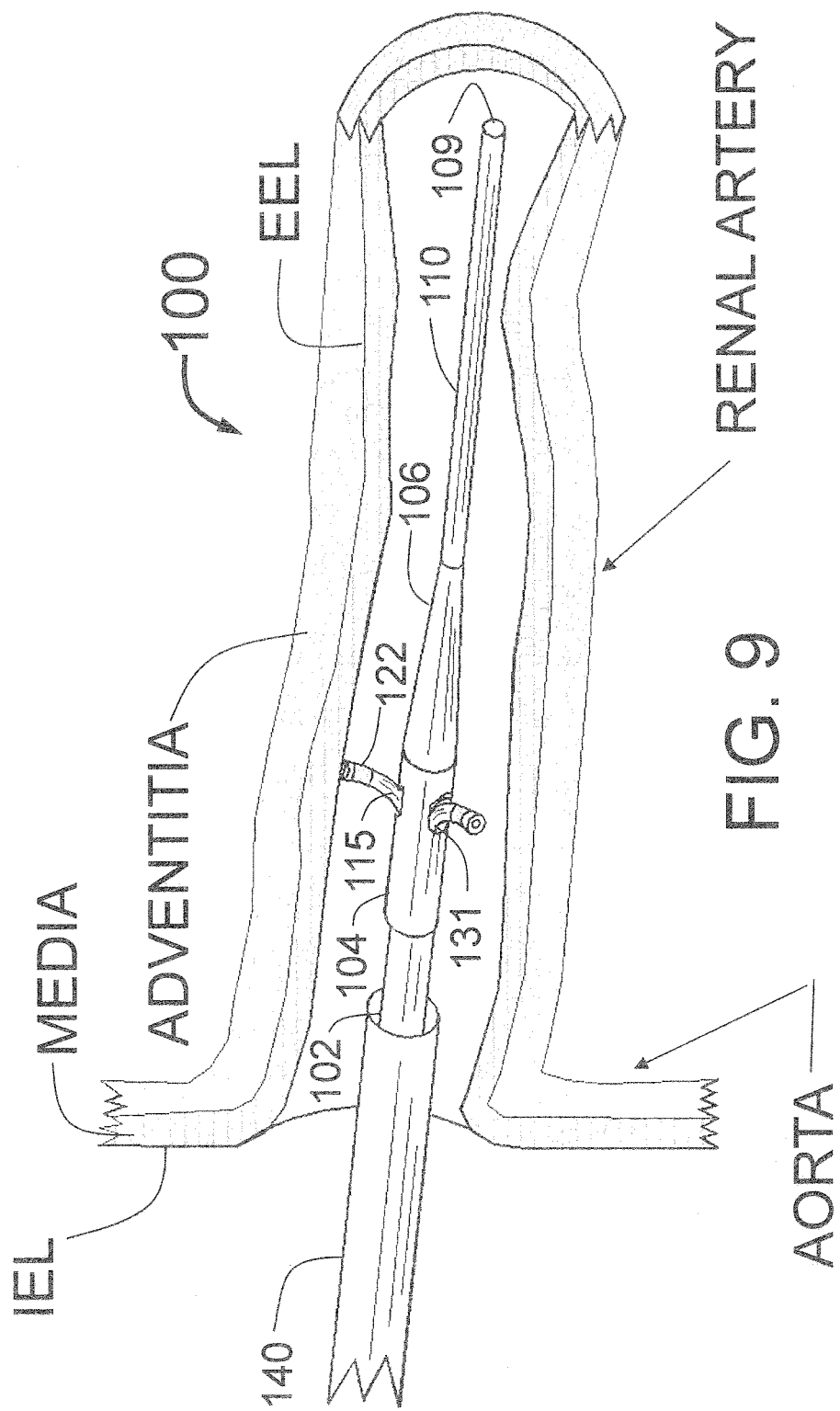
FIG. 9 is a schematic view of the distal portion of the manually expandable embodiment of the PTAC following manual advancement of the guide tubes against the interior wall of the renal artery.

FIG. 9 shows a schematic view of a distal portion of the PTAC 100 within a renal artery with the guide tubes 115 fully expanded outwardly against the interior wall of the artery. The guide tubes 115 move outward against the inside wall of the target vessel. The guide tubes are movable distally and proximally with respect to the distal portion of the PTAC 100. The guide tubes are manually movable and expandable. The longitudinal motion of the middle tube 103, see FIG. 5, can cause longitudinal motion of the guide tube connector 132 and guide tubes 115 thus allowing the mechanism at the proximal section of the PTAC 100 to advance and retract the guide tubes 115 with respect to the outer tube 102 and outer tube extension 104. The guide tubes 115 are supported radially and/or laterally by the buttress 121 (not shown) that lies within the outer tube extension 104. In some embodiments, the guide tubes 115 interact with a deflection surface such as the curved ramp 144 of the buttress 121 seen in FIGS. 3 and 4 to deflect outward and through the openings 131.

The renal artery and aorta are shown in cross-section so the lower guide tube 115 is actually touching a portion of the interior wall of the renal artery that is not shown because of the cross-section which splits the renal artery at 0 and 180 degrees. The third guide tube 115 is not seen as it is hidden behind the PTAC 100 but it too touches the interior surface of the renal artery wall. The radiopaque markers 122 on the guide tubes 115 allow the operator to visualize that the fully expanded guide tubes 115 are actually in contact with the interior wall of the renal artery. When the three guide tubes 115 are advanced outward, one guide tube 115 will touch the interior wall of the target vessel first and as the guide tubes are further advanced outward, this first touching guide tube will push the body of the PTAC 100 away from the wall toward the center of the vessel until the second guide tube 115 touches the interior wall of the target vessel. Then both touching guide tubes 115 will push the PTAC 100 further toward the center of the vessel until the third guide tube 115 touches the interior wall of the vessel. Because the guide tubes 115 here each the same diameter of expansion from the longitudinal axis of the PTAC 100, this will reproducibly place the distal portion of the PTAC 100 close to the true center of the vessel. Fluoroscopic imaging of the radiopaque markers 122 on the distal portion of the guide tubes provides visual confirmation of the correct centering of the guide tubes. This centering can also be confirmed by using contrast injected from the guiding catheter, after guide tube deployment. After centering, the guide tubes 115 are flush against the inside wall of the target vessel. It is generally advantageous to have the guide tubes 115 flush against the inside wall of the target vessel to provide the most radial and/or lateral support for the injector tubes 116 with distal injection needles 119. By providing radial and/or lateral support for the injector tubes 116 up to the inside wall of the target vessel, the distal injection needles 119 can be thin needles that will not cause blood loss. The thin needles may be flimsy and need such radial and/or lateral support provided by the guide tubes 115.

Of significance is that the emergence of the guide tubes 115 from the openings 131 in the outer tube extension 104 provides lateral support for the guide tubes 115 as they deploy outward. Radial support is provided by the central buttress 121 shown in FIG. 4. Together the radial and lateral support for the guide tubes, in some embodiments, are important in having the guide tubes expand uniformly resulting in a well centered distal portion of the PTAC 100 that is ready for deployment of the injection needles 119 seen in FIG. 10.

Some embodiments can include central buttresses, obturators and/or intraluminal centering mechanisms which provide lateral and/or radial support for the guide tubes 115. The mechanical support can be compact and/or longitudinally extending, reducing the diameter of the PTAC 100. The PTAC 100 is designed to allow much better blood flow. The catheter can be moved through the vessel without obstructing the blood flow through the vessel. In some embodiments, less than about 70%, 65%, 60%, 55%, 50%, 45%, 40%, 35%, 30%, 25%, or less of the cross-sectional lumen of the of the cross sectional area of the lumen of the target vessel is obscured. In some embodiments, the PTAC 100 obstructs less than 50% of the diameter and/or cross sectional area of the lumen, to prevent or minimize ischemia to distal organs and/or tissues. For Renal Denervation therapies for the treatment of hypertension, maintaining adequate blood flow to the kidneys, which in many cases are already somewhat compromised, can be important.

Figure 10:
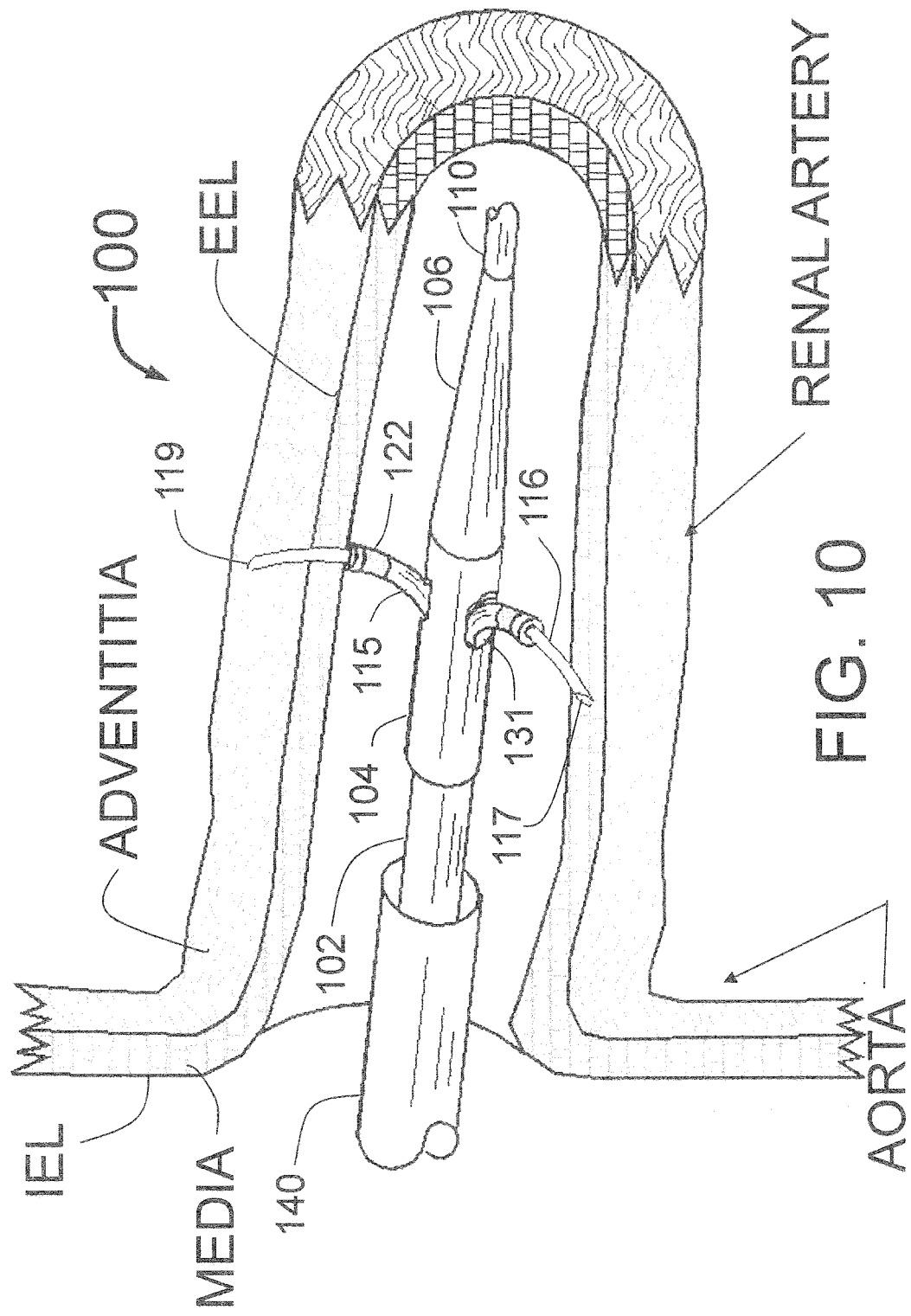
FIG. 10 is a schematic view of the distal portion of the manually expandable embodiment of the PTAC following advancement of the injector tubes with distal injection needles out of the guide tubes to the desired depth of penetration beyond the interior wall of the renal artery.

The guide tubes 115 can be expanded without obstructing or substantially obstructing the blood flow through the lumen. As shown in FIG. 10, the blood can flow around the PTAC 100 and around the guide tubes 115. The emergence of the guide tubes 115 from the openings 131 in the outer tube extension 104 provides lateral support for the guide tubes 115 as they deploy outward. Lateral and/or radial support is provided by the central buttress 121 shown in FIG. 4. The lateral openings 131 and the central buttress 121 provide sufficient radial and lateral support for the guide tubes without obstructing blood flow around the PTAC 100.

FIG. 10 shows a schematic view of a distal portion of the PTAC 100 within a renal artery with the injector tubes 116 with distal injection needles 119 fully deployed to deliver an ablative fluid into the peri-vascular space within and/or deep to the adventitia of the renal artery. The injector tubes 116 traverse the lumen of the guide tubes 115, and follow the curvatures of the guide tubes 115, toward the interior wall of the artery. The injector tubes 116 are supported laterally and/or radially by the guide tubes 115, the lateral openings 131, and the central buttress 121. The injector tubes 116 are expanded into the interior wall of the artery. In some embodiments, the needle distal openings 117 at or near the distal end of the injection needles 119 should be positioned beyond the EEL and toward the outside of the adventitia as shown for the upper needle 119 in FIG. 10. The third needle 119 and guide tube 115 are hidden behind the body of the PTAC 100 so they do not appear in FIG. 10. The sympathetic nerves which are the target for renal denervation lie within the adventitia or within several millimeters outside of the adventitia. Specifically a distance of 2-4 mm beyond the IEL is the appropriate position for the needle distal opening 117. If the sympathetic nerves are deeper, it is also envisioned that depths of 4 to 8 mm could be used.

The injection needle control mechanism 340 allows the user of the PTAC 100 to control the distal and proximal motion of the injector tubes 116 with distal injection needles 119. As mentioned above with respect to FIG. 9, the guide tubes 115 can each abut the tissue wall and reproducibly place the distal portion of the PTAC 100 close to the true center of the vessel. The injection needle control mechanism 340 can advance a plurality of injector tubes 116 simultaneously. The injector tubes 116 advance beyond the guide tubes 115 and into the tissue. The centering of the PTAC 100 can ensure that each injector tube 116 simultaneously advances to the same depth within the tissue. With predictable catheter centering, guide tube expansion, and injection needle expansion, the PTAC 100 achieves accurate and reproducible needle penetration to a targeted depth. Adjustment of the penetration depth by mechanisms in the proximal end of the PTAC may be either physician-controlled or they could be preset during device production. The depth limitation feature of some embodiments has the distal opening of the needles set to be a fixed distance beyond the distal end of the guide tubes. This prevents each needle from being accidentally set to different depths. The simpler design of the present application allows the needles to be delivered to equal depths.

FIG. 11 is a schematic view of an embodiment of the proximal section 300 (or handle) of the PTAC 100 having control mechanisms for advancing and retracting the needle guiding elements/guide tubes 115 and injector tubes 116 with distal needles 119 during the procedure to delivery an ablative fluid to the peri-vascular space. The handle 300 also has locking mechanisms activated by first and second controls such as press-able buttons 332 and 342. Specifically, button 332 when depressed unlocks the motion of the guide tube control cylinder 333 with respect to the outer tube control cylinder 335. The outer tube control cylinder 335 is attached to the outer tube 102. The transition section 338 provides strain relief to avoid kinks at the connection between the outer tube control cylinder 335 and the outer tube 102. The guide tube control cylinder 333 is attached to the middle tube 103 of FIGS. 2-7 that in turn is connected to the guide tubes 115 of FIGS. 2 through 10.

The guide tube control mechanism 330 allows the user of the PTAC 100 to control the distal and proximal motion of the guide tubes 115 and includes the button 332 and the guide tube control cylinder 333. The button 332 when depressed, unlocks the motion of the guide tube control cylinder 333 with respect to the outer tube control cylinder 335. This will allow the relative longitudinal motion of the middle tube 103 with respect to the outer tube 102 of FIGS. 3 through 7 which causes the advancement and retraction of the guide tubes 115. By pressing button 332 and/or pushing the guide tube cylinder 333 forward, the operator can cause the guide tubes 115 to move distally within the PTAC 100, interact with the buttress 121, and/or expand outward from the openings 131.

The injection needle control mechanism 340 allows the user of the PTAC 100 to control the distal and proximal motion of the injector tubes 116 with distal injection needles 119 and includes the button 342 and the needle control cylinder 345. The button 342 when depressed, unlocks the motion of the needle control cylinder 345 with respect to the guide tube control cylinder 333. This will allow the relative longitudinal motion of the inner tube 105 with respect to the middle tube 103 of FIGS. 3 through 7 which causes the advancement and retraction of the injector tubes 116 with distal injection needles 119 though the guide tubes 115. By pressing button 342 and/or pushing needle control cylinder 345 forward, the operator can cause the injector tubes 116 to move distally within the PTAC 100, interact with the buttress 121, and expand outward from the openings 131, traverse the lumen of the guide tubes 115, and/or expand outward from the end of the guide tubes 115.

The handle 300 shown in FIG. 11 has the flushing port 344. Port 344, which would typically have a Luer fitting, is shown with a cap 346. Port 344 is used to flush with saline the annular spaces 137 and 139 as shown in FIGS. 5 and 6. The injection port 354 which typically has an ablative fluid connector fitting is shown with cap 356. Port 354 allows injection of the ablative fluid into the lumen 133 of FIGS. 3 and 5 which is in fluid communication with the lumens of the injector tubes 116 which are in fluid communication with the needle distal openings 117.

Although FIG. 11 shows one flushing port 344, it envisioned that two or more flushing ports could be used to flush the internal spaces (other than the injection lumen) within the PTAC 100. It is also envisioned that a single button and cylinder mechanism could replace the two buttons 332 and 342. If this is the case, then a telescoping mechanism, internal to the proximal portion of the PTAC 100 would, upon advancement of the single button, first advance the guide tubes 115 then advance the injector tubes 116 with distal needles 119. Retraction of the single button would first retract the needles 119 and then retract the guide tubes 115.

While a standard Luer or Luer lock fitting could be used for the ablative fluid connector fitting for the injection port 354, in some embodiments of the presently disclosed PTAC 100, that a non-standard fitting can be used for injection of the ablative fluid. In other words, the non-standard fitting is different than the fitting of the flushing ports 344 and in some embodiments is a fitting other than the standard Luer or Luer lock fitting. The non-standard fitting can be a unique shape (e.g., square, triangular, oval, oblong, trapezoidal, irregular polygon, regular polygon, etc.). The non-standard fitting can have a unique coupling between the fitting and the mating syringe (e.g., key, detent, twist-lock, snap-fit, etc.). The non-standard fitting can have a unique size (e.g., larger or smaller diameter than the other fittings on the handle). Because of the ablative/toxic nature of the ablative fluid, having a non-standard fitting for the port 354 would reduce the chance of accidentally injecting the ablative fluid into one of the other ports (e.g. 344) or into the standard Luer fitting in the "Y" adapter typically used with a renal guiding catheter. It would also prevent the operator from the potential error of injecting flushing solution or other agents contained in a conventional Luer lock syringe, through the lumen of the injection tubes. It would also be an advantage for the non-standard fitting port 354 to have a smaller lumen than a standard Luer fitting so as to minimize the catheter dead space/internal volume.

A custom syringe with the non-standard fitting of the opposite sex designed to connect to the port 354 would be provided separately or within the PTAC 100 package. Such a syringe could contain exactly the correct volume for the appropriate amount of ablative fluid to achieve renal denervation, for example 0.25 ml of ethanol. Because the volume of tissue to be treated will vary with the diameter of the renal artery, several syringes of volumes ranging from 0.1 ml to 0.5 ml may be provided, each with a non-standard connector to connect to the injection port 354. If saline flushing, or the injection of other fluids (e.g., contrast or an anesthetic) are part of the procedure, additional syringes could be provided that contain the appropriate volume and type of fluid for visualization, flushing, renal denervation or for pain relief. It is envisioned that the ablative solution fluid injection syringe with a non-standard fitting could have a different color or distinct marking indicia as compared to the syringe for flushing through a port such as the port 344.

The handle 300 also includes a gap adjustment cylinder 348 that when rotated in one direction reduces the penetration depth L2 shown in FIG. 4 which is the distance the injection needles 119 extend beyond the distal ends 129 of the guide tubes 115. Rotation in the other direction of the cylinder 348 will increase the penetration depth L2. It is envisioned that the gap adjustment cylinder 348 could be accessible to the user of the PTAC 100 with markings on the handle 300 to indicate the distance that will be achieved. In a preferred embodiment of the handle 300, the gap adjustment cylinder 348 could be accessible only during assembly and testing of the PTAC 100 at the factory. This fabrication method is designed to ensure a properly calibrated penetration depth L2 of FIG. 4 that is preset in the factory during manufacturing and testing of each PTAC 100. This ability to accurately set and calibrate the penetration depth L2 can be advantageous, in some cases, to a good yield during manufacturing. In other words, even with variation of a few millimeters in the relative lengths of the components of the PTAC 100 such as the inner tube 105 and middle tube 103, the distance L2 can be dialed in exactly using the gap adjustment cylinder 348. In this preferred embodiment, the PTAC 100 would be labeled according to the penetration depth L2 shown in FIG. 4. For example, the PTAC 100 might be configured to have three different depths L2 of 2.5 mm, 3 mm and 3.5 mm. It is also envisioned that a set screw or other mechanism (not shown) could be included to lock the gap adjustment cylinder 348 at the desired penetration depth setting. While a gap adjustment cylinder 348 is shown here, it is envisioned that other mechanisms such as a sliding cylinder could also be used to adjust the depth L2.

The function of the handle 300 is to operate the PTAC 100 for Peri-Vascular Renal Denervation (PVRD). This procedure would include the following steps although not every step is essential and steps may be simplified or modified as will be appreciated by those of skill in this art:
1) Flush all of the internal volumes of the PTAC 100 with normal saline through the ports 344 and 354.
2) Insert the PTAC 100 through a previously placed guiding catheter 140 of FIGS. 8 through 10, positioning the distal portion of the PTAC 100 as shown in FIG. 8 at the desired location in one patient's renal artery.
3) Depress the button 332, and while holding the outer tube control cylinder 335 which is locked to the guide tube control cylinder 333, push the guide tube control cylinder 335 in the distal direction until the notch 331 engages the port 344 limiting the advance of the middle tube 103 of FIG. 5 and fully deploying the guide tubes 115 from inside the tubular shafts 120 and out through the openings 131 as shown in FIG. 9.
4) Release the button 332 which relocks the relative motion of the outer tube control cylinder 335 with respect to the guide tube control cylinder 333.
5) Depress the button 342 that allows relative motion of the injection needle control cylinder 345 with respect to the guide tube control cylinder 333 and while holding the outer tube control cylinder 335 (which is now locked to the guide tube control cylinder 333) advance the needle control cylinder 345 with distal end 349 until the penetration limiting mechanism stops the motion and the preset depth L2 of the needles 119 with respect to the distal ends 129 of the guide tubes 115. There are two ways this can be done: 1) The distal end 349 of the needle control cylinder 345 is pushed forward until it engages the guide tube flush port 344 or 2) the internal gap 347 is closed against the proximal end of the gap adjustment cylinder 348 inside the needle control cylinder 345.

6) Release the button 342 which relocks the motion of the injection needle control cylinder 345 to the guide tube control cylinder 333. This places the PTAC 100 in the configuration shown in FIG. 10 where the needles 119 penetrate through the internal elastic lamina (IEL) and penetrate to a preset distance (typically between 0.5 to 4 mm but preferably about 2-4 mm) beyond the IEL into the vessel wall of the renal artery. The depth of 2-3 mm will minimize intimal and medial renal artery injury. Depths as high as 8 mm may be needed for some unusual target vessels.

7) In this position a syringe or manifold with syringes (not shown) can be attached to the port 354 and the desired volume of ablative fluid is injected. The ablative agent which can be an ablative fluid, such as ethanol (ethyl alcohol), distilled water, hypertonic saline, hypotonic saline, phenol, glycerol, lidocaine, bupivacaine, tetracaine, benzocaine, guanethidine, botulinum toxin, glycosides or other appropriate neurotoxic fluid. This could include a combination of 2 or more neuroablative fluids or local anesthetic agents together or in sequence (local anesthetic first to diminish discomfort, followed by delivery of the ablative agent) and/or high temperature fluids (or steam), or extremely cold (cryoablative) fluid into the vessel wall and/or the volume just outside of the vessel. A typical injection would be 0.1 to 5 ml. This should produce a multiplicity of ablation zones (one for each injection needles 119) that will intersect to form an ablative ring around the circumference of the target vessel. Contrast could be added to the injection either during a test injection before the neuroablative agent or during the therapeutic injection to allow x-ray visualization of the ablation zone. With ethanol, as an ablative agent, a volume of less than 0.5 ml is sufficient for this infusion as it will not only completely fill the needed volume including the sympathetic nerves, but is small enough that if accidentally discharged into the renal artery, would not harm the patient's kidneys. Ideally, a volume of 0.1 ml to 0.3 ml of ethanol should be used. The amount used could be the same for all renal arteries or it could vary depending on the diameter of the renal artery into which the ethanol is to be injected. The agrophobic and lipophilic nature of ethanol enhances the spread allowing such a small volume to be effective. It is desirable to fluoroscopically verify the deployment of the needles 119 of FIGS. 2-4 into the vessel wall of the target vessel before injecting the ablative agent or fluid.

8) Next a syringe with normal saline solution is attached to the port 354 replacing the ablative fluid syringe. Ideally, slightly more saline is injected than the total volume of dead space to ensure there is no ablative fluid left in the PTAC 100. For example, if the dead space in the PTAC 100 is 0.1 ml then for example 0.1-0.15 ml of saline would be a good amount to ensure the ablative fluid is all delivered through the needle distal openings 117 of the injection needles 119 of FIG. 10 to the appropriate peri-vascular volume of tissue.

9) Depress the button 342 and while holding the outer tube control cylinder 335, pull the needle control cylinder 345 back in the proximal direction until the injection needles 119 are fully retracted back into the guide tubes 115. It is envisioned that a click or stop would occur when the injection needle control cylinder 345 reaches the correct position so that the injection needles 119 are fully retracted.

10) Release the button 342 locking the motion of the injection needle control cylinder 345 to the guide tube control cylinder 333.

11) Depress the button 332 releasing the relative motion of the outer tube control cylinder 335 with respect to the guide tube control cylinder 333 that is now locked to the injection needle control cylinder 345.

12) Retract in the proximal direction the guide tube control cylinder 333 with respect to the outer tube control cylinder 335. This will retract the guide tubes 115 of the configuration of FIG. 9 back inside the openings 131 in the outer body extension 104 the PTAC 100.

13) Pull the PTAC 100 back into the guiding catheter 140.

14) Move the guiding catheter 140 to the other renal artery.

15) Repeat steps 3 through 13 for the other renal artery.

16) Remove the PTAC 100 from the body.

It may also be highly desirable to eliminate step 8, and also in step 1 flush the internal volume/dead with the ablative fluid outside the body, instead of saline. This would be done with the guide tubes 115 and needles 119 fully deployed. It may also be desirable if this technique is used to rinse the distal portion of the PTAC 100 in saline prior to advancement of the catheter into the body in order to remove any of the ablative fluid from the surface of the PTAC 100 that might have been retained on the surfaces of the catheter during the flushing with the ablative fluid.

While the buttons 332 and 342, as described above, release the motion of control cylinders when depressed and lock when released, it is also envisioned that they could also be interlocked as follows:

1. The first interlock allows the injection needle control cylinder 345 to be unlocked only when the guide tube control cylinder 333 is in its most distal position where the outer tube 102 is pulled back and the guide tubes 115 are fully deployed.
2. The second interlock allows the guide tube control cylinder 333 to be unlocked only when the injection needle control cylinder 345 is in its most distal position where the needles 119 are retracted within the guide tubes 115.

The combination of the buttons 332 and 342 with the control mechanisms described above should make the use of the PTAC 100 reasonably simple and straight forward. The operator basically presses button 332 and pushes the guide tube cylinder 333 forward causing the guide tubes 115 to expand outward, then presses button 342 and advances the needles 119 forward to penetrate the wall of the renal artery. Injections are performed then the reverse procedure is done with button 342 depressed and the needles 119 retracted, then button 332 is depressed and the guide tube cylinder 333 is retracted in the proximal direction retracting the guide tubes 115 within the body of the PTAC 100.

While a push button activated handle where sections are pushed and pulled in the longitudinal direction to cause guide tube and needle deployment is shown in FIG. 11, it is envisioned that other techniques such as rotational mechanisms for locking or longitudinal motion can also be used. The Fischell et al U.S. patent application Ser. No. 13/643, 070 filed Oct. 23, 2012, which is hereby incorporated by reference in its entirety, shows such a rotational locking mechanism in FIG. 33.

It is also envisioned that although flushing and filling the injection lumens with normal saline as described in step 8 of the method above has the advantage of not allowing any of the toxic ablative fluid to accidentally be introduced into the renal artery during the procedure, another technique is possible with a low dead space PTAC 100. Specifically if the dead space is small, and the ablative fluid is ethanol, hypertonic or hypotonic saline, then the ablative fluid can be used to fill the dead space out of the body. Because of mixing with large amounts of blood going to the kidney, direct injection of even 0.5 ml of ethanol, hypertonic or hypotonic saline will not harm the kidney. This concept then eliminates the flush step after injection of the ablative fluid reducing the injection steps in the procedure from 2 per artery to one per artery. For example, if the dead space is 0.1 ml and the desired injection volume of ethanol is 0.2 ml then 0.1 ml of ethanol could be used to fill the dead space outside of the body. Then the catheter and needles would be deployed in the first renal artery. Then 0.2 ml additional ethanol would be injected which will deliver 0.2 ml into the peri-vascular space leaving 0.1 ml in the dead space. The needles 119 and guide tubes 115 are retracted, the PTAC 100 is deployed in the other renal artery and another 0.2 ml of ethanol would be injected. The needles 119 and guide tubes 115 are retracted and the PTAC 100 is removed from the body. In this abbreviated procedure, very little (<0.05 ml) ethanol should leak out into the renal artery and 10 times that amount will still not harm the kidney. Another advantage of this reduced step process is that only ablative fluid is delivered to the peri-vascular space which reduces the "dilution" of the ablative fluid by the volume of saline in the dead space that would be delivered first in the procedure above before the ablative fluid can be delivered.

It should also be noted that in one variation of the procedure having the cap 356 locked onto to the fitting for the injection port 354 prior to placing the PTAC 100 into the patient's body will certainly prevent any ablative solution from entering the renal artery during insertion of the PTAC 100 into the renal artery. Additionally, replacing that sealing cap 356 onto the fitting for the injection port 354 as the PTAC 100 is moved from one renal artery to the opposite renal artery will also prevent any ablative solution from entering the second renal artery. The cap 356 would also be locked onto the fitting for the injection port 354 as the PTAC 100 is removed from the patient's body. During the renal denervation procedure, the cap 356 would be removed only to inject ablative solution into the peri-vascular space of the treated vessel.

A stopcock attached to the port 354 could also be used such that when closed, it would prevent leakage of ablative fluid out of the needle distal openings 117 of FIGS. 2 through 10. In reality of course, if there were no cap 356 attached as the PTAC 100 is moved within the arterial system of the body, the blood pressure within the arterial system would if anything force any fluid within the injection lumens of the PTAC 100 back out of port 354.

It is also envisioned that one could have any combination of use or non-use of flushing steps. For example, the PTAC 100 dead space could be prefilled with the ablative fluid, and then saline solution could be used to flush the ablative fluid into the peri-vascular space following deployment of the needles 119 and guide tubes 115. After the ablative fluid has been injected into the peri-vascular space, the needles 119 and guide tubes 115 could be retracted out of the peri-vascular space and the dead space could be refilled with ablative fluid flushing the saline out of the dead space. The other renal artery could then be treated.

The PTAC 100 can be packaged with the guide tubes 115 fully extended and the injector tubes 116 fully retracted. The reason for this is that the preferred embodiment of the guide tubes are made from plastic such as polyimide formed into a curve shape. Such a plastic material may lose its shape if it were packaged retracted back into the tubular shaft 120 which would straighten it. It is also possible to ship the device with the needles 119 at the distal end of the injector tubes 116 fully expanded as well to ensure maximum shape retention of the guide tubes 115 and the injector tubes 116. In this case, the device would be shipped in a protective housing to ensure handlers do not receive needle sticks.

It should also be understood that the handle 300 in FIG. 11 has a distal portion that has a tapered cone structure 338 that is attached to a hypotube 82, which hypotube 82 extend for most of the length of the PTAC 100. As shown in FIG. 18, the hypotube 82 is connected to a connecting tube 92 that is joined at its distal end to the outer tube 102 of the PTAC 100. A hypotube is typically made from the same type of metal as a hypodermic needle, e.g., typically a stainless steel.

Figure 12:
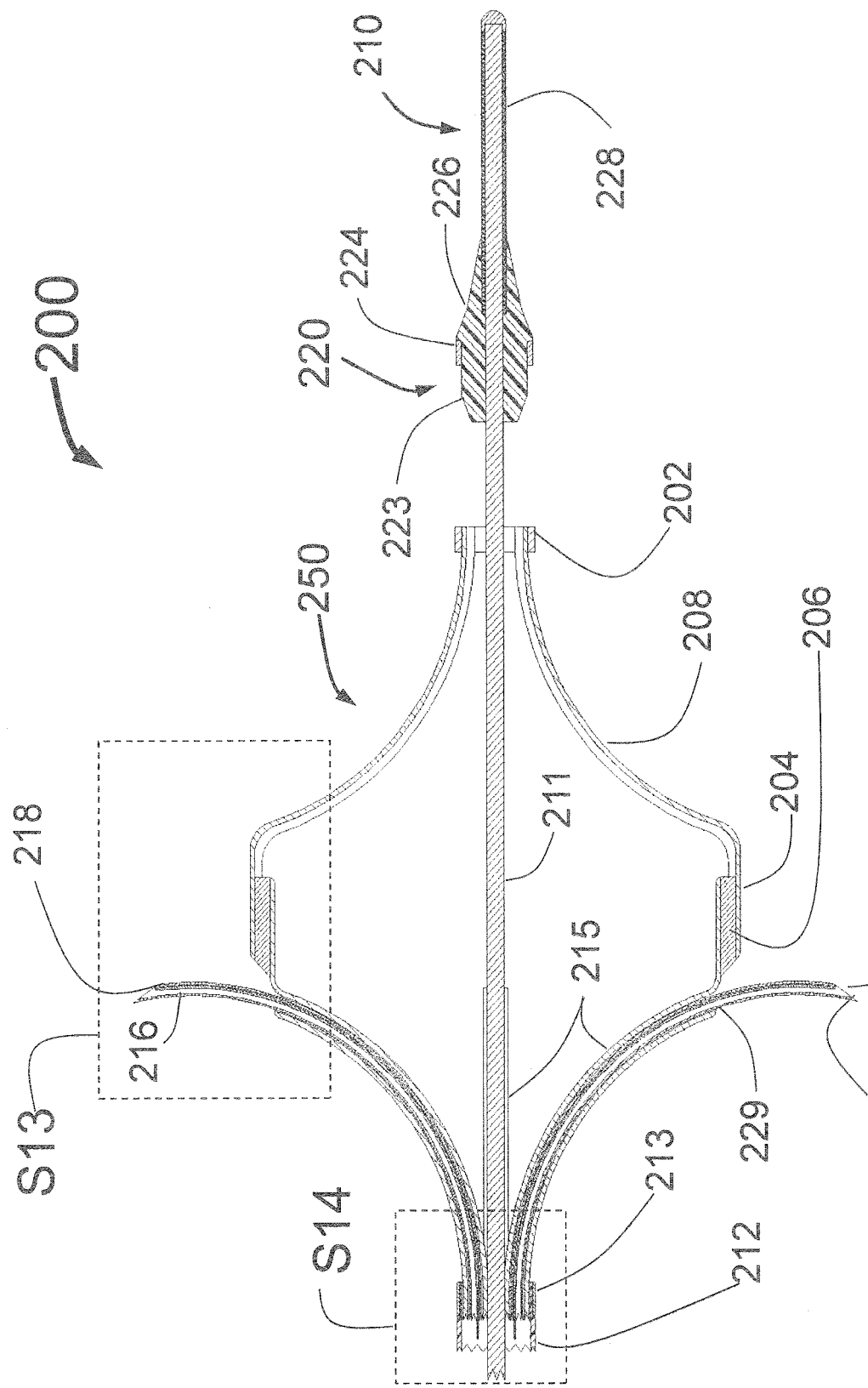
FIG. 12 is a cross-section of a distal section of an intraluminal centering mechanism (ICM) which is an alternative embodiment showing a wire basket with radiopaque markers that can be used to provide radial and lateral support for the guide tubes through which injector tubes with distal needles are advanced against and through the interior wall of a vessel such as the renal artery.

FIG. 12 is a longitudinal cross-section of alternative embodiment of the PTAC 200 with self-expanding guide tubes 215 supported by an Intraluminal Centering Mechanism (ICM) 250 that assists in both uniformity of expansion of the self-expanding guide tubes 215 as well as providing addition support for the guide tubes 215. The central portion 204 of the ICM 250 will provide a larger surface to open against the interior wall of the target vessel to prevent the distal ends 229 of the guide tubes 215 from backing away from the interior wall of the target vessel or moving laterally as the injector tubes 216 with distal injection needles 219 are advanced outwardly through the vessel wall. As with the PTAC 100 of FIGS. 2 through 11, the guide tubes 215 are the needle guiding elements that expand outwardly to provide support/backup for the injection needles 219 at the distal end of the injector tubes 216 as they are advanced through to penetrate the interior wall of the target vessel. This support or backup, in some cases, is an important feature of this alternative embodiment of the PTAC 200 as shown in FIG. 12 compared with the prior art PTAC 50 embodiment shown in FIG. 1. The PTAC 200 shown in FIG. 12 includes an obturator 220 having proximal section 223, distal tapered section 226 and radiopaque marker band 224. Distal to the tapered section 226 is a fixed guide wire 210 with core wire 211 and outer layer 228. A radiopaque wire 218 inside the lumen of each injector tube 216 provides enhanced radiopacity for the injector tubes 216 so that their deployment can be visualized under fluoroscopy.

The PTAC 200 of FIG. 12 has four guide tubes 215 with four concentric injector tubes 216. Ideally 3-5 needles should be used for renal denervation. With ethanol as the ablative fluid for neural ablation, three needles may be sufficient because of the hydrophilic nature of ethanol which can readily spreads within human tissue.

The core wire 211 provides connectivity with the central section of the PTAC 200 and extends distally to form the core of the fixed guide wire 210. Fixed wire devices and the formation of guide wires are well known in the art of medical devices.

The ICM 250 includes a distal ring 202, support struts 208, central portion 204 with radiopaque marker 206. The ICM 250 provides additional radial and circumferential/lateral support for the guide tubes 215 both during expansion and during advancement of the injector tubes 216 through the guide tubes 215. The outside of the central portion 204 also provides a small but flat or slightly curved surface to engage or touch the interior wall of the target vessel that can reduce the trauma to the vessel wall as compared with having the ends of the guide tubes 215 touch the wall. As can be seen in FIG. 12, the surfaces 204 would touch the wall of the vessel before the ends of the guide tubes 215 would touch that wall. This design provides a broader surface in contact with the vessel wall and that would eliminate any tendency for the distal end 229 of the guide tubes 215 to damage the wall of the target vessel.

It is envisioned that there are several techniques for creating the structure of guide tubes 215 attached to a distal ICM 250 as shown in FIGS. 12 and 13. One technique is to take a nitinol tube which will be formed into the shape seen in FIG. 12. Once heat set in this shape, a machining process would remove material to expose the distal ends 229 of the guide tubes 215. A second machining process would remove half of the cylinder say from 90 to 270 degrees of a portion of the ICM 250 of the PTAC 200. A radiopaque plug 206 would then be attached within the horizontal section 204 and the distal end of the ICM 250 would be attached to the ring 202.

An alternative technique would have the guide tubes 215 made of plastic and a nitinol flat wire having three sections including a proximal section attached to the plastic tube a central portion with a flat horizontal shape and a distal curved ICM portion.

A sheath 212 with radiopaque marker band 213 is shown in FIG. 12 in its proximal or open position having been retracted to allow the self-expanding guide tubes 215 to expand outward. The radiopaque markers 206 allow fluoroscopic visualization to confirm the appropriate expansion of the guide tubes 215 against and/or in close proximity to the interior wall of the target vessel. The injector tubes 216 with distal injection needles 219 and distal opening 217 are then advanced through the guide tubes 215 to penetrate the interior wall of the target vessel. Ablative fluid is then injected through the needle distal openings 217 into the peri-vascular space. The injector tubes 216 are then withdrawn back into the guide tubes 215 and the sheath 212 is advanced in the distal direction to collapse the guide tubes 215 and the ICM 250. When the radiopaque marker band 213 near the distal end of the sheath 212 is adjacent to the radiopaque marker 224 on the obturator 220, the operator can confirm that the PTAC 200 is in its closed position and retract it back into the guiding catheter.

FIG. 13 is a longitudinal cross-section enlargement of section S13 of FIG. 12 showing the structure of the fully deployed PTAC 200. The injector tubes 216 with distal injection needles 219, needle distal opening 217 and radiopaque wire 218 are shown coaxially advanced out of the distal end 229 of the guide tube 215 with the ICM 250 attached. The ICM 250 has a central portion 204 with radiopaque marker 206. The central portion 204 has a proximal end that is fixedly attached the guide tube 215 on its distal end. The central portion 204 is shown in FIG. 13 formed integral with the support strut 208 connecting at the distal end of the central portion 204.

The guide tubes 215, central structure 204 and support struts 208 are formed from a shape memory alloy or springy metal such as nitinol. Specifically, in the embodiment shown in FIGS. 12 and 13, a single tube of nitinol is machined and then bent and heat set to form the configuration shown in FIGS. 12 and 13. The guide tubes 215 are cylindrical as is the central section 204 which has a radiopaque marker 206 attached to it. The support struts 208 have a portion of the cylinder removed.

It is also envisioned that the guide tubes 215 could be plastic such as shown in FIGS. 1-10 with a round or flat nitinol wire attached to the guide tube 215 to enhance the self-expansion characteristics of the plastic and extend distally to form the ICM support struts. It is also envisioned that different variations in the structure of the guide tubes 215 can be used to make the guide tubes more flexible. For example, a helical laser cut out along the length of the guide tube 215.

Figure 14:
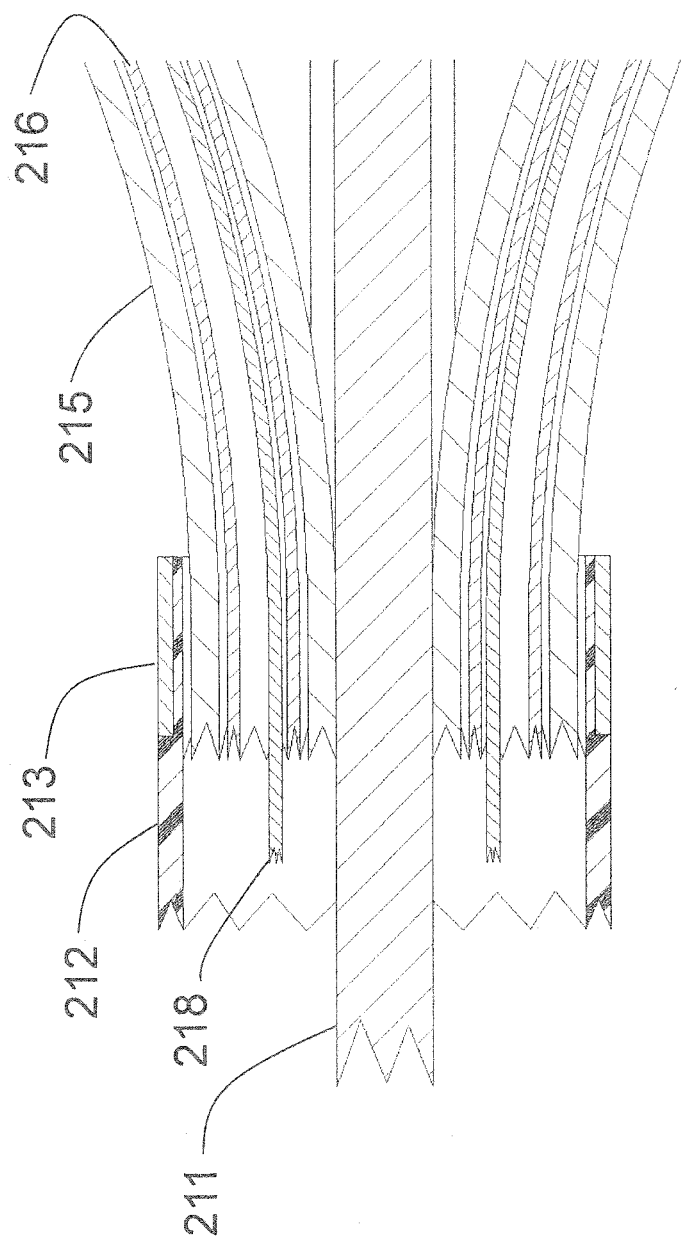
FIG. 14 is an enlargement of the region S14 as shown in FIG. 12.

FIG. 14 is an enlargement of the longitudinal cross-section of section S14 of the PTAC 200 of FIG. 12. FIG. 14 shows the sheath 212 with distal radiopaque marker band 213. Also shown are the guide tubes 215, the injector tubes 216, the radiopaque wire 218 and the core wire 211. The central and proximal sections of the PTAC 200 are shown in the prior disclosures of U.S. patent application Ser. Nos. 13/294,439 and 13/342,521. This includes the mechanisms near the proximal end of the PTAC 200 that allow the operator to retract the sheath 212 allowing the guide tubes 215 to expand outward against the interior wall of the target vessel. This also includes the mechanism that controls the advancement of the injector tubes 216 with distal injection needles 219 through the guide tubes 215 and into the wall of the target vessel.

Fischell et al. in U.S. patent application Ser. No. 13/643, 070 shows several handle/proximal section configurations specifically designed to release self-expanding guide tubes and advance injection needles into or deep to (outside of) the adventitia of a target vessel. Such designs would work well in conjunction with the PTAC 200 of FIGS. 12 through 14.

While the PTAC 200 of FIGS. 12 through 14 show a self-expanding guide tube structure, it is envisioned that an ICM could be added to the manually expanded PTAC 100 of FIGS. 2-10 to further enhance the support and backup of the guide tubes against the interior wall of the target vessel.

In some embodiments, an important feature of the PTAC 200 of the present application is the use of radial and lateral/circumferential support structures for the needle guiding elements/guide tubes 115 and guide tubes 215 of FIG. 4 and FIG. 12. These include the tubular shafts 120 with openings 131 and central buttress 121 to provide both radial and lateral support for the guide tubes 115 of FIG. 4 and the ICM 250 of FIG. 12 to provide radial and lateral support for the guide tubes 216.

Figure 15:
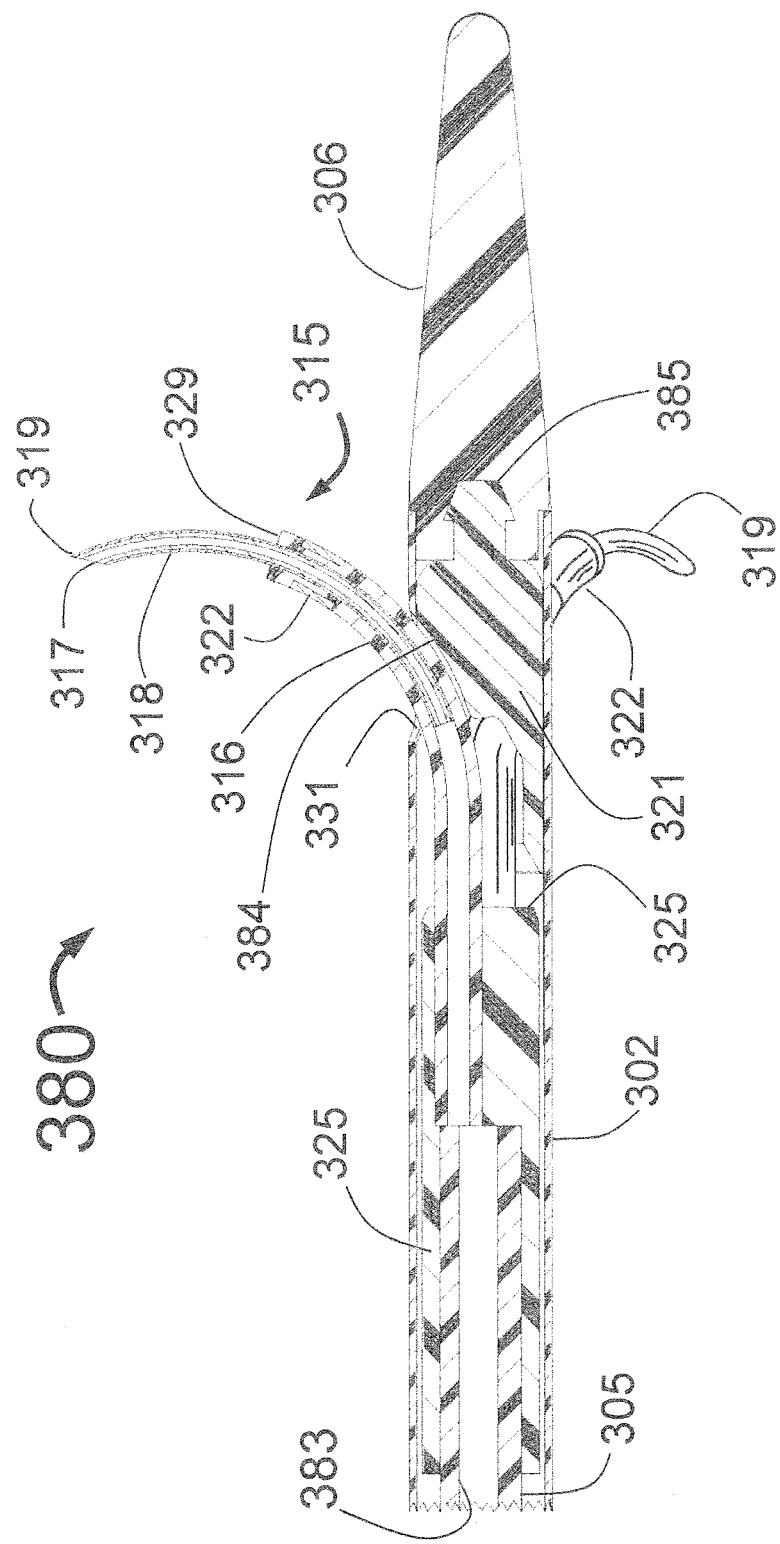
FIG. 15 is a longitudinal cross-section of a distal portion of an alternative embodiment where the guide tubes and injector tubes of the PTAC are combined into a single injector tube assembly which is advanced to penetrate the wall of the target vessel.

FIG. 15 is a longitudinal cross-section of PTAC 380 which is another embodiment of the present application. This design has the guide tubes 316 and injector tubes 318 combined into a single injector tube assembly 315 with radiopaque marker 322, distal end 329 and distal injection needle 319 having distal opening 317 and a gold plating on the outside of the injector tubes 318 to enhance visibility of the needles 319 under fluoroscopy. The PTAC 300 has a distal tapered nose 306, outer tube 302 with openings 331 through which the injector tube assembly 315 is advanced.

The PTAC 380 also has an inner tube 305 with injection lumen 383 which is in fluid communication with the lumens of the injector/guide tube assemblies 315 which is in fluid communication with the lumen of the injection needle 319. The inner tube 305 is attached to the injector/guide tube assembly 315 through the manifold 325. The central buttress 321, similar to that of the central buttress 121 of FIGS. 3 and 4, provides the ramp 384 that deflects the injector tube assembly 315 outward and provides radial support for the penetration of the interior wall of the target vessel by the injection needles 319.

The distal nose 385 of the central buttress 321 provides the attachment for the nose 306. The outer tube 302, distal nose 306 or central buttress 321 may also include radiopaque markers or be made from a plastic with a radiopaque filler such as tungsten filled polyurethane. The central buttress 321 can extend a sufficient distance in the proximal direction so that the needle distal opening 317 can be completely withdrawn within the body of the PTAC 380 to avoid needlestick injuries to users of the PTAC 380.

The distal nose 306 would preferably be made from a relatively low durometer or soft plastic. The needles 319 can be made from any metal that will hold its shape although cobalt chromium alloys such as L605 or a shape memory metal alloy such as nitinol are preferred.

It is also envisioned that the PTAC 380 could have a distal fixed guide wire like the PTAC 100 of FIG. 3 or be configured to be delivered over a guide wire in either an over-the-wire or rapid exchange configuration. Similarly, the PTAC 100 of FIGS. 2-11 or the PTAC 200 of FIGS. 12 through 14 could use a soft nose similar to the nose 306 of FIG. 15 instead of a fixed guide wire 211 as shown for other embodiments disclosed in the present application.

The PTAC 380 can be substantially similar to the PTAC 100, and can be used in substantially similar manner as described herein. The PTAC 380 has the advantage of one less step in delivery of the needles as compared to the PTAC 100 of FIGS. 2-11. After positioning the distal end of the PTAC 380 at the desired site, the operator can advance the inner tube 305 with respect to the outer tube 302 using a mechanism at the proximal end of the PTAC 380. This will push the injector tube assemblies 315 forward and outward as deflected by the ramps 384 of the central buttress 321 and out of the openings 331 in the outer tube 302. The needles 319 will penetrate the interior wall of the target vessel limited in penetration by the distal ends of the injector/guide tube assemblies 315. The combination of the radiopaque marker bands 322 on the assemblies 315 and the gold plating on the needles 319 allows the user to visualize the deployment of the PTAC 380 for delivering an ablative fluid into the peri-vascular space.

In this embodiment of the PTAC 380, the injector/guide tube assemblies 315 are the needle guiding elements that expand outward to provide support/backup for the injection needles 319 as they are advanced through the wall of the target vessel.

Figure 16:
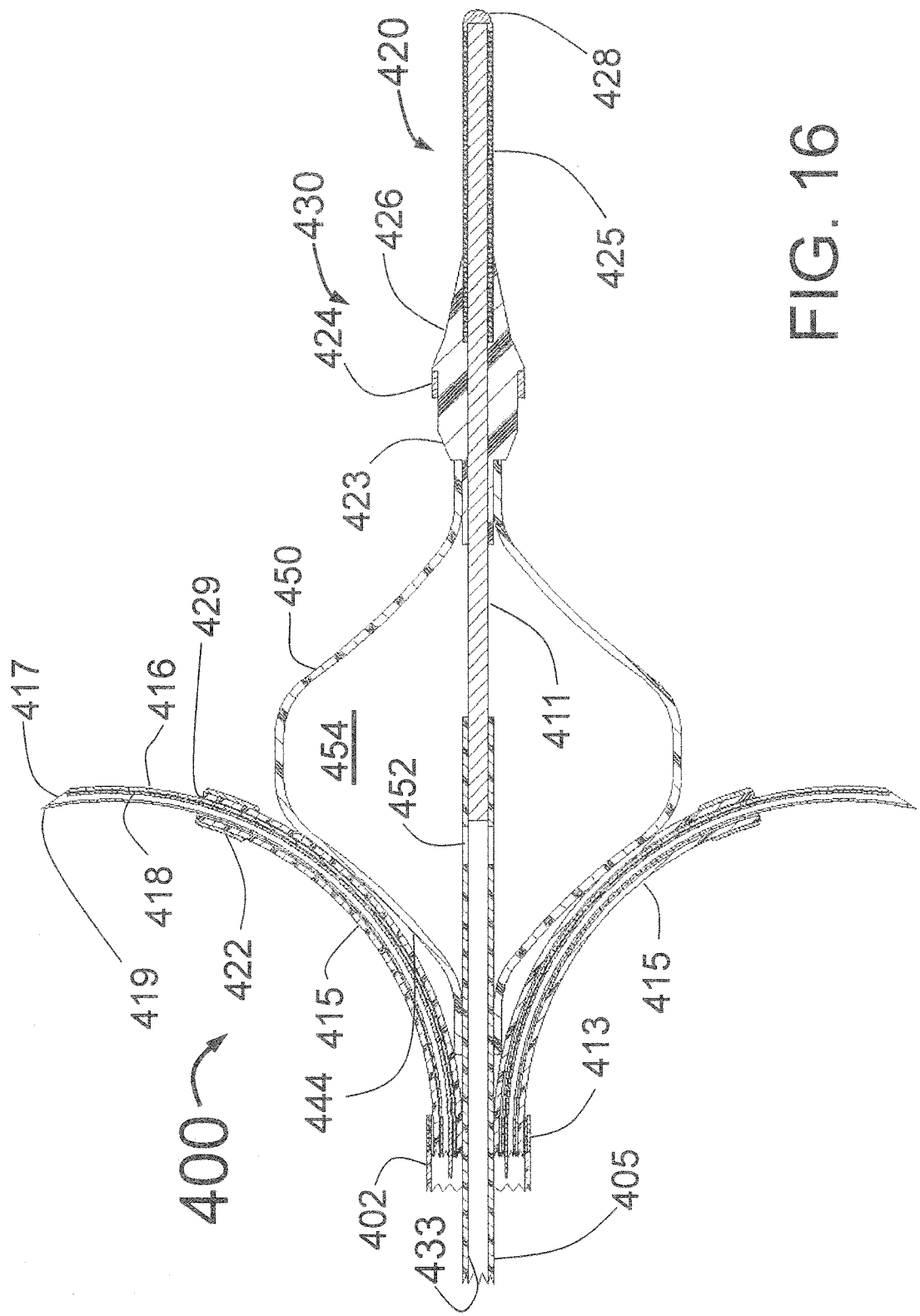
FIG. 16 is a longitudinal cross-section of still another embodiment which uses an inflatable balloon to move outward and provide radial and lateral support for the guide tubes as they engage the interior wall of the target vessel.

FIG. 16 is a longitudinal cross-section of the distal portion of still another embodiment of the presently disclosed PTAC 400, which uses an inflatable balloon 450 to expand the four guide tubes 415 outward to engage the interior wall of the target vessel. Three to eight guide tubes are envisioned for this design with three being preferred for delivery of ethanol for renal denervation. The balloon 450 can be a cylindrical balloon. The balloon 450 can be designed to avoid obstructing blood flow within the target vessel, even when expanded, as described herein. It can also be a non-compliant balloon to ensure luminal space between the outside of the balloon and the inside wall of the target vessel for blood to flow.

The PTAC 400 has a distally attached fixed guide wire 420 with outer layer 425, core wire 411 and distal tip 428. FIG. 16 shows the PTAC 400 in its fully open position with guide tubes 415 with radiopaque markers 422. Coaxially within the guide tubes 415 are injector tubes 416 with sharpened distal injection needles 419 with distal openings 417 deployed outward beyond the distal ends 429 of the guide tubes 415. A radiopaque wire 418 lies within the lumen of the injector tube 416 to reduce the dead space and provide enhanced visibility.

The distal portion of the PTAC 400 has the tapered section 426, radiopaque marker band 424 and proximal portion 423. This tapered unit, including elements 423, 424 and 426, is called an obturator 430. The obturator 430 is attached to the fixed guide wire 420 with tip 428, outer layer 425 and core wire 411. Other important features, in some cases, of this alternative embodiment are the radiopaque marker band 413 on the sheath 402 that in combination with the radiopaque marker band 424 on the obturator 430, provides indication of the position of the distal end of the sheath 402 relative to the obturator 430 so that the operator readily knows whether the PTAC 400 is in its closed position with the sheath 402 in its fully distal position and the guide tubes 415 and injector tubes 416 are thereby fully enclosed.

The preformed radius of curvature of the injector tubes 416 should be similar to that of the guide tubes 415 so that the guide tubes 415 will maintain their position against the interior wall of the target vessel as the injector tubes 416 with distal injection needles 419 are advanced to penetrate the interior wall of the target vessel. Specifically, the radius of curvature of the central axis of the distal portion of the injector tube 416 should be approximately the same as the radius of curvature of the central axis of the guide tube 415. The radii of curvature of the central axes of the guide tubes 415 and the injector tubes 416 can be within 1 mm of each other, or within 0.2 mm of each other. Although a curved shape with a single radius of curvature is shown in FIG. 16, curved shapes of the guide tubes 415 and injector tubes 416 could have two or more portions each with a different radius of curvature. Even if two or more different radii of curvature are used for these components, it can be advantageous that when fully deployed, the curved shape of the injector tube 416 is such that its longitudinal axis is coaxial to the longitudinal axis of the lumen of the curved portion or portions of the guide tube 415. In other words, the advanced injector tube 416 can in some embodiments fit perfectly within the advanced guide tube 415. It is also envisioned that if the radii of curvature are significantly different then the radius of curvature of the injector tube 416 should be less than the radius of curvature of the guide tube 415 so that when the injector tube 416 is advanced it will not push the guide tubes 415 away from the interior wall of the vessel. Another way to characterize the two radii of curvature is that they should be, in some cases, within about 20% of each other and in some embodiments within 5%.

As with the PTAC 100 of FIGS. 2 through 11, the guide tubes 415 are the needle guiding elements that expand outwardly to provide support/backup for the injection needles 419 at the distal end of the injector tubes 416 as they are advanced through the needle guiding elements to penetrate the wall of the target vessel.

FIG. 16 shows an inflatable balloon 450 attached at its proximal end to the tube 405 and at its distal end to the obturator 430. Side holes 452 in the inner tube 405 provide fluid communication between the inflation lumen 433 of the inner tube 405 and the interior space 454 of the inflatable balloon 450. There are envisioned several embodiments in which the balloon 450 would provide mechanical support for the guide tubes.

In a first embodiment the guide tubes 415 are fixedly attached to the proximal conical portion of the balloon 444 and when the balloon 450 is expanded, the guide tubes are moved by the expanding balloon 450, outward until they touch the inside wall of the target vessel. Being attached to an inflated balloon 450 provides both radial and lateral mechanical support for the guide tubes 415. It is envisioned that there are several techniques for creating the structure of guide tubes 415 attached to the balloon 450. Upon expansion, the inflatable balloon 450 deflects the guide tubes outward toward the interior wall of the vessel. This embodiment provides significant enhancement in radial and lateral stability of the guide tubes 415 as compared to the design of the INAS 50 as shown in FIG. 1. This is because the balloon 450 provides significant radial support for the guide tubes 415.

In a second embodiment, the guide tubes 415 are manually advanced and retracted and the conical portion 444 of the balloon 450 acts as a deflection surface similar to the curved ramp 144 of the PTAC 100 of FIG. 4, the deflection surface deflecting the distally moving guide tubes 415 outward toward the interior wall of the target vessel.

In some embodiments, it is preferred that the expanded balloon 450 be smaller in diameter than the lumen of the target vessel. This will allow the guide tubes 415 to extend outward beyond the expanded balloon 450. This is shown in FIG. 16, where the guide tubes 415 with radiopaque markers 422 extend beyond the surface of the balloon 450. Thus, when expanded, the balloon 450 would not obstruct blood flow as the blood would be able to flow around the outside of the balloon 450. The balloon 450 can be a non-compliant balloon to ensure there is space between the outside of the balloon and the inside wall of the target vessel for blood to flow. For example, good blood flow can be accomplished using a cylindrical balloon with a conical proximal section, wherein this balloon design is much easier to construct than the cloverleaf design of Chan.

In some embodiments, the guide tubes 415 may be attached to the inner tube 405. Then, only the injector tubes 416 would be capable of longitudinal movement within the PTAC 400.

Similar to prior embodiments the PTAC 400 can be configured to be advanced over a separate guide wire or have no guide wire at all. Also the guide tubes 415 and injector tube 416 can be combined similar to the design of the PTAC 380 of FIG. 15.

For the configuration shown in FIG. 16, a sheath 402 with distal radiopaque marker band 413 has been pulled back to allow the guide tubes 415 to expand outwardly. The radiopaque wire 418 and the radiopaque marker bands 422, 424 and 413 may be made from any high density metal such as gold, platinum or tantalum or an alloy of such metals.

The balloon 450 may be compliant, semi-compliant or non-compliant, however an elastic compliant balloon can be preferred as it allows diameter of the expanded guide tubes 415 to be easily set by using different inflation pressures for the balloon 450. Attaching the guide tubes 415 to the outside of the balloon simplifies construction as compared to attempting to place guide tubes 415 within the balloon. This design also allows the distal end 429 of the guide tubes 415 to be the points of engagement with the interior wall of the target vessel so that the entire balloon 450 does not touch the wall. Having the balloon 450 touch the wall can remove some endothelial cells and produce neointimal hyperplasia which is undesirable. The balloon could typically be inflated to a pressure between 10 and 100 psi by injection of normal saline through the inflation lumen 433.

While FIG. 16 shows an inflatable balloon 450 used to provide radial and lateral support for the guide tubes 415, it is envisioned that any mechanical structure that can be expanded under the guide tubes 415 could be used. Such a structure may or may not actually be attached to the guide tubes. For example a structure similar to that of many car jacks that when the ends come together opens up could be used. A screw thread or just a wire or tube that pulls the ends together would be sufficient to form a structure that would support the guide tubes 415

It is also envisioned that an inflatable balloon such as the balloon 450 of FIG. 16 could be added to the PTAC 200 with intravascular centering mechanism (ICM) 250 of FIG. 12. This would be applicable whether the guide tubes 215 with ICM 250 are self-expanding or manually expandable.

FIG. 17 is a schematic view of the central buttress 121 of the PTAC 100 of FIGS. 3 and 4. The distal tip 145 with neck 146 provides attachment to the proximal portion of the distal tip 106 of the PTAC 100 as shown in FIGS. 3 and 4. The curved ramps 144 provide radial and lateral support for the guide tubes 115 as they are advanced forward and slide along and outward as directed by the curved ramps 144. The distal fingers 142 have beveled inside surfaces 148 that also provide lateral support for the guide tubes 115 as they are advanced. The curved structures 142 (as can be seen in FIG. 4) are attached inside of the outer tube extension 104.

FIG. 18 illustrates longitudinal cross-sections of three central portions of the PTAC 100 of FIGS. 2 through 11. At the proximal end of the central portion of the PTAC 100 are three concentric metal hypotubes, an outer hypotube 82, middle hypotube 83 and inner hypotube 85. These are typically made from thin walled metallic tubing such as stainless steel, L605, cobalt chromium or nitinol. The outer hypotube 82 of the PTAC 100 attaches at its distal end to a proximal plastic outer tube 92 typically made from a relatively high durometer plastic, for example polyimide. As seen in the central cross-section of FIG. 18, the proximal plastic tube 92 attaches at its distal end to the proximal end of the outer tube 102 also shown in FIGS. 2 through 11. The outer tube 102 is typically made from a lower durometer/ more flexible plastic than the proximal plastic tube 92.

As shown in the proximal section of FIG. 18, the middle hypotube 83 is attached at its distal end to the middle tube 103. As shown in the central section of FIG. 18, the inner hypotube 85 with central injection lumen 93 is attached at its distal end to the proximal end of the inner tube 105 having an injection lumen 133.

Also shown in distal section of FIG. 18 is the manifold 125 that connects the inner tube 105 to the injector tubes 116 of FIGS. 3 and 4 and the radiopaque wires 118 that run the length of the injector tubes 116 to provide visibility under fluoroscopy. The manifold 125 lies coaxially within the inner tube 105 in a portion of the inner tube 105 that is proximal to the distal end of the inner tube 105. The proximal end of the inner tube 105 is also coaxially positioned within the outer tube 102 which is proximal to the outer tube extension 104 of FIGS. 2-10.

Figures 19, 20:
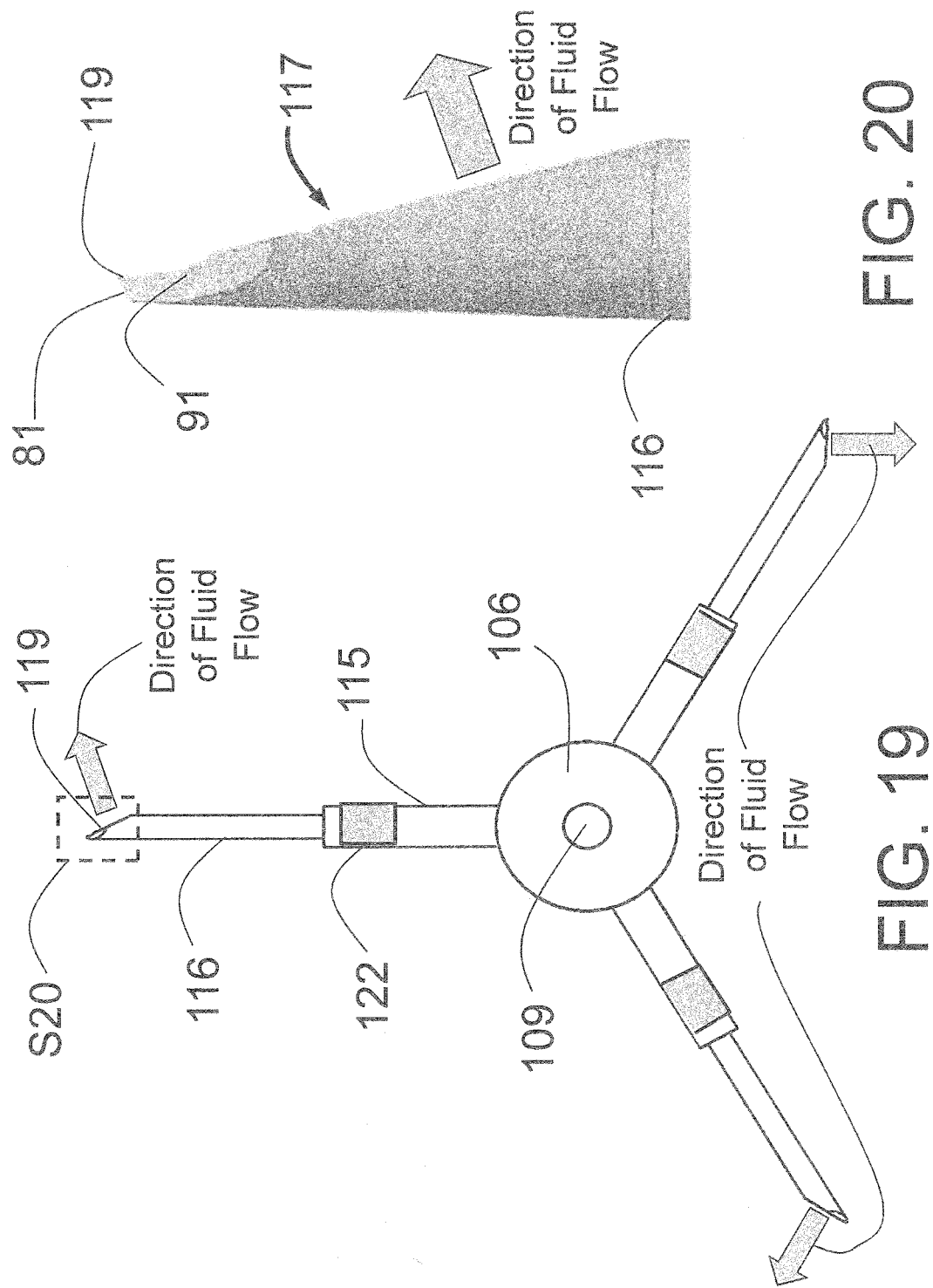
FIG. 19 is a schematic view showing the orientation of the sharpened injection needles as they would appear at the distal end of the PTAC.
FIG. 20 is a schematic view of a preferred shape of the sharpened injection needles.

FIG. 19 is a schematic view of the distal end of the fully expanded PTAC 100 of FIGS. 2 through 10 showing the orientation of the sharpened injection needles 119 with respect to the distal end of the PTAC 100. FIG. 19 is the view looking down the longitudinal axis of the PTAC 100 from its distal end. The tip of the guide wire 109 and tapered distal section 106 are clearly seen as are the three expanded guide tubes 115 with radiopaque markers 122. The expanded injector tubes 116 with distal injection needles 119 are shown with the cut portion of the needles 119 being cut so that the open face of the needle 119 will deliver the ablative fluid in a direction that is perpendicular to the longitudinal axis of the PTAC 100 and the face of the bevel cut of the needle 119 faces laterally with respect to the axis of the needle 119.

This configuration is advantageous as it reduces the probability that the point of the needle 119 will get caught on the inside of the guide tube 115 as the needle 119 is advanced.

FIG. 20 is a schematic view of an enlargement of section S20 of FIG. 19 showing a preferred shape of the sharpened injection needles 119. FIG. 20 shows a direction of ablative fluid flow from the needle distal opening 117 that is perpendicular to the longitudinal axis of the PTAC 100. Also shown is the additional cut 91 in the needle tip 81 which provides a sliding surface. The direction of the main cut of the needle 119 as well as the additional cut 91 combine to reduce the chance of having the needle tip 81 accidently get caught on the inside of the guide tube 115 as the needle 119 is advanced through the guide tube 115.

FIG. 21A is a schematic view of an alternative embodiment which is the PTAC 500. The PTAC 500 uses the proximal portion of the obturator 520 as the support structure for the guide tubes 515. The obturator 520 has proximal section 523, radiopaque marker band 524 and distal tapered section 506. The proximal section 523 has slots 525 into which the guide tubes 515 will nest or fit. The outer tube 502 forms the outside of the PTAC 500 and acts as a sheath that can be advanced over the proximal portion 523 of the obturator 520 to form a closed structure. The inner tube 505 is a tube within the structure of the outer tube 502 which provides the impetus for motion of the injection needles 519 (not shown). The wire 503 is the structure which provides the impetus for motion of the guide tubes 515. The core wire 511 is connected to the obturator 520 and a mechanism at the proximal end of the PTAC 500 facilitates longitudinal motion of the obturator 520 with respect to the outer tube 502 and/or guide tubes 515. A fixed guide wire 509 is shown although the PTAC 500 could be configured to be delivered over a guide wire or with a distal end with no guide wire such as the PTAC 380 of FIG. 15.

FIG. 21A shows the configuration of the PTAC 500, after the guide tubes 515 are advanced, but before the needles 519 are advanced. The guide tubes 515 can be manually advanced as they are with the PTAC 100 of FIGS. 2 through 11 or they can be self-expanding as in the prior art PTAC 50 of FIG. 1 when the outer tube 502 acts as a sheath and is pulled back to allow the guide tubes 515 to expand outwardly. The next step following the configuration of FIG. 21A, is for the obturator 520 to be moved proximally (pulled back) by the proximal motion of the core wire 511 actuated by the mechanism in the proximal section of the PTAC 500. This will cause the slots 525 to move proximally until they nest up against the expanded guide tubes 515 providing both radial and lateral support, similar to the central buttress 121 shown in FIG. 17. Once the obturator 520 is pulled back, the needles 519 are advanced into the wall of the target vessel in the configuration shown in FIG. 21B.

FIG. 21B shows the configuration of the PTAC 500 following advancement of the needles 519 at the distal ends of the injector tubes 516 into the wall of the target vessel. The obturator 520 provides radial support for the guide tubes 515 to prevent them backing away from the interior vessel wall as the needles 519 are advanced. The slots 525 also provide lateral support to keep the guide tubes 515 and needles 519 positioned at 120 degrees with respect to each other for uniform injection of the ablative fluid into or outside of the wall of the target vessel. As in prior embodiments, the guide tubes 515 are the needle guiding elements. In this embodiment the obturator 520 is a longitudinally movable mechanism that provides the radial and lateral support for the needle guiding elements which are the guide tubes 515.

While this specification has focused on use of the PTAC for use in ablation of tissue, it is also clearly envisioned that the apparatus and methods of FIGS. 1-21B inclusive can be applied to inject any fluid for any purpose including that of local drug delivery into a specified portion of a blood vessel or the volume of tissue just outside of a blood vessel, or into prostatic tissue via the prostatic urethra.

While the embodiments shown in FIGS. 1 through 21B show either three or four injection needles, the presently disclosed structure which includes radial and/or lateral support mechanisms for needle guiding elements that guide injection needles as they penetrate the interior wall of a target vessel can be applied to designs with one needle, two needles or 5 or more needles. Even a single needle design would be of smaller diameter and easier to use than other single needle systems such as the Bullfrog system of Mercator.

Various other modifications, adaptations, and alternative designs are of course possible in light of the above teachings. Therefore, it should be understood at this time that within the scope of the appended claims the invention may be practiced otherwise than as specifically described herein. It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "expanding a balloon" include "instructing the expanding of a balloon." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A catheter comprising:
a catheter body having a distal portion extending in a longitudinal direction with at least two openings in the distal portion;
at least two needle guiding elements adapted to advance outwardly through the at least two distal openings in the catheter body toward an interior wall of a target vessel;
at least two injection needles, each injection needle having an injection lumen, the at least two injection needles adapted to be advanced outwardly, guided by the at least two needle guiding elements, to penetrate the interior wall of the target vessel, each injection needle having a distal opening for fluid delivery;
a control mechanism adapted cause the simultaneous outward advancement of the at least two injection needles beyond distal ends of the at least two needle guiding elements; and
a lock, wherein the lock is adapted to be unlocked to allow motion of the at least two injection needles.

2. The catheter of claim 1, wherein the control mechanism is adapted to move the at least two injection needles distally and proximally.

3. The catheter of claim 1, wherein the lock is a button.

4. The catheter of claim 3, wherein the button is adapted to be depressed to be unlocked to allow motion of the at least two injection needles.

5. The catheter of claim 1, wherein the control mechanism is adapted to allow relative longitudinal motion of an internal tube relative to another internal tube.

6. The catheter of claim 1, wherein the control mechanism is adapted to be pushed forward to move the at least two injection needles forward.

7. The catheter of claim 1, wherein the at least two needles guiding elements are adapted to interact with a buttress within the catheter body.

8. The catheter of claim 1, wherein the at least two injection needles are adapted to be retracted until a click or stop occurs.

9. A catheter comprising:
a catheter body extending in a longitudinal direction;
at least two needle guiding elements adapted to advance outwardly toward an interior wall of a target vessel;
at least two injection needles, each injection needle having an injection lumen, the at least two injection needles adapted to be advanced outwardly, guided by the at least two needle guiding elements, to penetrate the interior wall of the target vessel, each injection needle having a distal opening for fluid delivery;
a control mechanism adapted cause the simultaneous outward advancement of the at least two injection needles beyond distal ends of the at least two needle guiding elements; and
a lock, wherein the lock is adapted to be unlocked to allow motion of the at least two injection needles, wherein the lock is adapted to be unlocked only when the at least two needle guiding elements are fully deployed.

10. The catheter of claim 9, wherein the control mechanism is adapted to move the at least two injection needles distally and proximally.

11. The catheter of claim 9, wherein the control mechanism is adapted to be pushed forward to move the at least two injection needles forward.

12. The catheter of claim 9, wherein the at least two injection needles are adapted to be retracted until a click or stop occurs.

13. A catheter comprising:
a catheter body extending in a longitudinal direction;
at least two needle guiding elements adapted to advance outwardly toward an interior wall of a target vessel;
at least two injection needles, each injection needle having an injection lumen, the at least two injection needles adapted to be advanced outwardly, guided by the at least two needle guiding elements, to penetrate the interior wall of the target vessel, each injection needle having a distal opening for fluid delivery;
a control mechanism adapted cause the simultaneous outward advancement of the at least two needle guiding elements beyond the catheter body; and
a lock, wherein the lock is configured to be unlocked to allow motion of the at least two needle guiding elements, wherein the at least two needle guiding elements are adapted to advance outwardly from respective openings in the catheter body.

14. The catheter of claim 13, wherein the control is adapted to move the at least two needle guiding elements distally and proximally.

15. The catheter of claim 13, wherein the lock is a button.

16. The catheter of claim 15, wherein the button is adapted to be depressed to be unlocked to allow motion the at least two needle guiding elements.

17. The catheter of claim 13, wherein the control mechanism is adapted to be pushed forward to move the at least two needle guiding elements forward.

18. The catheter of claim 13, wherein the at least two needle guiding elements are adapted to interact with a buttress within the catheter body.

19. The catheter of claim 13, wherein the at least two injection needles are configured to be coaxially advanced within the at least two needle guiding elements.

20. A catheter comprising:
a catheter body extending in a longitudinal direction;
at least two needle guiding elements adapted to advance outwardly toward an interior wall of a target vessel;
at least two injection needles, each injection needle having an injection lumen, the at least two injection needles adapted to be advanced outwardly, guided by the at least two needle guiding elements, to penetrate the interior wall of the target vessel, each injection needle having a distal opening for fluid delivery;
a control mechanism adapted cause the simultaneous outward advancement of the at least two needle guiding elements beyond the catheter body; and
a lock, wherein the lock is configured to be unlocked to allow motion of the at least two needle guiding elements, wherein the lock is adapted to be unlocked only when the at least two injection needles are fully retracted within the at least two needle guiding elements.

21. The catheter of claim 20, wherein the control mechanism is adapted to move the at least two needle guiding elements distally and proximally.

22. The catheter of claim 20, wherein the control mechanism is adapted to be pushed forward to move the at least two needle guiding elements forward.

* * * * *